(12) United States Patent
Zhang et al.

(10) Patent No.: US 10,689,691 B2
(45) Date of Patent: Jun. 23, 2020

(54) UNBIASED IDENTIFICATION OF DOUBLE-STRAND BREAKS AND GENOMIC REARRANGEMENT BY GENOME-WIDE INSERT CAPTURE SEQUENCING

(71) Applicants: The Broad Institute Inc., Cambridge, MA (US); Massachusetts Institute of Technology, Cambridge, MA (US)

(72) Inventors: Feng Zhang, Cambridge, MA (US); Winston Yan, Brookline, MA (US); David A. Scott, Cambridge, MA (US); Aaron Smargon, Cambridge, MA (US); Mohammed Reza Mirzazadeh, Stockholm (SE); Nicola Crosetto, Stockholm (SE)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/626,853

(22) Filed: Jun. 19, 2017

(65) Prior Publication Data
US 2018/0163265 A1 Jun. 14, 2018

Related U.S. Application Data

(63) Continuation-in-part of application No. PCT/US2015/067138, filed on Dec. 21, 2015.
(Continued)

(51) Int. Cl.
C12Q 1/6855 (2018.01)
C12N 9/22 (2006.01)
(Continued)

(52) U.S. Cl.
CPC .......... *C12Q 1/6855* (2013.01); *C12N 9/22* (2013.01); *C12N 9/96* (2013.01); *C12N 15/11* (2013.01);
(Continued)

(58) Field of Classification Search
None
See application file for complete search history.

(56) References Cited

FOREIGN PATENT DOCUMENTS

| KR | 2003 0065058 A | 6/2013 |
|---|---|---|
| WO | 2013/006745 A2 | 1/2013 |
| WO | 2014/093701 A1 | 6/2014 |

OTHER PUBLICATIONS

Crosetto et al., "Nucleotide-resolution DNA double-strand break mapping by next-generation sequencing," Nat. Methods 2013, 10: 361-365, with 3 pages of supplementary Online Methods, published online Mar. 17, 2013. (Year: 2013).*
(Continued)

*Primary Examiner* — Kaijiang Zhang
(74) *Attorney, Agent, or Firm* — Foley & Lardner LLP; Sunit Talapatra; Tainran Yan

(57) ABSTRACT

The invention provides for systems, methods, compositions, and kits for the complete characterization of targeted nuclease specificity which necessitates techniques that can assess the full possibility space of off-target activity and genomic stability following genome editing. Also provided are the materials and techniques which enable the comprehensive genomic stability accompanying a range of cellular perturbations, including genome editing (ZFN, TALEN, CRISPR, and future technologies) and disease modeling among other applications.

21 Claims, 26 Drawing Sheets

Specification includes a Sequence Listing.

Related U.S. Application Data

(60) Provisional application No. 62/094,903, filed on Dec. 19, 2014.

(51) Int. Cl.
| | |
|---|---|
| *C12N 9/96* | (2006.01) |
| *C12N 15/11* | (2006.01) |
| *C12N 15/90* | (2006.01) |
| *C12Q 1/6848* | (2018.01) |
| *C12Q 1/6869* | (2018.01) |
| *C12Q 1/6876* | (2018.01) |

(52) U.S. Cl.
CPC .......... *C12N 15/907* (2013.01); *C12Q 1/6848* (2013.01); *C12Q 1/6869* (2013.01); *C12Q 1/6876* (2013.01); C12N 2310/20 (2017.05); C12N 2320/11 (2013.01); C12N 2800/80 (2013.01)

(56) References Cited

OTHER PUBLICATIONS

Van Gelder et al., "Amplified RNA synthesized from limited quantities of heterogeneous cDNA," Proc. Natl. Acad. Sci. USA 1990, 87:1663-1667. (Year: 1990).*

Frock et al., "Genome-wide detection of DNA double-stranded breaks induced by engineered nucleases," Nat. Biotechnol. 2015, 33:179-186, with 2 pages of supplementary Online Methods, published online Dec. 15, 2014. (Year: 2014).*

N.A. Tchurikov, et al., Mapping of Genomic Double-Strand Breaks by Ligation of Biotinylated Oligonucleotides to Forum Domains: Analysis of the date obtained for Human rDNA units, Genomics Data (Nov. 2014) vol. 3, No. 12, p. 15-18.

Richard L. Frock, et al., Genome-wide Detection of DNA Double-Stranded Breaks Induced by Engineered Nucleases, Nature Biotechnology (Dec. 2014) vol. 33, No. 2, p. 179-186.

Nicola Crosetto, et al., Nucleotide-resolution DNA Double-Strant Break Mapping by Next-Generation Sequencing, Nature Methods (Mar. 2013) vol. 10, No. 4, p. 361-365.

* cited by examiner

FIG. 5A  DNA insert elements
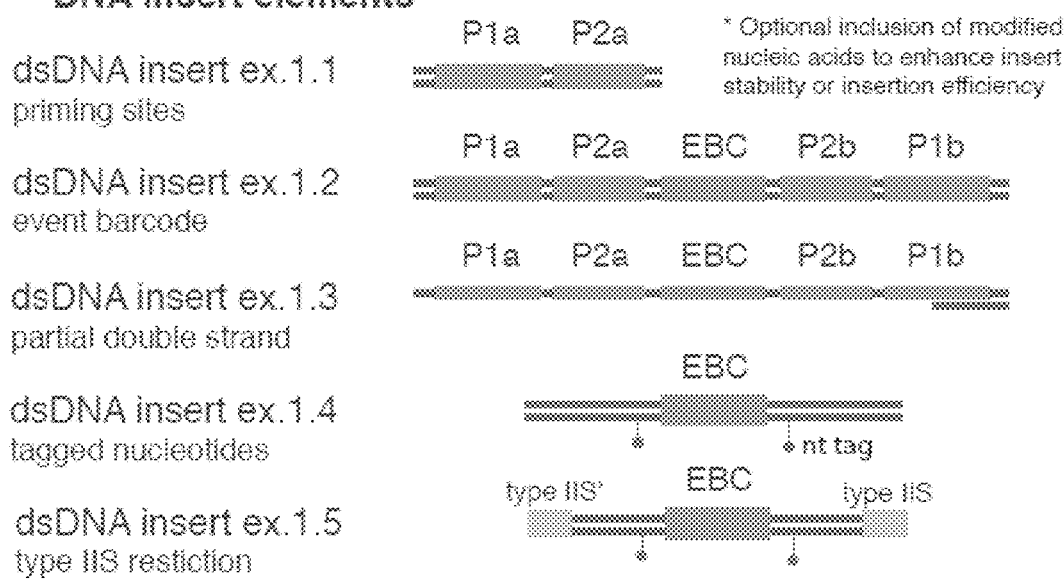
FIG. 5B  ligation handle configurations
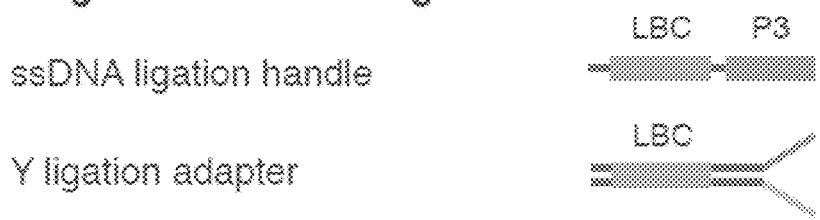

FIG. 5C  genomic event capture
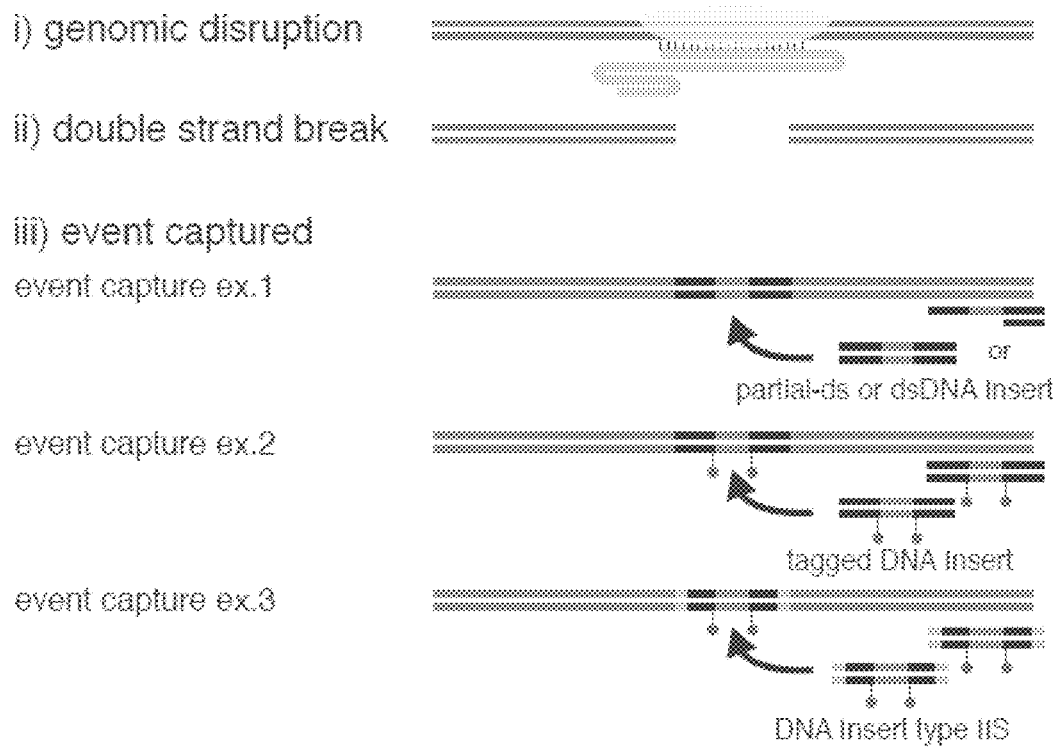
FIG. 5D  optionally: genomic insert event propagation
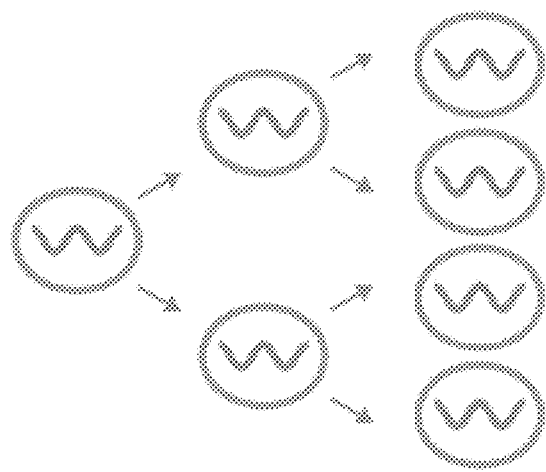

FIG. 6A  genomic insertion event
FIG. 6B  genomic event propagation, sample division, and nrLAM
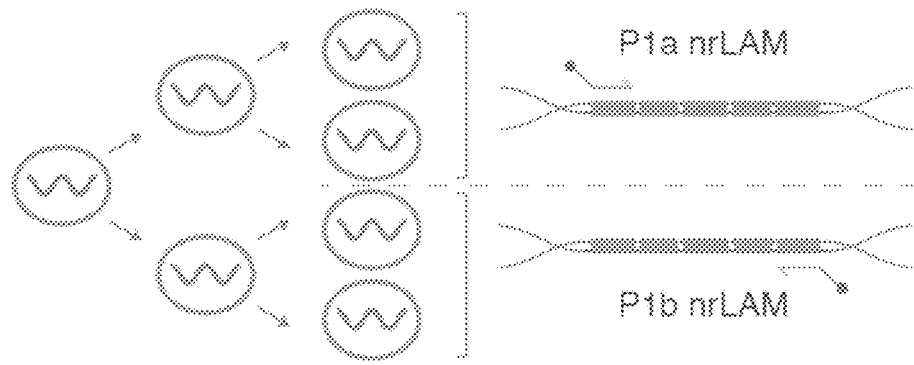
FIG. 6C  affinity capture, library prep
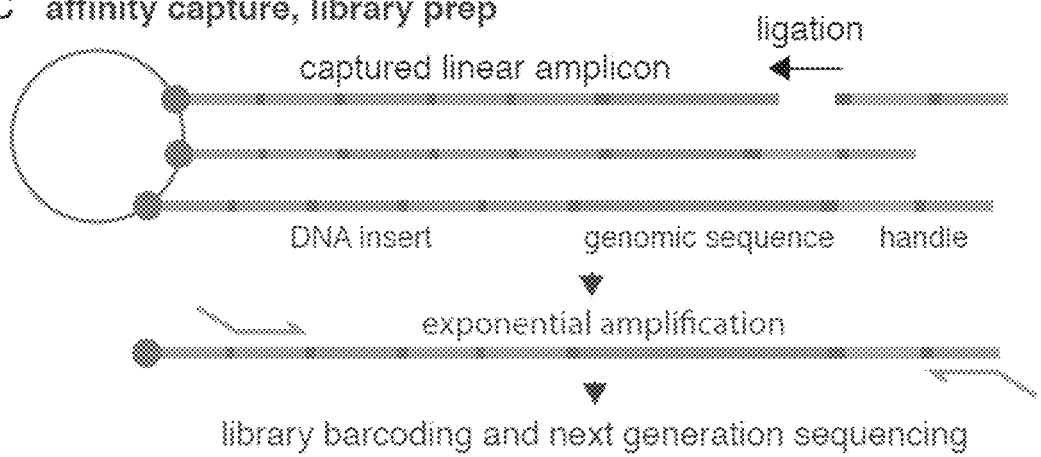
FIG. 6D  junction mapping
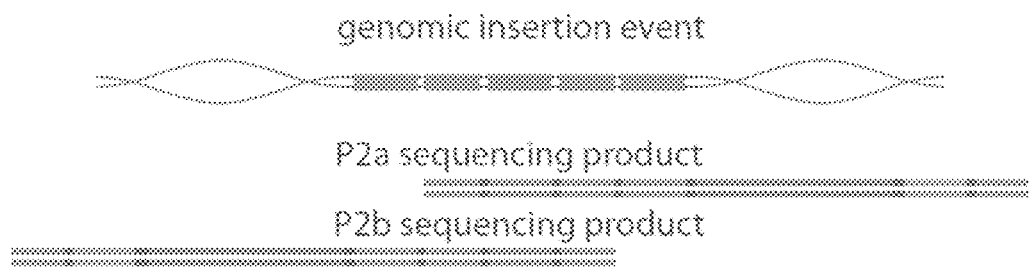

FIG. 7A  genomic insertion event

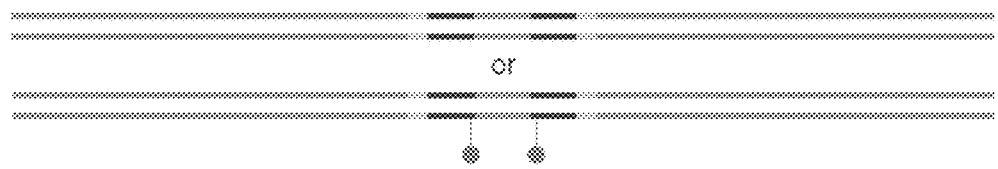

FIG. 7B  fragmentation 1.1) genomic fragmentation
(dsDNA insert)

1.2) insert excision
(type IIS insert)

FIG. 7C  library preparation i) affinity capture ex.1
   oligo capture i) affinity capture ex.2
   affinity tag ii) end repair +
    a-tailing iii) adapter ligation +
     enrichment

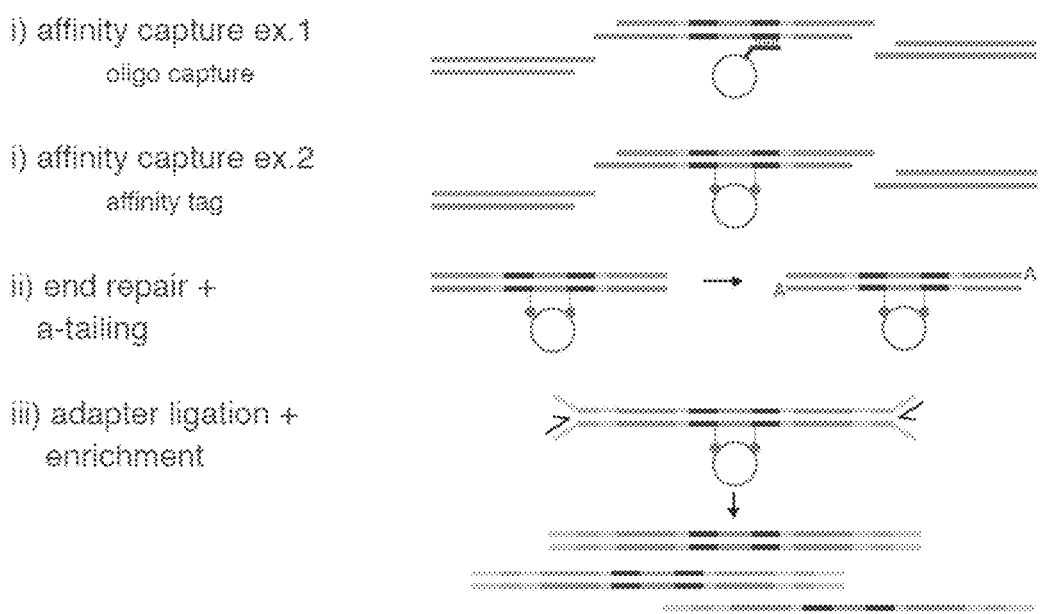

FIG. 7D optionally: sequencing strategies i) outside-in sequencing ii) inside-out sequencing iii) combination thereof

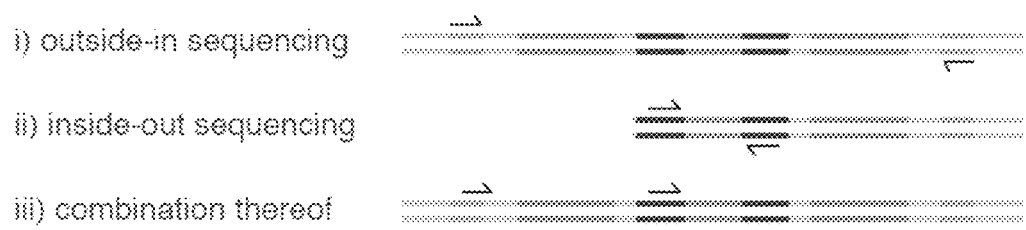

CGATTGAGGCCGGTAATACGACTCACTATAGGGGTTCAGAGAGTTCTACAGTCCGACGATCNNNNNNGTCGTATC

GCTAACTCCGGCCATTATGCTGAGTGATATCCCCAAGTCTCAAGATGTCAGGCTGCTAGNNNNNNCAGCATAG

T7 Promoter | RNA template | DNA | Barcode

Fig. 17

BLESS

- Fixation after scraping off plate
- Cell / nuclear lysis
- Blunting
- Biotinylated adapter ligation
- Proteinase K digestion
- Sonication / shearing
- Biotin pulldown for library enrichment
- Distal adapter ligation
- PCR enrich
- Truseq library prep

BLISS

- Fixation on plate ⎤
- Cell / nuclear lysis ⎥ Minimal sample loss; in situ format can be readily done on mounted tissue sections for in vivo off target analysis
- Blunting ⎥
- T7 adapter ligation ⎦
- Proteinase K digestion
- Sonication / shearing
- In vitro transcription for library enrichment — UMIs and linear amplification during IVT prevents/allows correction of bias
- RNA library prep

Fig. 24

UNBIASED IDENTIFICATION OF DOUBLE-STRAND BREAKS AND GENOMIC REARRANGEMENT BY GENOME-WIDE INSERT CAPTURE SEQUENCING

RELATED APPLICATIONS AND INCORPORATION BY REFERENCE

This application is a continuation-in-part of International patent application Serial No. PCT/US2015/067138 filed Dec. 21, 2015 and published as PCT Publication No. WO2016/100974 on Jun. 23, 2016 and which claims benefit of and priority from U.S. application Ser. No. 62/094,903, filed Dec. 19, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant numbers MH100706 and MH110049 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 24, 2017, is named 50141_01_2006_SL.txt and is 23,259 bytes in size.

FIELD OF THE INVENTION

The present invention generally relates to systems, methods and compositions used for the control of gene expression involving sequence targeting, such as genome perturbation or gene-editing, that may use vector systems related to Clustered Regularly Interspaced Short Palindromic Repeats (CRISPR) and components thereof.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

Double stranded breaks (DSBs) represent a major threat to the stability of the genome, and unrepaired DSBs can result in potentially oncogenic chromosomal deletions, amplifications, and translocations. DSBs can be caused by exogenous agents (ionizing radiation; chemicals, including various agents used in anti-cancer chemotherapy) as well as by endogenous processes (metabolic reactive oxygen by-products; replication fork collapse). Recently, genome-editing nucleases have emerged as a highly relevant potential cause of undesired, off-target DSBs. There is currently a growing interest in different research fields in developing methods that can portrait the genome-wide landscape and precise location of DSBs under various conditions:

SUMMARY OF THE INVENTION

There exists a pressing need for alternative and robust systems and techniques for sequence targeting with a wide array of applications. This invention addresses this need and provides related advantages. The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

The genome-editing community is highly interested in measuring the levels and location of off-target DSBs induced by editing nucleases such as the CRISPR/Cas9 system. This is particularly relevant in a clinical context, where such nucleases are used for gene therapy purposes. Further, the genome instability/DNA repair community is highly interested in understanding if different DNA damage modalities and/or repair pathway derangement result in different breakomes. Also, the oncology/radiotherapy community is interested in developing clinical biomarkers of DNA damage caused by chemo- and radiation therapy modalities. The space exploration community is interested in developing biomarkers of DNA damage for astronauts and future space travellers.

In one aspect, the invention provides a method for unbiased detection of double strand break sites and genomic rearrangement events in mammalian cells. This method allows comprehensive analysis of genomic stability accompanying a range of cellular perturbations, including genomic editing (ZFN, TALEN, CRISPR, as well as future technologies) and disease modeling among other applications. The application of the "all-to-all" concept, i.e., the ability to map all genomic insertions or rearrangement events to all corresponding points of translocations has broad applications, such as disease modeling (disease progression models), drug development, clinical trials, improve study disease, and new treatment combinations.

In one aspect, the invention provides improved methods for identifying and selecting genomic editing systems and components with improved target specificity. More particularly, the inventive methods provide for assessing genome-wide effects of genome editing systems, avoiding bias resulting from preselection of off-targets and minimizing the influence of non-specific genomic events that might otherwise resemble off-target editing events by genome-editing nucleases.

In certain embodiments, the invention features in situ methods to detect DSBs in fixed cells. In such embodiments, the invention may be referred to as Double-Strand Breaks Labeling In Situ and Sequencing or "BLISS." Key advantages of BLISS include: 1) compatibility with small amounts of input material (few thousands of cells and possibly even single cells) without major risk of sample loss during multiple protocol steps; 2) applicability to tissue sections and, therefore, possibility to study clinically relevant specimens; 3) assay scalability using multi-well plates or microfluidic devices to differentially barcode numerous samples in a highly parallelized manner; 4) quantitative measurements thanks to accurate cell counting, minimization of technical errors associated with in situ blunting and ligation, and robust sequencing data processing thanks to the use of UMIs. Unlike other methods, BLISS detects DSBs that have not yet been repaired by non-homologous end joining (NHEJ) or homologous recombination (HR), therefore providing a truly unbiased genome-wide measurement of the breakome. The method can be applied to small amounts of essentially any cell type making it effective translation of genome-editing tools in a clinical context.

Insert Capture Methods

Insert capture methods have been developed for identification of cuts from restriction enzymes or DNA damaging agents. However, improved sensitivity is advantageous for accurate detection of low abundance off-target cutting in CRISPR samples. In an aspect, the invention provides new and improved methods of insert capture useful for identifying and classifying DSBs. The methods comprise improved sensitivity and reduced bias through careful selection of reagents and conditions. In certain embodiments, the improvements comprise reduced sample loss and can be performed in situ. For example, whereas 10M cells may be an appropriate amount off starting material for BLESS, the instant methods can use significantly fewer, for example, 0.25M cells. In an aspect, the invention provides in situ methods that feature reduced sample disruption. In an aspect, the invention provides in situ methods that feature reduced background DSBs due to sample manipulation. In an aspect, the invention provides detection of DSBs and off-target cleavage directly in animal tissue.

In certain embodiments, a first linear amplication is featured. In certain embodiments, linear amplification comprises use of Taq polymerase. For example, a Taq polymerase can be used with a single primer in a thermocycling reaction and provide linear amplification. In certain embodiments, the linear amplification comprises transcription from a T7 adapter by T7 polymerase. The T7 adapter can comprise a unique molecular identifier (UMI) and barcode sequences and includes a T7 polymerase binding site for linear amplification of captured inserts and flanking DNA. (FIG. 17). In certain embodiments where adaptors are used, there is no requirement for ligation of second "distal" adapters to enable amplification. In certain embodiments, the invention provides unique molecular identifiers (UMIs). In certain embodiments, transfection and processing in the same 24-well plate allows for high throughput while maximizing the number of cells and minimizing non-specific DSBs.

In an aspect, the invention provides a method for identifying the location of a double strand break (DSB) in DNA of a cell or tissue which comprises ligating an linker to the DSB to create an adapter-DSB conjugate, producing a polynucleotide complementary to the linker-DSB conjugate, and determining the sequence of the complementary polynucleotide; wherein the linker comprises i) a site for linear amplification, ii) a unique molecular identifier sequence for encoding linker-DSB ligation events; and wherein the complementary polynucleotide is a product of a linear amplification, wherein the complementary polynucleotide comprises a sequence of the DNA of the cell adjacent to the DSB.

In an embodiment of the invention, the linear amplification can comprise non-restrictive linear amplification. In an embodiment of the invention, the linear implication can comprise in vitro transcription. In an embodiment of the invention, the linker can comprise a T7 sequence for transcription by T7 polymerase.

An outline of the method is shown in FIG. 16. In certain embodiments of BLISS, cells are first fixed onto microscope slides or microscope coverslips. Adherent cells can be directly grown onto coverslips or treated (e.g., Poly D lysine or Geltrex coated) cell culture media, while suspension cells are spotted onto adhesive slides or pre-coated coverslips (e.g. using poly-L-lysine or similar adhesion matrices). If needed, adherent cells can be first trypsinized and then spotted in desired amounts similarly to suspension cells. Cell fixation is performed using a cross-linking agent (typically, methanol-free paraformaldehyde) directly onto the microscope slide/coverslip for a short period of time (typically, <30 min at 20-25° C.). Slides/coverslips with fixed cells can be stored for several months in a suitable buffer solution at +4° C. (typically, Phosphate Buffer Saline with sodium azide to prevent bacterial growth). Samples in this format can also be conveniently shipped at +4° C. For slides, cells are typically spotted over a small circular area (usually, 1 cm in diameter), so that they can be covered with a suitable hybridization chamber to facilitate downstream steps (for example, we use SecureSeal chambers from Grace Bio-Labs). For tissues, 5-50 micron-thick sections can be cut and mounted on a microscope slide according to conventional histology procedures. Fresh-frozen tissues can be embedded in OCT and sectioned according to standard methods. Frozen sections can be mounted onto adhesive slides or coated coverslips, followed by fixation as for cells. We have not yet assessed standard pathology formalin-fixed, paraffin-embedded (FFPE) tissues, which are fixed for a longer period of time (typically, overnight).

In an aspect, the invention provides a method to detect and map DSBs from any source. Such DSBs can arise spontaneously or from a DNA damaging agent. In preferred embodiments, the invention is used to detect and map DSBs arising from on- and off-target activity of genome-editing agents.

In an embodiment, blunt ending of the DSBs are blunt ended before adapter ligation. In an embodiment, the genomic DNA (also referred to herein as a gDNA) is fragmented in situ before linear amplification. In an embodiment of the invention, the gDNA is subject to fragmentation, for example using a restriction enzyme or sonication (e.g., with a biorupter). In an embodiment, there is an adapter elimination step to remove unligated adapters.

In an embodiment, the linear amplification product is a transcription product and is an RNA. In another embodiment, the linear amplification product is extended from a primer by a DNA polymerase and is a DNA. In certain embodiments, RNA products, for example which can be repeatedly transcribed from a T7 transcription sequence by T7 polymerase in a single reaction step, are preferred.

To determine the sequence or the DSB, the linear amplification product is then sequenced. In an embodiment of the invention, when the linear amplification product is an RNA, reverse transcription is used for 1st strand synthesis. In certain embodiments, a 3' adapter is ligated to the RNA and serves as a substrate for reverse transcription. In an embodiment, the adapter is a sequencing adapter. In certain embodiments, the reverse transcript may be amplified exponentially prior to sequencing, using, for example, primers coinciding with the amplification site of the initial linear amplification and the revere transcription adapter. An example of a commercially available adapter is in an Illumina TruSeq Small RNA Library Preparation Kit.

In certain embodiments, it is advantageous after linear amplification to digest the genomic DNA that was in vitro transcribed (amplified) to avoid inaccurate quantification of a DNA library. In certain embodiments, DNAse is used to digest the in vitro transcribed genomic DNA. In certain embodiments, to prevent adapter dimers from forming and being transcribed, it is useful to avoid PNK treatment of adapters.

In an embodiment of the invention, the reverse transcribed linear amplification product is amplified and sequenced.

The above method is usually multiplexed. For example, as disclosed elsewhere herein, to identify and map DSB hostpots or identify and map CRISPR-induced DSB requires sequencing multiple DSBs in a culture of cells tissue. Thus, in certain embodiments, a preferred adapter comprises a sample barcode and a "unique molecular identifier" or "UMI." The term "UMI" refers to a sequencing linker used in a method that uses molecular tags to detect and quantify unique amplified products. A UMI is used to distinguish effects through a single clone from multiple clones. In the instant invention, a UMI may be used to distinguish DSBs in individual cells, for example to identify sequences from opposite sides of a DSB. A sequencer linker with a random sequence of between 4 and 20 basepairs and an index sequence is added to the 5' end of the template, which is amplified and sequenced. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI is designed such that assignment to the original can take place despite up to 4-7 errors during amplification or sequencing.

The invention also provides insert capture methods and compositions for detecting and mapping a double strand break or genomic rearrangement event in DNA in a cell or cell culture.

In an aspect, the invention provides a method for detecting and mapping a double strand break or genomic rearrangement event in genomic DNA in a cell or cell culture of interest comprising: transfecting or transducing a cell of interest with at least a DNA insert, culturing the cell of interest with at least the DNA insert, producing a subpopulation of cells with individual insertion events, amplifying the DNA insert, extracting the genomic DNA, isolating a single stranded or a double stranded DNA fragment(s) comprising DNA inserts and flanking genomic DNA, and identifying a genomic sequence flanking at least one or both sides of the DNA insert.

In an embodiment of the invention, DNA is extracted at multiple time points from the transfected or transduced cell. In an embodiment of the invention, the cells are cultured for a period of time from about 1 minute to 100 days prior to isolation of genomic DNA. In another embodiment, the cells are cultured for a period of time from about 24 hours to 60 days. In another embodiment, the cells of interest are cultured for a period of time from about 5 days to 30 days.

In certain embodiments the cells comprising and individual insertion event are split into two fractions. In certain embodiments, the transfected or transduced cell is multiplied through cell-division and a resulting subpopulation is split into separate fractions and the DNA insert and flanking genomic DNA on either side of the DNA insert are amplified by non-restrictive linear amplification In certain embodiments the transfected or transduced cell is split into separate fractions and the DNA insert is first amplified using non-restrictive linear amplification then followed by exponential amplification.

In an embodiment of the invention, an amplicon is prepared by capturing at least one non-restrictive linear product on marker beads or complimentary nucleotide baits and ligated to handles comprising the DNA insert.

In an embodiment of the invention, genomic DNA isolated from transfected or transduced cells is fragmented to excise DNA inserts and flanking genomic DNA. This can comprise, without limitation, sonication, endonuclease digestion, or tagmentation.

In an embodiment of the invention, an amplicon is prepared by capturing a genomic fragment comprising the DNA insert or non-restrictive linear product on marker beads or complimentary nucleotide baits. In one such embodiment, the marker beads are biotinylated beads.

In an embodiment of the invention, an amplicon comprising the DNA insert and flanking genomic sequence is ligated to a single stranded, double stranded, or partially single stranded and double stranded DNA handle. In one such embodiment the DNA handle comprises a unique molecular identifier for molecular counting.

In certain embodiments the DNA handle comprises a primer sequence for PCR. In certain embodiments, the DNA handle comprises a barcode for sample identification and handles for sequencing.

In an embodiment of the invention fragments containing DNA inserts and flanking genomic DNA are isolated using affinity purification of fragments comprising DNA inserts. In an embodiment of the invention affinity purification of fragments include capture of DNA inserts on substrate based on incorporation of nucleic acid tags into the DNA insert or inclusion of specific sequence in the DNA insert for oligo bait affinity purification.

In an aspect, the invention provides a method for assessing the phenotypic effects of mutations at individual genomic loci or genomic rearrangement. In an aspect, the invention provides a method for mapping on and off-target genomic editing events. In an aspect, the invention provides a method for the identification of editing at discrete on and off-target loci.

In an aspect, the invention provides a non-naturally occurring or engineered composition comprising a DNA insert, wherein the DNA insert comprises a unique molecular identifier sequence of nucleotides for encoding individual insert events in target cells, the unique molecular identifier flanked by at least one priming site on one or both sides; and wherein the cells are cultured for a period of time of about 1 minute to 100 days prior to isolation of genomic DNA; and optionally, wherein modified nucleotides are added to the DNA insert to enhance to enhance nuclear penetration of insert, insert stability, or insertion efficiency.

In an aspect, the invention provides a non-naturally occurring or engineered composition comprising a DNA insert which comprises at least one priming site or a defined nucleic acid sequence, optionally wherein the nucleic acid sequence contains homology to a genomic locus of interest for homology directed incorporation of the DNA insert, a unique molecular identifier sequence of nucleotides for encoding individual insert events in target cells, the unique molecular identifier is flanked by at least one priming site or a nucleic acid buffer sequence on one or both sides, optionally wherein a flanking sequence contains homology to a genomic locus of interest for homology directed incorporation of the DNA insert, the DNA insert contains at least one or more modified nucleic acids to enhance nuclear penetration of insert, insert stability, or insertion efficiency, the DNA insert contains at least one or more modified nucleic acids for affinity capture or specific nucleotide sequences for capture on oligonucleotide baits, at least two type II nuclease sites at a 5' and 3' end of the DNA insert for excision of the DNA insert and flanking the unique molecular identifier following insert integration into genomic DNA; and wherein the cells are cultured for a period of time of about 1 minute to 100 days prior to isolation of genomic DNA. In certain embodiments, the unique molecular identifier is either an event barcode or a ligation barcode. In certain embodiments, DNA insert is either a partially double stranded DNA insert or a partially single stranded. DNA insert. In certain embodiments, the partially single stranded DNA insert comprises a short 3' double strand cap. In one such embodiments, the nucleotide sequence is greater than 3 nucleotides in length. In another embodiment, the nucleotide sequence is anywhere from 5 to 30 nucleotides in length. In another embodiment, the nucleotide sequence is anywhere from 10 to 25 nucleotides in length. In yet another embodiment, the nucleotide sequence is anywhere from 15 to 20 nucleotides in length. In a further embodiment, the nucleotide sequence is 18 nucleotides in length. In an embodiment of the invention, there is comprised a unique molecular identifier wherein the nucleotide sequence is in a random sequence. In an embodiment, the composition comprises one or more priming sites flanking the event barcode.

In an aspect, the invention provides a kit for isolating, purifying, amplifying, detecting, identifying or quantifying a genomic DNA sequence. In an aspect, the invention provides a kit for mapping and detectecting double strand breaks in genomic DNA in a cell. In an aspect, the kit provides a DNA insert as set forth above.

Version 1.0 DNA inserts contain a unique molecular identifier, here forward referred to as the event barcode (EBC), composed of 5-30 random nucleotides used to encode individual insertion events (18 random nucleotides for the current implementation). EBCs are flanked on both sides by two pairs of priming sites for extraction of genomic sequences on either side of the insert by non-restrictive linear amplification (nrLAM, Paruzynski et al., 2010) and later exponential amplification (FIG. 5a). Double stranded DNA inserts (dsDNA insert) as well as single stranded DNA inserts containing a short 3' double strand cap (ssDNA insert) show similar efficiencies of genomic capture. Importantly, the EBC allows for the identification of unique insertion events at individual genomic loci. To allow for specific amplification from each individual priming site on the DNA insert, all priming sites contain different sequences. Each pair of two priming sites on either side of the EBC facilitate the use of non-restrictive linear PCR and 5' RACE strategies for the extraction of genomic sequence flanking the insert as described below.

During experiments, 2-3×10$^5$ 2931 or K562 cells were transfected with Cas9, sgRNA, and DNA insert, and passaged for 24 h-30 days prior to isolation of genomic DNA (FIGS. 5d, 6b). At each time point DNA inserts were observed at double strand break sites (termed "insert capture events", FIG. 5e). Insert capture events showed minimal or no truncation of the insert and no evidence of homology between the insert and surrounding genomic loci, indicating that inserts are primarily integrated into the genome during non-homologous end joining (NHEJ) repair of double strand breaks. Expansion of cell populations containing inserts resulted in redundant representation of individual insertion events. Subpopulations of cells encoding an individual insertion event were then split into two fractions for the extraction of flanking genomic sequence on both sides of the insert to map genomic junctions (FIG. 6b, FIG. 6d). Additionally, Extraction of DNA at multiple time points allows for tracking of insert frequencies at individual loci or tracking of individual EBC-labeled clones at multiple time points and can be used to assess the phenotypic effects of mutations at individual genomic loci or genomic rearrangement.

After harvesting, samples were split into two fractions, and nrLAM was performed using priming sites P1a or P1b to amplify the event barcode and flanking genomic sequence on opposing sides of the insert junction (FIG. 6b). Due to redundant representation of insertion events in each sample fraction, linear amplicons created during the P1a and P1b nrLAM each capture the event barcode and flanking genomic sequence on opposing sides of the DNA insert. After sequencing, genomic sequences on either side of the insert can be paired by matching EBC sequences on the P1a and P1b nrLAM amplicons to reconstruct the complete junction where the insert was captured (FIG. 6d). The reconstruction of insert junctions enabled the unbiased chromosomal rearrangement events between any two loci in the genome (FIG. 6d, FIG. 10, and FIG. 11). analysis of on and off-target genomic editing events, including the identification of editing at discrete on or off-target loci as well.

To prepare nrLAM amplicons for sequencing, nrLAM products were captured on biotin beads and ligated to handles containing an unique molecular identifier (ligation barcode, LBC) for PCR bias correction and priming site P3 for library enrichment (FIG. 5b, FIG. 5d). Sequencing libraries were prepared from P1a and P1b nrLAM fractions using the P2a/P3 or P2b/P3 priming sites to enrich the DNA libraries by nested PCR. After enrichment, sample barcodes and next generation sequencing (NGS) handles were added to each amplicon prior to NGS sequencing. A computational pipeline was developed to extract the event barcode, genomic flanking sequence, and ligation barcode for all genome-wide DNA insertion events.

In a second set of related designs, referred to as design 2.0 and design 2.1, the DNA inserts contain a unique molecular identifier (EBCs), comprising 5-30 random nucleotides used to encode individual insertion events (18 random nucleotides for the current implementation) similar to the first design (design 1.0) discussed above. EBCs are flanked on both sides by a short buffer sequence (FIG. 5a). The top-strand buffer sequence contains a discrete number of Thymidine molecules in defined positions in the 5' and 3' buffer sequences flanking the EBC for biotin labeling with biotin-14-dATP. Thymidine sites could also be interchanged with any other nucleic acid residue and biotin labeled with a complimentary biotinylated nucleic acid residue. Biotin-14-dATP labeling is performed by annealing 15 nt adapter sequence to the 3' end of a DNA oligo encoding the top strand of the insert followed by synthesis of the bottom strand of the insert with a deoxyribonucleotide mix containing equal parts biotin-14-dATP, dCTP, dGTP, and dTTP. Biotin labeling of any other nucleic acid residue is performed in a similar manner by substituting different biotin-labeled nucleotides during second strand synthesis. As an alternative to biotin labeling during second strand synthesis, oligos encoding the DNA insert top strand can be synthesized with biotin labeled nucleotides followed by second strand synthesis with unlabeled dNTPs.

In addition to the EBC and biotin labeling sites, insert design 2.1 contains two type IIS nuclease sites 0-5 nt from the 5' and 3' end of the insert for excision of the insert and flanking genomic sequence following insert integration into genomic DNA (FIG. 5a, 5c). Several type IIS enzymes such as MmeI and NmeaIII are capable of cutting DNA 18-21 nucleotides away from the nuclease binding site, making it possible to excise inserts and flanking genomic DNA as fragments of a well defined size. These restriction endonucleases bind long recognition sequences greater than or equal to 6 bp and occur infrequently in the genome. Hence, short fragments generated by excising DNA inserts and flanking genomic sequence will be easily separable from the distribution of long fragments generated by cleavage of genomic DNA at random recognition sequences for these enzymes throughout the genome.

During experiments, $1-10 \times 10^6$ 293T or K562 cells were transfected with Cas9, sgRNA, and either design 2.0 or design 2.1 (type IIS) DNA insert, and cultured for 24 hours-7 days hours prior to isolation of genomic DNA. DNA inserts were observed to incorporate at double strand break sites (termed "insert capture events", FIG. 5c). Insert capture events showed minimal or no truncation of the insert and no evidence of homology between the insert and surrounding genomic loci, indicating that inserts are primarily integrated into the genome during non-homologous end joining (NHEJ) repair of double strand breaks.

Samples were harvested using a tissue DNA midi prep procedure. 1-100 μg ($\sim 1.5 \times 10^5$-$1,5 \times 10^7$ cells) genomic DNA containing design 2.0 inserts was fragmented by sonication or digestion with a restriction enzyme that cuts frequently in the genome to generate DNA fragments of length 200-500 bp. Alternatively, genomic DNA containing design 2.1 inserts was digested with NmeaIII or MmeI to extract inserts from genomic DNA (FIG. 7b). Both sonication and type IIS digestion strategies for insert excision, produce single fragments containing the insert and flanking genomic DNA on both sides of the insert. Contrary to design 1.0 where genomic DNA flanking the insert is captured on two separate PCR amplicons followed by pairing of EBCs on each amplicon to computationally reconstruct insert junctions (FIG. 6b, FIG. 6d), designs 2.0 and 2.1 capture the full junction in a single genomic fragment (FIG. 7b). This results in enhanced fidelity and decreased read depths necessary to analyze insert junctions for the designs 2.0 and 2.1.

Following fragmentation of genomic DNA to excise inserts and flanking sequence, genomic fragments containing inserts were captured on biotin beads (FIG. 7c-i). Biotin beads containing DNA inserts and flanking genomic DNA were washed multiple times for the removal of unbound genomic DNA fragments containing no inserts. After washing, biotin-bound DNA fragments were subjected to end repair and a-tailing (FIG. 7e-ii) prior to ligation of y-adapters containing handles for next generation sequencing (FIG. 7d-iii), PCR amplification of ligation products was used for library enrichment prior to sequencing.

Analysis of Genomic Loci Flanking Insertion Sites Identifies Off-Target Loci Modified by Cas9.

Design 1.0 insert, Cas9, and sgRNA targeting VEGFA3 were co-transfected in 293T cells as described above, and cultured for 14 days prior to harvesting ($3 \times 10^5$ cells). Sequencing libraries were prepared as described above to capture DNA inserts and flanking genomic sequence, and insertion events were quantified for each genomic locus positive for DNA inserts. Greater than 2000 unique insertion events were observed at the VEGFA3 on-target locus, and multiple off-target loci with high homology to the VEGFA3 on-target were identified with decreasing enrichment (FIG. 8). Validation of cutting frequencies at these loci showed that the frequency of insert capture events correlates with the frequency of genomic modification at identified on and off-target loci (FIG. 9).

Junction Mapping Demonstrates Genomic Rearrangement Events Resulting from Cas9-Induced Genomic Modification.

To investigate genomic rearrangement resulting from expression of Cas9 and VEGFA3 sgRNA, junctions were reconstructed from the sequencing data by matching EBCs for amplicons containing flanking sequences on the 5' or 3' side of DNA inserts as described above (FIG. 5e). This data provided an unbiased map of genomic rearrangement events occurring between any two genomic loci for each sample. Genomic rearrangement events associated with Cas9 on or off-target genomic modification were analyzed by selecting all genomic rearrangement junctions where one element of the junction mapped to either a VEGFA3 on or off-target locus validated above (FIG. 10, vertical red lines (in color version): on-target, solid; off-target, dotted). This analysis demonstrates that Cas9 on and off-target modification results in genomic rearrangement between Cas9 on/off-targets as well as between Cas9 on/off-targets and spontaneous double strand breaks occurring elsewhere in the genome.

Analysis Methods

Because DSBs can occur during natural biological processes such as replication, especially around pericentromeric and telomeric regions, as well as sample processing steps due to physical shearing, it is important to accurately identify the DSBs induced by Cas9. To do this, we empirically optimized the parameters for each step of our BLESS analysis, as explained in the following subsections: 1. Determining the clustering window for building regions of DSB enrichment ("DSB clusters"), 2. Defining the distribution of pairwise-distances within each DSB cluster, and 3. Background subtraction using negative controls.

In an aspect, the invention also provides analysis methods for detecting, measuring, and discriminating DSBs.

To measure the genome-wide cleavage activity of SaCas9 and SpCas9, an analysis pipline (first optimized with BLESS) has been developed. See, Ran et al., 2015, In vivo genome editing using *Staphylococcus aureus* Cas9, Nature 520:186-191, which is incorporated herein by reference. To develop the method, BLESS (direct in situ breaks labelling, enrichment on streptavidin and next-generation sequencing) was applied to capture a snapshot of Cas9-induced DNA double-stranded breaks (DSBs) in cells. 293FT cells were transfected with SaCas9 or SpCas9 and the same EMX1 targeting guides used in the previous CUP experiment, or pUC19 as a negative control. After cells were fixed, free genomic DNA ends from DSBs were captured using biotinylated adaptors and analysed by deep sequencing. To identify candidate Cas9-induced DSB sites genome-wide, a three-step analysis pipeline was established following alignment of the sequenced BLESS reads to the genome (FIG. 15). First, nearest-neighbor clustering was applied to the aligned reads to identify groups of DSBs (DSB clusters) across the genome. It was sought to separate Cas9-induced DSB clusters from background DSB clusters resulting from low frequency biological processes and technical artifacts, and high-frequency telomeric and centromeric DSB hotspots. From the on-target and a small subset of verified off-target sites (predicted by sequence similarity using a previously established method 22 and sequenced to detect indels), it was observed that reads in Cas9-induced DSB clusters mapped to characteristic, well-defined genomic positions compared to the more diffuse alignment pattern at background DSB clusters. To distinguish between the two types of DSB clusters, in each cluster the distance between all possible pairs of forward and reverse-oriented reads (corresponding to 39 and 59 ends of DSBs) was calculated, and the background DSB clusters were filtered out based on the distinctive pairwise-distance distribution of these clusters (FIGS. 12, 13, 14). Third, the DSB score for a given locus was calculated by comparing the count of DSBs in the experimental and negative control samples using a maximum-likelihood estimate. This analysis identified the on-target loci for both SaCas9 and SpCas9 guides as the top scoring sites, and revealed additional sites with high DSB scores.

1. Determining the Clustering Window for Building Regions of DSB Enrichment

To build the DSB clusters from the sequencing reads, the first 30-bp of sequence reads immediately following the proximal label were mapped using Bowtie to the hg19 or mm9 reference genome, allowing up to 2 mismatches. Following alignment, the reads were grouped using a nearest-neighbor clustering method, hence referred to as "DSB clusters": the genomic coordinate of the 5'-most position (first base) was determined for each read, and reads were grouped by applying a sliding window of width x, i.e. within each DSB cluster, the first base of any given read will be no more than x bp from its adjacent reads. It was empirically determined that 30-bp windows yielded well-defined DSB clusters.

2. Defining the Distribution of Pairwise-Distances Within Each DSB Cluster

The grouping in the previous section using a sliding window identified all DSB regions, but did not distinguish between the ones induced by Cas9 activity and those from background. To determine properties that could be used to separate the two, we compiled a training data set by extracting the reads mapped to the on-target and a subset of known off-target sites. These off target sites, verified by the presence of indels from sequencing, include those predicted based on similarity to the on-target sequence as well as by dCas9-ChIP We additionally included centromeric regions with DSB signals observed in both experimental (Cas9 and sgRNA co-transfected) and negative control (pUC19 transfected) samples to further refine the specificity of the algorithm.

Since every DSB generates two open chromosomal ends, the sequencing reads from either end of the DSB align to the + and − strands of the reference genome. The pattern and distribution of the forward (+ strand aligned) and reverse (− strand aligned) reads in a given DSB cluster can help determine whether it is induced by Cas9. Since the DSB site within a centromeric or telomeric region is not consistent from cell to cell, we expect that such a DSB cluster contains forward and reverse reads that are broadly distributed. This contrasts with DSBs induced by Cas9, which typically occur at a well-defined position 3-bp upstream of the PAM8-10 and result in a characteristic distribution of forward and reverse reads that flank a sharp break site. However, due to end-resection during DNA repair, there can be reads aligned away from the cleavage site.

Cas9-induced DSBs can be distinguished from background events by the following analysis: first, we calculated the distance between every possible pair of forward and reverse reads in the DSB cluster by subtracting the chromosomal coordinate of the first base on reverse read from that of the forward read. A distance of 1 thus represents the reverse and forward reads directly abutting and facing away from each other. Distances of >1 bp indicate reads that are separated by one or more base pairs, and distances of <1 bp indicate reads that overlap. Second, we generated a histogram of these distances for each DSB cluster. Histograms of clusters from centromeric, telomeric, and other background regions had broad distributions of pairwise distances, while the histograms from Cas9-induced DSB clusters were sharp and asymmetric. Finally, to quantify this difference we calculated the fraction of pairwise reads that overlapped by no more than 7 bp (distance≥−6 bp) within all possible pairwise distances in each cluster. Based on the training dataset, we found that in the majority of Cas9-induced clusters, this fraction was greater than 0.99. In using this metric to filter out background clusters, we required that a candidate Cas9-induced DSB cluster should have a minimal fraction number of 0.95. This relaxed cut-off value of 0.95 was selected to increase the sensitivity for detecting bona fide Cas9-induced clusters, particularly for those with fewer read counts where a small number of outlier reads might significantly reduce the fraction value.

3. Background Subtraction Using Negative Controls

Finally, we compared the DSB clusters in the experimental versus the negative control group to locate and remove background signals that should be present in both datasets. The DSB score for a given genomic locus was calculated by comparing the count of pass-filter clusters in the experimental samples with the controls using a maximum likelihood estimate (MLE)1. This score describes the number of expected Cas9-induced DSB clusters per $1 \times 10^5$ reads and allowed the final ranking of all candidate DSB sites.

We have taken the above approach to minimize the use of heuristics and limit the introduction of potential biases during the identification of Cas9-induced DSBs. To assess how effectively the candidate DSB sites from BLESS predict levels of indel formation, we performed targeted deep-sequencing on the top ~30 loci that have the highest DSB scores. This revealed a significant linear correlation between BLESS DSB scores and rates of indel mutations.

In one aspect, the invention provides a method for altering or modifying expression of a gene product. The method may comprise introducing into a cell containing and expressing a DNA molecule encoding the gene product an engineered, non-naturally occurring CRISPR-Cas system comprising a Cas protein and guide RNA that targets the DNA molecule, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In one aspect, the invention provides an engineered, non-naturally occurring CRISPR-Cas system comprising a Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cas9 protein. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a CRISPR-Cas system guide RNA that targets a DNA molecule encoding a gene product and a second regulatory element operably linked to a Cas protein. Components (a) and (b) may be located on same or different vectors of the system. The guide RNA targets the DNA molecule encoding the gene product in a cell and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type III CRISPR-Cas protein and in a preferred embodiment the Cas protein is a Cas9 protein. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and (b) a second regulatory element operably linked to an enzyme-coding sequence encoding said CRISPR enzyme comprising a nuclear localization sequence; wherein components (a) and (b) are located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is *S. pneumoniae*, *S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 3, 4, 5, or more pol I promoters), one or more pol II promoters (e.g., 1, 2, 3, 4, 5, or more pol II promoters one or more pol I promoters (e.g., 1, 2, 3, 4, 5, or more pol I promoters), or combinations thereof. Examples of pol III promoters include, but are not limited to, U6 and promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.)

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

With respect to use of the CRISPR-Cas system in plants, mention is made of the University of Arizona website "CRISPR-PLANT" (www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi: 10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10,1038/cr.2013.114; published online 20 Aug. 2013; Xie, "RNA-guided genome editing in plants using a CRISPR-Cas system," Mol Plant. 2013 November; 6(6): 1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), each of which is incorporated by reference herein including as to how herein embodiments may be used as to plants.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tract: mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes* or *S. thermophilus* Cas9, and may include mutated Cas9 derived from these organisms. The enzyme may be a Cas9 homolog, or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more cells) in which one or more mutations have been introduced to be selected. In a preferred embodiment, the CRISPR enzyme is Cas9. In another preferred embodiment of the invention the cell to be selected may be a eukaryotic cell. Aspects of the invention allow for selection of specific cells without requiring a selection marker or a two-step process that may include a counter-selection system.

With respect to mutations of the CRISPR enzyme, when the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. In an aspect the invention provides as to any or each or all embodiments herein-discussed wherein the CRISPR enzyme comprises at least one or more, or at least two or more mutations, wherein the at least one or more mutation or the at least two or more mutations is as to D10, E762, H840, N854, N863, or D986 according to SpCas9 protein, e.g., D10A, E762A, H840A, N854A, N863A and/or D986A as to SpCas9, or N580 according to SaCas9, e.g., N580A as to SaCas9, or any corresponding mutation(s) in a Cas9 of an ortholog to Sp or Sa., or the CRISPR enzyme comprises at least one mutation wherein at least H840 or N863A as to Sp Cas9 or N580A as to Sa Cas9 is mutated; e.g., wherein the CRISPR enzyme comprises H840A, or D10A and H840A, or D10A and N863A, according to SpCas9 protein, or any corresponding mutation(s) in a Cas9 of an ortholog to Sp protein or Sa protein.

In a further aspect, the invention involves a computer-assisted method for identifying or designing potential compounds to fit within or bind to CRISPR-Cas9 system or a functional portion thereof or vice versa (a computer-assisted method for identifying or designing potential CRISPR-Cas9 systems or a functional portion thereof for binding to desired compounds) or a computer-assisted method for identifying or designing potential CRISPR-Cas9 systems (e.g., with regard to predicting areas of the CRISPR-Cas9 system to be able to be manipulated for instance, based on crystal structure data or based on data of Cas9 orthologs, or with respect to where a functional group such as an activator or repressor can be attached to the CRISPR-Cas9 system, or as to Cas9 truncations or as to designing nickases), said method comprising:

using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-Cas9 crystal structure, e.g., in the CRISPR-Cas9 system binding domain or alternatively or additionally in domains that vary based on variance among Cas9 orthologs or as to Cas9s or as to nickases or as to functional groups, optionally with structural information from CRISPR-Cas9 system complex(es), thereby generating a data set;

(b) comparing, using said processor, said data set to a computer database of structures stored in said computer data storage system, e.g., structures of compounds that bind or putatively bind or that are desired to bind to a CRISPR-Cas9 system or as to Cas9 orthologs (e.g., as Cas9s or as to domains or regions that vary amongst Cas9 orthologs) or as to the CRISPR-Cas9 crystal structure or as to nickases or as to functional groups;

(c) selecting from said database, using computer methods, structure(s) e.g., CRISPR-Cas9 structures that may bind to desired structures, desired structures that may bind to certain CRISPR-Cas9 structures, portions of the CRISPR-Cas9 system that may be manipulated, e.g., based on data from other portions of the CRISPR-Cas9 crystal structure and/or from Cas9 orthologs, truncated Cas9s, novel nickases or particular functional groups, or positions for attaching functional groups or functional-group-CRISPR-Cas9 systems;

(d) constructing, using computer methods, a model of the selected structure(s); and (e) outputting to said output device the selected structure(s);

and optionally synthesizing one or more of the selected structure(s);

and further optionally testing said synthesized selected structure(s) as or in a CRISPR-Cas9 system;

or, said method comprising: providing the co-ordinates of at least two atoms of the CRISPR-Cas9 crystal structure, e.g., at least two atoms of the herein Crystal Structure Table of the CRISPR-Cas9 crystal structure or co-ordinates of at least a sub-domain of the CRISPR-Cas9 crystal structure ("selected co-ordinates"), providing the structure of a candidate comprising a binding molecule or of portions of the CRISPR-Cas9 system that may be manipulated, e.g., based on data from other portions of the CRISPR-Cas9 crystal structure and/or from Cas9 orthologs, or the structure of functional groups, and fitting the structure of the candidate to the selected co-ordinates, to thereby obtain product data comprising CRISPR-Cas9 structures that may bind to desired structures, desired structures that may bind to certain CRISPR-Cas9 structures, portions of the CRISPR-Cas9 system that may be manipulated, truncated Cas9s, novel nickases, or particular functional groups, or positions for attaching functional groups or functional-group-CRISPR-Cas9 systems, with output thereof; and optionally synthesizing compound(s) from said product data and further optionally comprising testing said synthesized compound(s) as or in a CRISPR-Cas9 system.

The testing can comprise analyzing the CRISPR-Cas9 system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (eg POWERPOINT), internet, email, documentary communication such as a computer program (eg WORD) document and the like. Accordingly, the invention also comprehends computer readable media containing: atomic co-ordinate data according to the herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The computer readable media can also contain any data of the foregoing methods. The invention further comprehends methods a computer system for generating or performing rational design as in the foregoing methods containing either: atomic co-ordinate data according to herein-referenced Crystal Structure, said data defining the three dimensional structure of CRISPR-Cas9 or at least one sub-domain thereof, or structure factor data for CRISPR-Cas9, said structure factor data being derivable from the atomic coordinate data of herein-referenced Crystal Structure. The invention further comprehends a method of doing business comprising providing to a user the computer system or the media or the three dimensional structure of CRISPR-Cas9 or at least one sub-domain thereof, or structure factor data for CRISPR-Cas9, said structure set forth in and said structure factor data being derivable from the atomic co-ordinate data of herein-referenced Crystal Structure, or the herein computer media or a herein data transmission.

A "binding site" or an "active site" comprises or consists essentially of or consists of a site (such as an atom, a functional group of an amino acid residue or a plurality of such atoms and/or groups) in a binding cavity or region, which may bind to a compound such as a nucleic acid molecule, which is/are involved in binding.

By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further By "root mean square (or rms) deviation", we mean the square root of the arithmetic mean of the squares of the deviations from the mean.

By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows or Apple operating systems.

By "computer readable media", is meant any medium or media, which can be read and accessed directly or indirectly by a computer e.g., so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

In particular embodiments of the invention, the conformational variations in the crystal structures of the CRISPR-Cas9 system or of components of the CRISPR-Cas9 provide important and critical information about the flexibility or movement of protein structure regions relative to nucleotide (RNA or DNA) structure regions that may be important for CRISPR-Cas system function. The structural information provided for Cas9 (e.g., S. pyogenes Cas9) as the CRISPR enzyme in the present application may be used to further engineer and optimize the CRISPR-Cas system and this may be extrapolated to interrogate structure-function relationships in other CRISPR enzyme systems as well, e.g, other Type II CRISPR enzyme systems.

The invention comprehends optimized functional CRISPR-Cas enzyme systems. In particular the CRISPR enzyme comprises one or more mutations that converts it to a DNA binding protein to which functional domains exhibiting a function of interest may be recruited or appended or inserted or attached, in certain embodiments, the CRISPR enzyme comprises one or more mutations which include but are not limited to D10A, E762A, H840A, N854A, N863A or D986A (based on the amino acid position numbering of a S. pyogenes Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain.

The structural information provided herein allows for interrogation of sgRNA (or chimeric RNA) interaction with the target DNA and the CRISPR enzyme (e.g., Cas9) permitting engineering or alteration of sgRNA structure to optimize functionality of the entire CRISPR-Cas system. For example, loops of the sgRNA may be extended, without colliding with the Cas9 protein by the insertion of adaptor proteins that can bind to RNA. These adaptor proteins can further recruit effector proteins or fusions which comprise one or more functional domains.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

Aspects of the invention encompass a non-naturally occurring or engineered composition that may comprise a guide RNA (sgRNA) comprising a guide sequence capable of hybridizing to a target sequence in a genomic locus of interest in a cell and a CRISPR enzyme that may comprise at least one or more nuclear localization sequences, wherein the CRISPR enzyme comprises two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the CRISPR enzyme comprises two or more mutations in a residue selected from the group comprising, consisting essentially of, or consisting of D10, E762, H840, N854, N863, or D986. In a further embodiment the CRISPR enzyme comprises two or more mutations selected from the group comprising D10A, E762A, H840A, N854A, N863A or D986A. In another embodiment, the functional domain is a transcriptional activation domain, e.g., VP64. In another embodiment, the functional domain is a transcriptional repressor domain, e.g., KRAB domain, SID domain or a SID4X domain. In embodiments of the invention, the one or more heterologous functional domains have one or more activities selected from the group comprising, consisting essentially of or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ1.3, JP34, W500, KU1, M11, MX1, TW18, VK, SP, FE ID2, NL95, TW19, AP205, φCb5, φCb8r, φCh12r, φCb23r, 7s, PRR1. In another embodiment, the at least one loop of the sgRNA is tetraloop and/or loop2. An aspect of the invention emcompasses methods of modifying a genomic locus of interest to change gene expression in a cell by introducing into the cell any of the compositions decribed herein.

An aspect of the invention is that the above elements are comprised in a single composition or comprised in individual compositions. These compositions may advantageously be applied to a host to elicit a functional effect on the genomic level.

In general, the sgRNA are modified in a manner that provides specific binding sites (e.g., aptamers) for adapter proteins comprising one or more functional domains (e.g., via fusion protein) to bind to modified sgRNA are modified such that once the sgRNA forms a CRISPR complex (i.e. CRISPR enzyme binding to sgRNA and target) the adapter proteins bind and, the functional domain on the adapter protein is positioned in a spatial orientation which is advantageous for the attributed function to be effective. For example, if the functional domain is a transcription activator VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partally cleave the target.

The skilled person will understand that modifications to the sgRNA which allow for binding of the adapter+functional domain but not proper positioning of the adapter+functional domain e.g., due to steric hinderance within the three dimensional structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group comprising, consisting essentially of, or consisting of methylase activity, demethylase activity, transcription activation activity, transcription repression activity, transcription release factor activity, historic modification activity, RNA cleavage activity, DNA cleavage activity, nucleic acid binding activity, and molecular switches (e.g., light inducible). In some cases it is advantageous that additionally at least one NLS is provided. In some instances, it is advantageous to position the NLS at the N terminus. When more than one functional domain is included, the functional domains may be the same or different.

The sgRNA may be designed to include multiple binding recognition sites (e.g., aptamers) specific to the same or different adapter protein. The sgRNA may be designed to bind to the promoter region −1000−+1 nucleic acids upstream of the transcription start site (i.e. TSS), preferably −200 nucleic acids. This positioning improves functional domains which affect gene activiation (e.g., transcription activators) or gene inhibition (e.g., transcription repressors). The modified sgRNA may be one or more modified sgRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Further, the CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a Cas9 enzyme or CRISPR enzyme having advantageously about 0% of the nuclease activity of the non-mutated or wild type Cas9 enzyme or CRISPR enzyme, or no more than about 3% or about 5% or about 10% of the nuclease activity of the non-mutated or wild type Cas9 enzyme or CRISPR enzyme). This is possible by introducing mutations into the RuvC and HNH nuclease domains of the SpCas9 and orthologs thereof. For example utilizing mutations in a residue selected from the group comprising, consisting essentially of, or consisting of D10, E762, H840, N854, N863, or D986 and more preferably introducing one or more of the mutations selected from the group comprising, consisting essentially of, or consisting of D10A, E762A, H840A, N854A, N863A or D986A. A preferable pair of mutations is D10A with H840A, more preferable is D10A with N863A of SpCas9 and orthologs thereof.

The inactivated CRISPR enzyme may have associated (e.g., via fusion protein) one or more functional domains, like for example as described herein for the modified sgRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, June 2014). The adaptor protein may utlilize known linkers to attach such functional domains. In some cases it is advantageous that additionally at least one NLS is provided. In some instances, it is advantageous to position the NLS at the N terminus. When more than one functional domain is included, the functional domains may be the same or different.

In general, the positioning of the one or more functional domain on the inactivated CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partally cleave the target. This may include positions other than the N-/C-terminus of the CRISPR enzyme.

Due to crystal structure experiments, the Applicant has identified that positioning the functional domain in the Rec1 domain, the Rec2 domain, the HNH domain, or the PI domain of the SpCas9 protein or any ortholog, corresponding to these domains is advantageous. Positoning of the functional domains to the Rec1 domain or the Rec2 domain, of the SpCas9 protein or any ortholog corresponding to these domains, in some instances may be preferred. Positoning of the functional domains to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains, in some instances may be preffered. Fok1 functional domain may be attached at the N terminus. When more than one functional domain is included, the functional domains may be the same or different.

The adaptor protein may be any number of proteins that binds to an aptamer or recognition site introduced into the modified sgRNA and which allows proper positioning of one or more functional domains, once the sgRNA has been incorporated into the CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains.

Thus, the modified sgRNA, the inactivated CRISPR enzyme (with or without functional domains), and the binding protein with one or more functional domains, may each individually be comprised in a composition and administered to a host individually or collectively. Alternatively, these components may be provided in a single composition for administration to a host. Adminstration to a host may be performed via viral vectors known to the skilled person or described herein for delivery to a host (e.g., lentiviral vector, adenoviral vector, AAV vector). As explained herein, use of different selection markers (e.g., for lentiviral sgRNA selection) and concentration of sgRNA (e.g., dependent on whether multiple sgRNAs are used) may be advantageous for eliciting an improved effect.

On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals. (See, e.g., Platt et al., Cell (2014), 159(2): 440-455, or PCT patent publications cited herein, such as WO 2014/093622 (PCT/US2013/074667), which are not believed prior to the present invention or application). For example, the target cell comprises CRISRP enzyme (e.g., Cas9) conditionally or inducibly (e.g., in the form of Cre dependent constructs) and/or the adapter protein conditionally or inducibly and, on expression of a vector introduced into the target cell, the vector expresses that which induces or gives rise to the condition of CRISRP enzyme (e.g., Cas9) expression and/or adaptor expression in the target cell. By applying the teaching and compositions of the current invention with the known method of creating a CRISPR complex, inducible genomic events affected by functional domains are also an aspect of the current invention. One mere example of this is the creation of a CRISPR knock-in/conditional transgenic animal (e.g., mouse comprising e.g., a Lox-Stop-polyA-Lox (LSL) cassette) and subsequent delivery of one or more compositions providing one or more modified sgRNA (e.g., −200 nucleotides to TSS of a target gene of interest for gene activation purposes) as described herein (e.g., modified sgRNA with one or more aptamers recognized by coat proteins, e.g., MS2), one or more adapter proteins as described herein (MS2 binding protein linked to one or more VP64) and means for inducing the conditional animal (e.g., Cre recombinase for rendering Cas9 expression inducible). Alternatively, the adaptor protein may be provided as a conditional or inducible element with a conditional or inducible CRISPR enzyme to provide an effective model for screening purposes, which advantageously only requires minimal design and administration of specific sgRNAs for a broad number of applications.

The invention further comprehends a computer system for identifying one or more unique target sequences, e.g., in a genome, such as a genome of a eukaryotic organism, the system comprising: a. a memory unit configured to receive and/or store sequence information of the genome; and b. one or more processors alone or in combination programmed to perform a herein method of identifying one or more unique target sequences (e.g., locate a CRISPR motif, analyze a sequence upstream of the CRISPR motif to determine if the sequence occurs elsewhere in the genome, select the sequence if it does not occur elsewhere in the genome), to thereby identifying a unique target site and display and/or transmit the one or more unique target sequences. The candidate target sequence may be a DNA sequence. Mismatch(es) can be of RNA of the CRISPR complex and the DNA. In aspects of the invention, susceptibility of a target sequence being recognized by a CRISPR-Cas system indicates that there may be stable binding between the one or more base pairs of the target sequence and guide sequence of the CRISPR-Cas system to allow for specific recognition of the target sequence by the guide sequence.

The CRISPR/Cas or the CRISPR-Cas system utilizes a single Cas enzyme that can be programmed by a short RNA molecule to recognize a specific DNA target, in other words the Cas enzyme can be recruited to a specific DNA target using said short RNA molecule. In certain aspects, e.g., when not mutated or modified or when in a native state, the Cas or CRISPR enzyme in CRISPR/Cas or the CRISPR-Cas system, effects a cutting at a particular position; a specific DNA target. Accordingly, data can be generated—a data training set—relative to cutting by a CRISPR-Cas system at a particular position in a nucleotide, e.g., DNA, sequence at a particular position for a particular Cas or CRISPR enzyme. Similarly, data can be generated—a data training set—relative to cutting by a CRISPR-Cas system at a particular position in a nucleotide, e.g., DNA, sequence of a particular mismatch of typical nucleic acid hybridization (e.g., rather than G-C at particular position, G-T or G-U or G-A or G-G) for the particular Cas. In generating such data sets, there is the concept of average cutting frequency. The frequency by which an enzyme will cut a nucleic acid molecule, e.g., DNA, is mainly a function of the length of the sequence it is sensitive to. For instance, if an enzyme has a recognition sequence of 4 base-pairs, out of sheer probability, with 4 positions, and each position having potentially 4 different values, there are $4^4$ or 256 different possibilities for any given 4-base long strand. Therefore, theoretically (assuming completely random DNA., this enzyme will cut 1 in 256 4-base-pair long sites. For an enzyme that recognizes a sequence of 6 base-pairs, the calculation is $4^6$ or 4096 possible combinations with this length, and so such an enzyme will cut 1 in 4096 6-base-pair long sites. Of course, such calculations take into consideration only that each position has potentially 4 different values, and completely random DNA. However, DNA is not completely random; for example, the G-C content of organisms varies. Accordingly, the data training set(s) in the invention come from observing cutting by a CRISPR-Cas system at a particular position in a nucleotide, e.g., DNA, sequence at a particular position for a particular Cas or CRISPR enzyme and observing cutting by a CRISPR-Cas system at a particular position in a nucleotide, e.g., DNA, sequence of a particular mismatch of typical nucleic acid hybridization for the particular Cas, in a statistically significant number of experiments as to the particular position, the CRISPR-Cas system and the particular Cas, and averaging the results observed or obtained therefrom. The average cutting frequency may be defined as the mean of the cleavage efficiencies for all guide RNA:target DNA mismatches at a particular location.

The invention further provides a method of identifying one or more unique target sequences, e.g., in a genome, such as a genome of a eukaryotic organism, whereby the target sequence is susceptible to being recognized by a CRISPR-Cas system (and likewise, the invention also further provides a method of identifying a CRISPR-Cas system susceptible to recognizing one or more unique target sequences), wherein the method comprises: a) determining average cutting frequency at a particular position for a particular Cas from a data training set as to that Cas, b) determining average cutting frequency of a particular mismatch (e.g., guide-RNA/target mismatch) for the particular Cas from the data training set, c) multiplying the average cutting frequency at a particular position by the average cutting frequency of a particular mismatch to obtain a first product, d) repeating steps a) to c) to obtain second and further products for any further particular position (s) of mismatches and particular mismatches and multiplying those second and further products by the first product, for an ultimate product, and omitting this step if there is no mismatch at any position or if there is only one particular mismatch at one particular position (or optionally d) repeating steps to c) to obtain second and further products for any further particular position (s) of mismatches and particular mismatches and multiplying those second and further products by the first product, for an ultimate product, and omitting this step if there is no mismatch at any position or if there is only one particular mismatch at one particular position), and e) multiplying the ultimate product by the result of dividing the minimum distance between consecutive mismatches by the distance, in bp, between the first and last base of the target sequence, e.g., 15-20, such as 18, and omitting this step if there is no mismatch at any position or if there is only one particular mismatch at one particular position (or optionally e) multiplying the ultimate product by the result of dividing the minimum distance between consecutive mismatches by the distance, in bp, between the first and last base of the target sequence, e.g., 15-20, such as 18 and omitting this step if there is no mismatch at any position or if there is only one particular mismatch at one particular position), to thereby obtain a ranking, which allows for the identification of one or more unique target sequences, to thereby obtain a ranking, which allows for the identification of one or more unique target sequences. Steps (a) and (b) can be performed in either order. If there are no other products than the first product, that first product (of step (c) from multiplying (a) times (b)) is what is used to determine or obtain the ranking.

The invention also comprehends method of identifying one or more unique target sequences in a genome of a eukaryotic organism, whereby the target sequence is susceptible to being recognized by a CRISPR-Cas system, wherein the method comprises: a) creating a data training set as to a particular Cas, b) determining average cutting frequency at a particular position for the particular Cas from the data training set, c) determining average cutting frequency of a particular mismatch for the particular Cas from the data training set, d) multiplying the average cutting frequency at a particular position by the average cutting frequency of a particular mismatch to obtain a first product, e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position (or optionally e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position), and f) multiplying the ultimate product by the result of dividing the minimum distance between consecutive mismatches by 18 and omitting this step if there is no mismatch at any position or if there is only one particular mismatch at one particular position (or optionally f) multiplying the ultimate product by the result of dividing the minimum distance between consecutive mismatches by the distance, in bp, between the first and last base of the target sequence, e.g., 15-20, such as 18, and omitting this step if there is no mismatch at any position or if there is only one particular mismatch at one particular position), to thereby obtain a ranking, which allows for the identification of one or more unique target sequences. Steps (a) and (b) can be performed in either order. Steps (a) and (b) can be performed in either order. If there are no other products than the first product, that first product (of step (c) from multiplying (a) times (b)) is what is used to determine or obtain the ranking.

The invention also comprehends a method of identifying one or more unique target sequences in a genome of a eukaryotic organism, whereby the target sequence is susceptible to being recognized by a CRISPR-Cas system, wherein the method comprises: a) determining average cutting frequency of guide-RNA/target mismatches at a particular position for a particular Cas from a training data set as to that Cas, and/or b) determining average cutting frequency of a particular mismatch-type for the particular Cas from the training data set, to thereby obtain a ranking, which allows for the identification of one or more unique target sequences. The method may comprise determining both the average cutting frequency of guide-RNA/target mismatches at a particular position for a particular Cas from a training data set as to that Cas, and the average cutting frequency of a particular mismatch-type for the particular Cas from the training data set. Where both are determined, the method may further comprise multiplying the average cutting frequency at a particular position by the average cutting frequency of a particular mismatch-type to obtain a first product, repeating the determining and multiplying steps to obtain second and further products for any further particular position(s) of mismatches and particular mismatches and multiplying those second and further products by the first product, for an ultimate product, and omitting this step if there is no mismatch at any position or if there is only one particular mismatch at one particular position, and multiplying the ultimate product by the result of dividing the minimum distance between consecutive mismatches by the distance, in bp, between the first and last base of the target sequence and omitting this step if there is no mismatch at any position or if there is only one particular mismatch at one particular position, to thereby obtain a ranking, which allows for the identification of one or more unique target sequences. The distance, in bp, between the first and last base of the target sequence may be 18. The method may comprise creating a training set as to a particular Cas. The method may comprise determining the average cutting frequency of guide-RNA/target mismatches at a particular position for a particular Cas from a training data set as to that Cas, if more than one mismatch, repeating the determining step so as to determine cutting frequency for each mismatch, and multiplying frequencies of mismatches to thereby obtain a ranking, which allows for the identification of one or more unique target sequences.

The invention further comprehends a method of identifying one or more unique target sequences in a genome of a eukaryotic organism, whereby the target sequence is susceptible to being recognized by a CRISPR-Cas system, wherein the method comprises: a) determining average cutting frequency of guide-RNA/target mismatches at a particular position for a particular Cas from a training data set as to that Cas, and average cutting frequency of a particular mismatch-type for the particular Cas from the training data set, to thereby obtain a ranking, which allows for the identification of one or more unique target sequences. The invention additionally comprehends a method of identifying one or more unique target sequences in a genome of a eukaryotic organism, whereby the target sequence is susceptible to being recognized by a CRISPR-Cas system, wherein the method comprises: a) creating a training data set as to a particular Cas, b) determining average cutting frequency of guide-RNA/target mismatches at a particular position for the particular Cas from the training data set, and/or c) determining average cutting frequency of a particular mismatch-type for the particular Cas from the training data set, to thereby obtain a ranking, which allows for the identification of one or more unique target sequences. The invention yet further comprehends a method of identifying one or more unique target sequences in a genome of a eukaryotic organism, whereby the target sequence is susceptible to being recognized by a CRISPR-Cas system, wherein the method comprises: a) creating a training data set as to a particular Cas, b) determining average cutting frequency of guide-RNA/target mismatches at a particular position for the particular Cas from the training data set, and average cutting frequency of a particular mismatch-type for the particular Cas from the training data set, to thereby obtain a ranking, which allows for the identification of one or more unique target sequences. Accordingly, in these embodiments, instead of multiplying cutting-frequency averages uniquely determined for a mismatch position and mismatch type separately, the invention uses averages that are uniquely determined, e.g., cutting-frequency averages for a particular mismatch type at a particular position (thereby without multiplying these, as part of preparation of training set). These methods can be performed iteratively akin to the steps in methods including multiplication, for determination of one or more unique target sequences.

The invention in certain aspects provides a method for selecting a CRISPR complex for targeting and/or cleavage of a candidate target nucleic acid sequence within a cell, comprising the steps of: (a) determining amount, location and nature of mismatch(es) of guide sequence of potential CRISPR complex(es) and the candidate target nucleic acid sequence, (b) determining contribution of each of the amount, location and nature of mismatch(es) to hybridization free energy of binding between the target nucleic acid sequence and the guide sequence of potential CRISPR complex(es) from a training data set, (c) based on the contribution analysis of step (b), predicting cleavage at the location(s) of the mismatch(es) of the target nucleic acid sequence by the potential CRISPR complex(es), and (d) selecting the CRISPR complex from potential CRISPR complex(es) based on whether the prediction of step (c) indicates that it is more likely than not that cleavage will occur at location(s) of mismatch(es) by the CRISPR complex Step (b) may be performed by: determining local thermodynamic contributions, $\Box G_{ij}(k)$, between every guide sequence i and target nucleic acid sequence j at position k, wherein $\Box G_{ij}(k)$ is estimated from a biochemical prediction algorithm and $\Box_k$, is a position-dependent weight calculated from the training data set, estimating values of the effective free-energy $Z_{ij}$ using the relationship $p_{ij} \propto e^{-\beta Z_{ij}}$, wherein $p_{ij}$ is measured cutting frequency by guide sequence i on target nucleic acid sequence j and $\Box$ is a positive constant of proportionality, determining position-dependent weights $\Box_k$ by fining across spacer/target-pairs with the sum across all N bases of the guide-sequence $$Z_{ij} = \Sigma_{k=1}^{N} \alpha_k \Delta G_{ij}(k)$$

and wherein, step (c) is performed by determining the position-dependent weights from the effective free-energy $\vec{Z}_{est} = G\vec{a}$ between each spacer and every potential target in the genome, and determining estimated spacer-target cutting frequencies $p_{est} \propto e^{-\beta Z_{est}}$ to thereby predict cleavage. Beta is implicitly fit by fitting the values of alpha (that are completely free to be multiplied—in the process of fitting—by whichever constant is suitable for Z=sum(alpha*Delta G).

The invention also comprehends the creation of a training data set. A training data set is data of cutting frequency measurements, obtained to maximize coverage and redundancy for possible mismatch types and positions. There are advantageously two experimental paradigms for generating a training data set. In one aspect, generating a data set comprises assaying for Cas, e.g., Cas9, cleavage at a constant target and mutating guide sequences. In another aspect, generating a data set comprises assaying for Cas, e.g., Cas9, cleavage using a constant guide sequence and testing cleavage at multiple DNA targets. Further, the method can be performed in at least two ways: in vivo (in cells, tissue, or living animal) or in vitro (with a cell-free assay, using in vitro transcribed guide RNA and Cas, e.g., Cas9 protein delivered either by whole cell lysate or purified protein). Advantageously the method is performed by assaying for cleavage at a constant target with mismatched guide RNA in vivo in cell lines. Because the guide RNA may be generated in cells as a transcript from a RNA polymerase III promoter (e.g. U6) driving a DNA oligo, it may be expressed as a PCR cassette and transfect the guide RNA directly (FIG. 24c) along with CBh-driven Cas9 (PX165, FIG. 24c). By co-transfecting Cas9 and a guide RNA with one or several mismatches relative to the constant DNA target, one may assess cleavage at a constant endogenous locus by a nuclease assay such as SURVEYOR nuclease assay or next-generation deep sequencing. This data may be collected for at least one or multiple targets within a loci of interest, e.g., at least 1, at least 5, at least 10, at least 15 or at least 20 targets from the human EMX1 locus. In this manner, a data training set can be readily generated for any locus of interest. Accordingly, there are at least two ways for generating a data training set—in vivo (in cell lines or living animal) or in vitro (with a cell-free assay, using in vitro transcribed guide RNA and Cas, e.g., Cas9, protein delivered either by whole cell lysate or purified protein). Also, the experimental paradigm can differ e.g. with mutated guide sequences or with a constant guide and an oligo library of many DNA targets. These targeting experiments can be done in vitro as well. The readout would simply be running a gel on the result of the in vitro cleavage assay—the results will be cleaved and uncleaned fractions. Alternatively or additionally, these fractions can be gel-isolated and sequencing adapters can be ligated prior to deep sequencing on these populations.

The invention comprehends computer-readable medium comprising codes that, upon execution by one or more processors, implements a herein method. The invention further comprehends a computer system for performing a herein method. The system can include I a memory unit configured to receive and/or store sequence information of the genome; and II one or more processors alone or in combination programmed to perform the herein method, whereby the identification of one or more unique target sequences is advantageously displayed or transmitted. The eukaryotic organism can be selected from the group consisting of *Homo sapiens* (human), *Mus musculus* (mouse), *Rattus norvegicus* (rat), *Danio rerio* (zebrafish), *Drosophila melanogaster* (fruit fly), *Caenorhabditis elegans* (roundworm), *Sus scrofa* (pig) and *Bos taurus* (cow). The target sequence can be a DNA sequence, and the mismatch(es) can be of RNA of the CRISPR complex and the DNA.

The invention also entails a method for selecting a CRISPR complex for targeting and/or cleavage of a candidate target nucleic acid sequence, e.g., within a cell, comprising the steps of: (a) determining amount, location and nature of mismatch(es) of potential CRISPR complex(es) and the candidate target nucleic acid sequence, (b) determining the contribution of the mismatch(es) based on the amount and location of the mismatch(es), (c) based on the contribution analysis of step (b), predicting cleavage at the location(s) of the mismatch(es), and (d) selecting the CRISPR complex from potential CRISPR complex(es) based on whether the prediction of step (c) indicates that it is more likely than not that cleavage will occur at location(s) of mismatch(es) by the CRISPR complex. The cell can be from a eukaryotic organism as herein discussed. The determining steps can be based on the results or data of the data training set(s) in the invention that come from observing cutting by a CRISPR-Cas system at a particular position in a nucleotide, e.g., DNA, sequence at a particular position for a particular Cas or CRISPR enzyme and observing cutting by a CRISPR-Cas system at a particular position in a nucleotide, e.g., DNA, sequence of a particular mismatch of typical nucleic acid hybridization for the particular Cas, in a statistically significant number of experiments as to the particular position, the CRISPR-Cas system and the particular Cas, and averaging the results observed or obtained therefrom. Accordingly, for example, if the data training set shows that at a particular position the CRISPR-Cas system including a particular Cas is rather promiscuous, i.e., there can be mismatches and cutting, the amount and location may be one position, and nature of the mismatch between the CRISPR complex and the candidate target nucleic acid sequence may be not serious such that the contribution of the mismatch to failure to cut/bind may be negligible and the prediction for cleavage may be more likely than not that cleavage will occur, despite the mismatch. Accordingly, it should be clear that the data training set(s) are not generated in silico but are generated in the laboratory, e.g., are from in vitro, ex vivo and/or in vivo studies. The results from the laboratory work, e.g., from in vitro, ex vivo and/or in vivo studies, are input into computer systems for performing herein methods.

In the herein methods the candidate target sequence can be a DNA sequence, and the mismatch(es) can be of RNA of potential CRISPR complex(es) and the DNA. In aspects of the invention mentioned herein, the amount of mismatches indicates the number of mismatches in DNA: RNA base pairing between the DNA of the target sequence and the RNA of the guide sequence. In aspects of the invention the location of mismatches indicates the specific location along the sequence occupied by the mismatch and if more than one mismatch is present if the mismatches are concatenated or occur consecutively or if they are separated by at least one of more residues. In aspects of the invention the nature of mismatches indicates the nucleotide type involved in the mismatched base pairing. Base pairs are matched according to G-C and A-U Watson-Crick base pairing.

The invention further involves a method for predicting the efficiency of cleavage at candidate target nucleic acid sequence, e.g., within a target in a cell, by a CRISPR complex comprising the steps of: (a) determining amount, location and nature of mismatch(es) of the CRISPR complex and the candidate target nucleic acid sequence, (b) determining the contribution of the mismatch(es) based on the amount and location of the mismatch(es), and (c) based on the contribution analysis of step (b), predicting whether cleavage is more likely than not to occur at location(s) of mismatch(es), and thereby predicting cleavage. As with other herein methods, the candidate target sequence can be a DNA sequence, and the mismatch(es) can be of RNA of the CRISPR complex and the DNA. The cell can be from a eukaryotic organism as herein discussed.

The invention even further provides a method for selecting a candidate target sequence, e.g., within a nucleic acid sequence, e.g., in a cell, for targeting by a CRISPR complex, comprising the steps of: determining the local thermodynamic contributions, $\Box G_{ij}(k)$, between every spacer i and target j at position k, expressing an effective free-energy $Z_{ij}$ for each spacer/target-pair as the sum $$Z_{ij} = \sum_{k=1}^{N} \alpha_k \Delta G_{ij}(k)$$

wherein $\Box G_{ij}(k)$ is local thermodynamic contributions, estimated from a biochemical prediction algorithm and $\Box_k$ is position-dependent weights, and estimating effective free-energy Z through the relationship $p_{ij} \propto e^{-\beta Z_{ij}}$ wherein $p_{ij}$ is the measured cutting frequency by spacer i on target j and $\Box$ is a positive constant fit across the entire data-set, and estimating the position-dependent weights $\Box_k$ by fitting $G\vec{a} = \vec{Z}$ such that each spacer-target pair (i,j) corresponds to a row in the matrix G and each position k in the spacer-target pairing corresponds to a column in the same matrix, and estimating the effective free-energy $\overline{Z_{est}} = G\vec{a}$ between each spacer and every potential target in the genome by using the fitted values $\Box_k$, and selecting, based on calculated effective free-energy values, the candidate spacer/target pair ij according to their specificity and/or the efficiency, given the estimated spacer-target cutting frequencies $p_{est} \propto e^{-\beta Z_{est}}$. The cell can be from a eukaryotic organism as herein discussed.

The invention includes a computer-readable medium comprising codes that, upon execution by one or more processors, implements a method for selecting a CRISPR complex for targeting and/or cleavage of a candidate target nucleic acid, e.g., sequence within a cell, comprising the steps of: (a) determining amount, location and nature of mismatch(es) of potential CRISPR complex(es) and the candidate target nucleic acid sequence, (b) determining the contribution of the mismatch(es) based on the amount and location of the mismatch(es), (c) based on the contribution analysis of step (b), predicting cleavage at the location(s) of the mismatch(es), and (d) selecting the CRISPR complex from potential CRISPR complex(es) based on whether the prediction of step (c) indicates that it is more likely than not that cleavage will occur at location(s) of mismatch(es) by the CRISPR complex. The cell can be from a eukaryotic organism as herein discussed.

Also, the invention involves computer systems for selecting a CRISPR complex for targeting and/or cleavage of a candidate target nucleic acid sequence, e.g., within a cell, the system comprising: a. a memory unit configured to receive and/or store sequence information of the candidate target nucleic acid sequence; and b. one or more processors alone or in combination programmed to (a) determine amount, location and nature of mismatch(es) of potential CRISPR complex(es) and the candidate target nucleic acid sequence, (b) determine the contribution of the mismatch(es) based on the amount and location of the mismatch(es), (c) based on the contribution analysis of step (b), predicting cleavage at the location(s) of the mismatch(es), and (d) select the CRISPR complex from potential CRISPR complex(es) based on whether the prediction of step (c) indicates that it is more likely than not that cleavage will occur at location(s) of mismatch(es) by the CRISPR complex. The cell can be from a eukaryotic organism as herein discussed. The system can display or transmit the selection.

In aspects of the invention mentioned herein, the amount of mismatches indicates the number of mismatches in DNA: RNA base pairing between the DNA of the target sequence and the RNA of the guide sequence. In aspects of the invention the location of mismatches indicates the specific location along the sequence occupied by the mismatch and if more than one mismatch is present if the mismatches are concatenated or occur consecutively or if they are separated by at least one of more residues. In aspects of the invention the nature of mismatches indicates the nucleotide type involved in the mismatched base pairing. Base pairs are matched according to G-C and A-U Watson-Crick base pairing.

Accordingly, aspects of the invention relate to methods and compositions used to determine the specificity of Cas9. In one aspect the position and number of mismatches in the guide RNA is tested against cleavage efficiency. This information enables the design of target sequences that have minimal off-target effects.

The invention also comprehends a method of identifying one or more unique target sequences in a genome of a eukaryotic organism, whereby the target sequence is susceptible to being recognized by a CRISPR-Cas system, wherein the method comprises a) determining average cutting frequency of guide-RNA/target mismatches at a particular position for a particular Cas from a training data set as to that Cas, and if more than one mismatch is present then step a) is repeated so as to determine cutting frequency for each mismatch after which frequencies of mismatches are multiplied to thereby obtain a ranking, which allows for the identification of one or more unique target sequences. The invention further comprehends a method of identifying one or more unique target sequences in a genome of a eukaryotic organism, whereby the target sequence is susceptible to being recognized by a CRISPR-Cas system, wherein the method comprises a) creating a training data set as to a particular Cas, b) determining average cutting frequency of guide-RNA/target mismatches at a particular position for a particular Cas from the training data set, if more than one mismatch exists, repeat step b) so as to determine cutting frequency for each mismatch, then multiply frequencies of mismatches to thereby obtain a ranking, which allows for the identification of one or more unique target sequences. The invention also relates to computer systems and computer readable media that executes these methods.

In various aspects, the invention involves a computer system for selecting a candidate target sequence within a nucleic acid sequence or for selecting a Cas for a candidate target sequence, e.g., selecting a target in a eukaryotic cell for targeting by a CRISPR complex.

The computer system may comprise: (a) a memory unit configured to receive and/or store said nucleic acid sequence; and (b) one or more processors alone or in combination programmed to perform as herein discussed. For example, programmed to: (i) locate a CRISPR motif sequence (e.g., PAM) within said nucleic acid sequence, and (ii) select a sequence adjacent to said located. CRISPR motif sequence (e.g. PAM) as the candidate target sequence to which the CRISPR complex binds. In some embodiments, said locating step may comprise identifying a CRISPR motif sequence (e.g. PAM) located less than about 10000 nucleotides away from said target sequence, such as less than about 5000, 2500, 1000, 500, 250, 100, 50, 25, or fewer nucleotides away from the target sequence. In some embodiments, the candidate target sequence is at least 10, 15, 20, 25, 30, or more nucleotides in length. In some embodiments the candidate target sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, the nucleotide at the 3' end of the candidate target sequence is located no more than about 10 nucleotides upstream of the CRISPR motif sequence (e.g. PAM), such as no more than 5, 3, 2, or 1 nucleotides. In some embodiments, the nucleic acid sequence in the eukaryotic cell is endogenous to the cell or organism, e.g., eukaryotic genome. In some embodiments, the nucleic acid sequence in the eukaryotic cell is exogenous to the cell or organism, e.g., eukaryotic genome.

In various aspects, the invention provides a computer-readable medium comprising codes that, upon execution by one or more processors, implements a method described herein, e.g., of selecting a candidate target sequence within a nucleic acid sequence or selecting a CRISPR candidate for a target sequence; for instance, a target sequence in a cell such as in a eukaryotic cell for targeting by a CRISPR complex. The method can comprise: (i) locate a CRISPR motif sequence (e.g., PAM) within said nucleic acid sequence, and (ii) select a sequence adjacent to said located CRISPR motif sequence (e.g. PAM) as the candidate target sequence to which the CRISPR complex binds. In some embodiments, said locating step may comprise identifying a CRISPR motif sequence (e.g. PAM) located less than about 10000 nucleotides away from said target sequence, such as less than about 5000, 2500, 1000, 500, 250, 100, 50, 25, or fewer nucleotides away from the target sequence. In some embodiments, the candidate target sequence is at least 10, 15, 20, 25, 30, or more nucleotides in length. In some embodiments the candidate target sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, the nucleotide at the 3' end of the candidate target sequence is located no more than about 10 nucleotides upstream of the CRISPR motif sequence PAM), such as no more than 5, 4, 3, 2, or 1 nucleotides. In some embodiments, the nucleic acid sequence in the eukaryotic cell is endogenous to the cell or organism, e.g., eukaryotic genome. In some embodiments, the nucleic acid sequence in the eukaryotic cell is exogenous to the cell or organism, e.g., eukaryotic genome.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device comprising a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

Accordingly, it is an object of the invention not to encompass within the invention any previously known product, process of making the product, or method of using the product such that Applicants reserve the fight and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 8(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed. Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A-5D: DNA Insertion Method (insert and library preparation elements): (a) ex.1.1: DNA insert composed of one or more priming sites; ex.1.2: DNA insert composed of an event barcode (EBC) and priming sites for bi-directional non-restrictive linear amplification (P1a, P1b) and exponential amplification (P2a, P2b); ex 1.3: single stranded DNA insert containing a partial double stranded region; ex. 1.4 DNA insert containing tagged nucleotides or defined nucleotide sequence for affinity purification; ex. 1.5 DNA insert containing typeIIS nuclease sites at insert ends. b) ssDNA ligation handle containing a ligation barcode (LBC) and priming site (P3) for exponential amplification; Y ligation adapter composed of LBS and handle sequences. (c) Events (indel, translocation, large insertion or deletion) are captured by the ligation of a DNA insert at a pair of free DNA ends. (d) Optionally, a genomic insert event propogation.

FIGS. 6A-6D: DNA Insertion Method (nrLAM library preparation): (a) Insert capture event. (b) Genomic events are propagated by cell growth, and cell populations containing insertion events are split prior to non-restrictive linear amplification (nrLAM). A single biotinylated primer (P1a or P1b) generates a single-stranded template containing the insert and flanking genomic sequence. (c) Affinity capture is used to separate nrLAM products from genomic DNA, and ligation handles are added to the ends of nrLAM products, followed by exponential amplification and sequencing. (d) Junction consisting of P2a and P2b amplicons with matching EBC.

FIGS. 7A-7D: DNA Insertion Method (genomic DNA fragmentation library preparation): (a) Insert capture events (top: DNA insert containing no affinity tagged nucleotides; bottom: DNA insert containing tagged nucleotides). (b) DNA inserts are excised from genomic DNA by either whole-genome fragmentation or type IIS endonuclease digestion (type IIS insert). (c) Following genomic DNA fragmentation, DNA inserts and flanking genomic sequence are captured by affinity purification based on oligo-bait (I, ex. 1) or tagged nucleotide capture (i, ex. 2) to remove genomic DNA fragments without inserts present. Affinity purified fragments are subjected to end repair and a-tailing (ii) followed by ligation of y-adapters for NGS sequencing (iii). Amplicons are then enriched by PCR prior to next generation sequencing (iii). (d) Sequencing can be performed by outside-in or inside-out read priming, or a combination of the two approaches can be used. These strategies enable application specific minimization of read lengths for sequencing of insert barcodes (EBCs), ligation barcodes (LBCs), and genomic sequence flanking both sides of the insert.

FIG. 17 depicts depicts an example of a primer (SEQ ID NO: 68) for linear amplication. The primer comprises a T7 promoter for transcription of adjacent sequences, and RAS sequence, a unique molecular identifier (UMI), and a barcode for high throughput sequencing.

FIG. 22 discloses SEQ ID NOS 69-73, respectively, in order of appearance.

FIG. 23 discloses SEQ ID NOS 52, 62, 53, 57, 55, 54, 58, 65, 74, 56, 61, 59, 75, 76, and 77, respectively, in order of appearance.

FIG. 24 indicates some of the advantageous improvements associated with BLISS.

Figure 1:
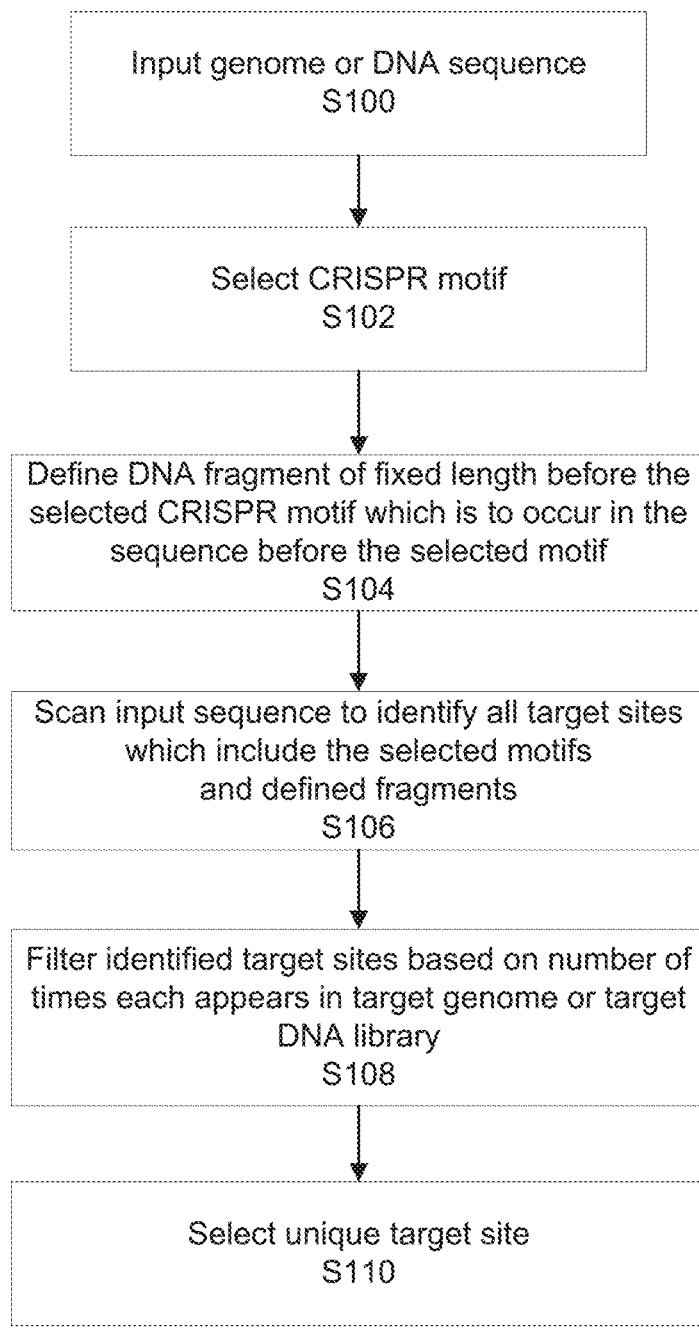
FIG. 1 shows a flow diagram as to locational methods of the invention.

The figures herein are for illustrative purposes only and are not necessarily drawn to scale.

DETAILED DESCRIPTION OF THE INVENTION

The figures herein are for illustrative purposes only and are not necessarily drawn to scale.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algotithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraftcom), ELAND (Illumina, San Diego, Calif.), SOAP (available at soap.genomics.org.cn) and Maq (available at maq.source-forge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMMNNNNNNNNNNNNXGG (SEQ ID NO: 1) where NNNNNNNNNNNNXGG (SEQ ID NO: 2) (N is A, G, T, or C; and X can be anything) has a single occurrence in the genome. A unique target sequence in a genome may include an S. pyogenes Cas9 target site of the form MMMMMMMMMNNNNNNNNNNNXGG (SEQ ID NO: 3) where NNNNNNNXGG (SEQ ID NO: 4) (N is A, G, T, or C; and X can be anything) has a single occurrence in the genome. For the S. thermophilus CRISPR1 Cas9, a unique target sequence in a genome may include a Cas9 target site of the form MMMMMM-MMNNNNNNNNNNNNXXAGAAW (SEQ ID NO: 5) where NNNNNNNNNNNNXXAGAAW (SEQ ID NO: 6) (N is A, G, T, or C; X can be anything; and W is A or T) has a single occurrence in the genome. A unique target sequence in a genome may include an S. thermophilus CRISPR1 Cas9 target site of the form MMMMMM-MMNNNNNNNNNNNNXXAGAAW (SEQ ID NO: 7) where NNNNNNNNNNNXXAGAAW (SEQ ID NO: 8) (N is A, G, T, or C; X can be anything; and W is A or T) has a single occurrence in the genome. For the S. pyogenes Cas9, a unique target sequence in a genome may include a Cas9 target site of the form MMMMMM-MMNNNNNNNNNNNNXGGXG (SEQ ID NO: 9) where NNNNNNNNNNNNXGGXG(SEQ ID NO: 10) (N is A, G, T, or C; and X can be anything) has a single occurrence in the genome. A unique target sequence in a genome may include an S. pyogenes Cas9 target site of the form MMM-MMMMMMNNNNNNNNNNXGGXG (SEQ ID NO: 11) where NNNNNNNNNNNXGGXG (SEQ ID NO: 12) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

Further embodiments of the invention relate to algorithms that lay the foundation of methods relating to CRISPR enzyme, e.g. Cas, specificity or off-target activity. In general, algorithms refer to an effective method expressed as a finite list of well defined instructions for calculating one or more functions of interest. Algorithms may be expressed in several kinds of notation, including but not limited to programming languages, flow charts, control tables, natural languages, mathematical formula and pseudocode. In a preferred embodiment, the algorithm may be expressed in a programming language that expresses the algorithm in a form that may be executed by a computer or a computer system.

Methods relating to CRISPR enzyme, e.g. Cas, specificity or off-target activity are based on algorithms that include but are not limited to the thermodynamic algorithm, multiplicative algorithm and positional algorithm. These algorithms take in an input of a sequence of interest and identify candidate target sequences to then provide an output of a ranking of candidate target sequences or a score associated with a particular target sequence based on predicted off-target sites. Candidate target sites may be selected by an end user or a customer based on considerations which include but are not limited to modification efficiency, number, or location of predicted off-target cleavage. In a more preferred embodiment, a candidate target site is unique or has minimal predicted off-target cleavage given the previous parameters. However, the functional relevance of potential off-target modification should also be considered when choosing a target site. In particular, an end user or a customer may consider whether the off-target sites occur within loci of known genetic function, i.e. protein-coding exons, enhancer regions, or intergenic regulatory elements. There may also be cell-type specific considerations, i.e. if an off-target site occurs in a locus that is not functionally relevant in the target cell type. Taken together, a end user or customer may then make an informed, application-specific selection of a candidate target site with minimal off-target modification.

The thermodynamic algorithm may be applied in selecting a CRISPR complex for targeting and/or cleavage of a candidate target nucleic acid sequence within a cell. The first step is to input the target sequence (Step S400) which may have been determined using the positional algorithm. A CRISPR complex is also input (Step S402). The next step is to compare the target sequence with the guide sequence for the CRISPR complex (Step S404) to identify any mismatches. Furthermore, the amount, location and nature of the mismatch(es) between the guide sequence of the potential CRISPR complex and the candidate target nucleic acid sequence may be determined. The hybridization free energy of binding between the target sequence and the guide sequence is then calculated (Step S406). For example, this may be calculated by determining a contribution of each of the amount, location and nature of mismatch(es) to the hybridization free energy of binding between the target nucleic acid sequence and the guide sequence of potential CRISPR complex(es). Furthermore, this may be calculated by applying a model calculated using a training data set as explained in more detail below. Based on the hybridization free energy (i.e. based on the contribution analysis) a prediction of the likelihood of cleavage at the location(s) of the mismatch(es) of the target nucleic acid sequence by the potential CRISPR complex(es) is generated (Step S408). The system then determines whether or not there are any additional CRISPR complexes to consider and if so repeats the comparing, calculating and predicting steps. Each CRISPR complex is selected from the potential CRISPR complex(es) based on whether the prediction indicates that it is more likely than not that cleavage will occur at location(s) of mismatch(es) by the CRISPR complex (Step S410). Optionally, the probabilities of cleavage may be ranked so that a unique CRISPR complex is selected. Determining the contribution of each of the amount, location and nature of mismatch(es) to hybridization free energy includes but is not limited to determining the relative contribution of these factors. The term "location" as used in the term "location of mismatch(es)" may refer to the actual location of the one or more base pair mismatch(es) but may also include the location of a stretch of base pairs that flank the base pair mismatch(es) or a range of locations/positions. The stretch of base pairs that flank the base pair mismatch(es) may include but are not limited to at least one, at least two, at least three base pairs, at least four or at least five or more base pairs on either side of the one or more mismatch(es). As used herein, the "hybridization free energy" may be an estimation of the free energy of binding, e.g. DNA:RNA free energy of binding which may be estimated from data on DNA:DNA free energy of binding and RNA:RNA free energy of binding.

In methods relating to the multiplicative algorithm applied in identifying one or more unique target sequences in a genome of a eukaryotic organism, whereby the target sequence is susceptible to being recognized by a CRISPR-Cas system, wherein the method comprises: a) creating a data training set as to a particular Cas, b) determining average cutting frequency at a particular position for the particular Cas from the data training set, c) determining average cutting frequency of a particular mismatch for the particular Cas from the data training set, d) multiplying the average cutting frequency at a particular position by the average cutting frequency of a particular mismatch to obtain a first product, e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position (or optionally e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position), and f) multiplying the ultimate product by the result of dividing the minimum distance between consecutive mismatches by 18 and omitting this step if there is no mismatch at any position or if there is only one particular mismatch at one particular position (or optionally f) multiplying the ultimate product by the result of dividing the minimum distance between consecutive mismatches by 18 and omitting this step if there is no mismatch at any position or if there is only one particular mismatch at one particular position), to thereby obtain a ranking, which allows for the identification of one or more unique target sequences, the predicted cutting frequencies for genome-wide targets may be calculated by multiplying, in series: $f_{est}=f(1)g(N_1, N_1')\times$ f(2)g(N$_2$, N$_2$')× ... f(19)g(N$_{19}$, N$_{19}$')×h with values f(i) and g(N$_i$, N$_i$') at position i corresponding, respectively, to the aggregate position- and base-mismatch cutting frequencies for positions and pairings indicated in a generalized base transition matrix or an aggregate matrix, e.g. a matrix as indicated in FIG. 12c. Each frequency was normalized to range from 0 to 1, such that f→(f−f$_{min}$)/(f$_{max}$−f$_{min}$). In case of a match, both were set equal to 1. The value h meanwhile re-weighted the estimated frequency by the minimum pair-wise distance between consecutive mismatches in the target sequence. This value distance, in base-pairs, was divided by 18 to give a maximum value of 1 (in cases where fewer than 2 mismatches existed, or where mismatches occurred on opposite ends of the 19 bp target-window). Samples having a read-count of at least 10,000 (n=43) were plotted. Those tied in rank were given a rank-average. The Spearman correlation coefficient, 0.58, indicated that the estimated frequencies recapitulated 58% of the rank-variance for the observed cutting frequencies. Comparing f$_{est}$ with the cutting frequencies directly yielded a Pearson correlation of 0.89. While dominated by the highest-frequency gRNA/target pairs, this value indicated that nearly 90% of all cutting-frequency variance was explained by the predictions above. In further aspects of the invention, the multiplicative algorithm or the methods mentioned herein may also include thermodynamic factors, e.g. hybridization energies, or other factors of interest being multiplied in series to arrive at the ultimate product.

In embodiments of the invention, determining the off-target activity of a CRISPR enzyme may allow an end user or a customer to predict the best cutting sites in a genomic locus of interest. In a further embodiment of the invention, one may obtain a ranking of cutting frequencies at various putative off-target sites to verify in vitro, in vivo or ex vivo if one or more of the worst case scenario of non-specific cutting does or does not occur. In another embodiment of the invention, the determination of off-target activity may assist with selection of specific sites if an end user or customer is interested in maximizing the difference between on-target cutting frequency and the highest cutting frequency obtained in the ranking of off-target sites. Another aspect of selection includes reviewing the ranking of sites and indentifying the genetic loci of the non-specific targets to ensure that a specific target site selected has the appropriate difference in cutting frequency from say targets that may encode for oncogenes or other genetic loci of interest. Aspects of the invention may include methods of minimizing therapeutic risk by verifying the off-target activity of the CRISPR-Cas complex. Further aspects of the invention may include utilizing information on off-target activity of the CRISPR-Cas complex to create specific model systems (e.g. mouse) and cell lines. The methods of the invention allow for rapid analysis of non-specific effects and may increase the efficiency of a laboratory.

Figure 23:
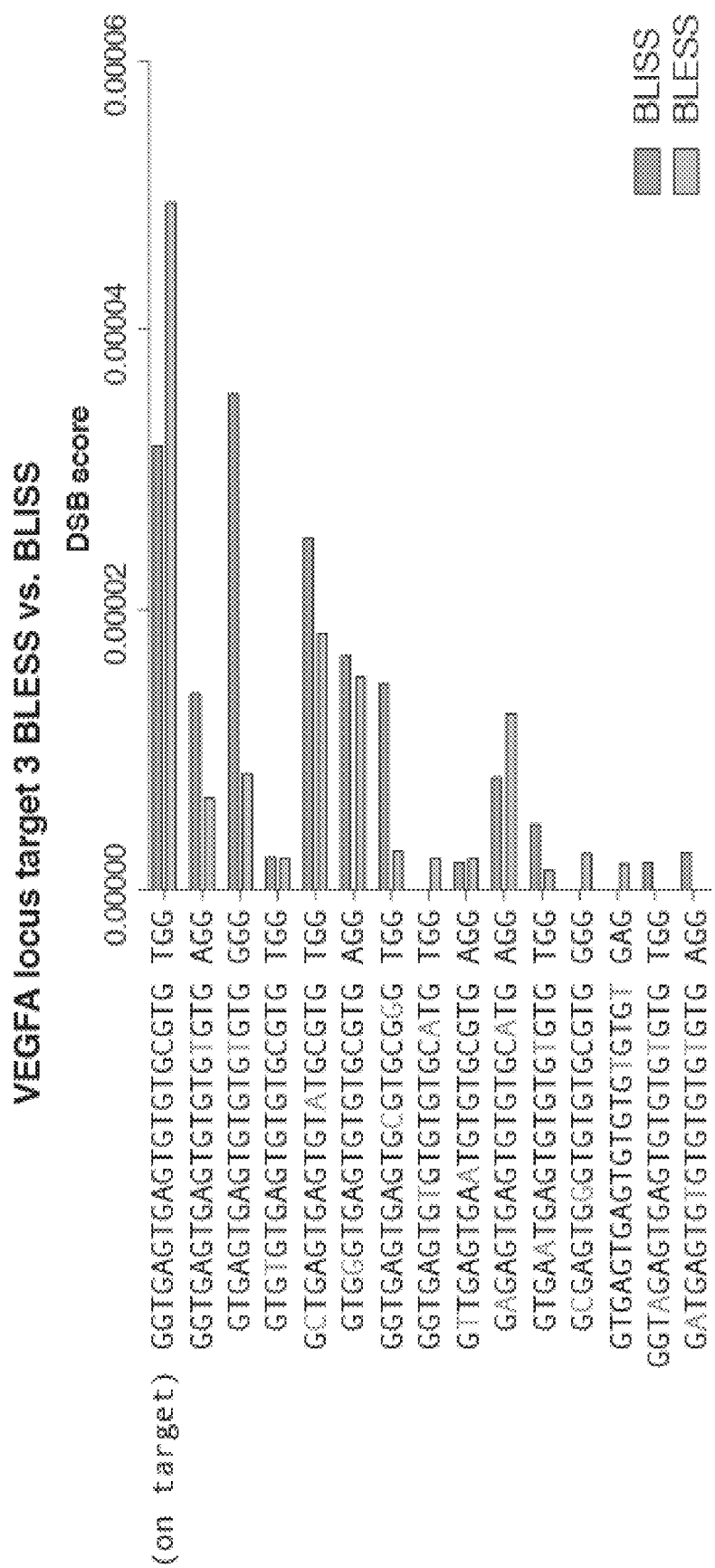
FIG. 23 depicts an analysis of BLESS vs. BLISS for unbiased off target analysis for the VEGFA locus. The BLESS samples had 5.8M reads while the BLISS samples used 2.9M reads. Both samples reflect 2 bioreplicates. The analysis was done using the CRISPR-BLESS analysis pipeline described herein and in Ran et al., 2015.

In methods relating to the positional algorithm applied in identifying one or more unique target sequences in a genome of a eukaryotic organism, whereby the target sequence is susceptible to being recognized by a CRISPR-Cas system, wherein the method comprises: a) determining average cutting frequency of guide-RNA/target mismatches at a particular position for a particular Cas from a training data set as to that Cas, if more than one mismatch, repeat step a) so as to determine cutting frequency for each mismatch, multiply frequencies of mismatches to thereby obtain a ranking, which allows for the identification of one or more unique target sequences, an example of an application of this algorithm may be seen in FIG. 23.

FIGS. 1, 2A, 3B and 4, respectively, each show a flow diagram of methods of the invention. FIG. 1 provides a flow diagram as to locational or positional methods of the invention, i.e., with respect to computational identification of unique CRISPR target sites: To identify unique target sites for a Cas, e.g., a Cas9, e.g., the S. pyogenes SF370 Cas9 (SpCas9) enzyme, in nucleic acid molecules, e.g., of cells, e.g., of organisms, which include but are not limited to human, mouse, rat, zebrafish, fruit fly, and C. elegans genome, Applicants developed a software package to scan both strands of a DNA sequence and identify all possible SpCas9 target sites. The method is shown in FIG. 1 which shows that the first step is to input the genome sequence (Step S100). The CRISPR motif(s) which are suitable for this genome sequence are then selected (Step S102). For this example, the CRISPR motif is an NGG protospacer adjacent motif (PAM) sequence. A fragment of fixed length which needs to occur in the overall sequence before the selected motif (i.e. upstream in the sequence) is then selected (Step S102). In this case, the fragment is a 20 bp sequence. Thus, each SpCas9 target site was is operationally defined as a 20 bp sequence followed by an NGG protospacer adjacent motif (PAM) sequence, and all sequences satisfying this 5'-N20-NGG-3' definition on all chromosomes were identified (Step S106). To prevent non-specific genome editing, after identifying all potential sites, all target sites were filtered based on the number of times they appear in the relevant reference genome (Step S108), (Essentially, all the 20-bp fragments (candidate target sites) upstream of the NGG PAM motif are aggregated. If a particular 20-bp fragment occurs more than once in your genome-wide search, it is considered not unique and 'strikes out', aka filtered. The 20-bp fragments that REMAIN therefore occur only once in the target genome, making it unique; and, instead of taking a 20-bp fragment (the full Cas9 target site), this algorithm takes the first, for example, 11-12 bp upstream of the PAM motif and requires that to be unique.) Finally, a unique target site is selected (Step S110), e.g. To take advantage of sequence specificity of Cas, e.g., Cas9 activity conferred by a 'seed' sequence, which can be, for example, approximately 11-12 bp sequence 5' from the PAM sequence, 5'-NNNNNNNNNN-NGG-3' sequences were selected to be unique in the relevant genome. Genomic sequences are available on the UCSC Genome Browser and sample visualizations of the information for the Human genome hg, Mouse genome mm, Rat genome rn, Zebrafish genome danRer, D. melanogaster genome dm, C. elegans genome ce, the pig genome and cow genome are shown in FIGS. 15 through 22 respectively.

Figure 2A:
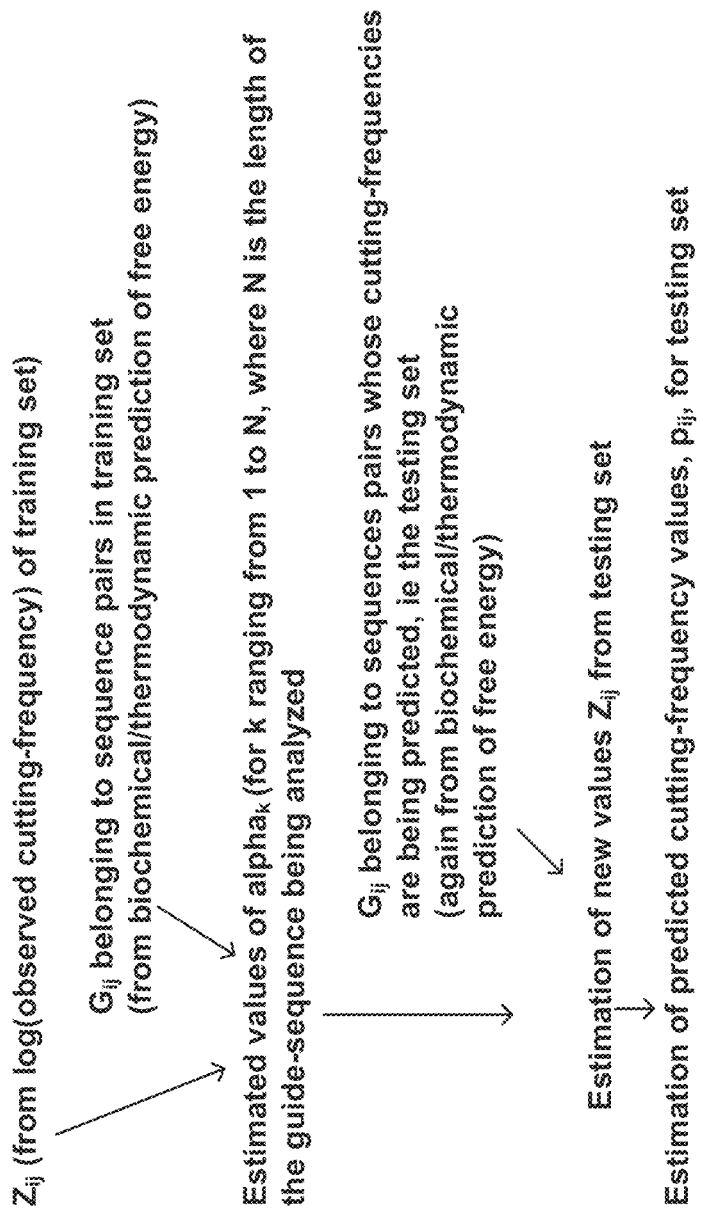
FIGS. 2A-2B show a flow diagram as to thermodynamic methods of the invention.
Figure 2B:
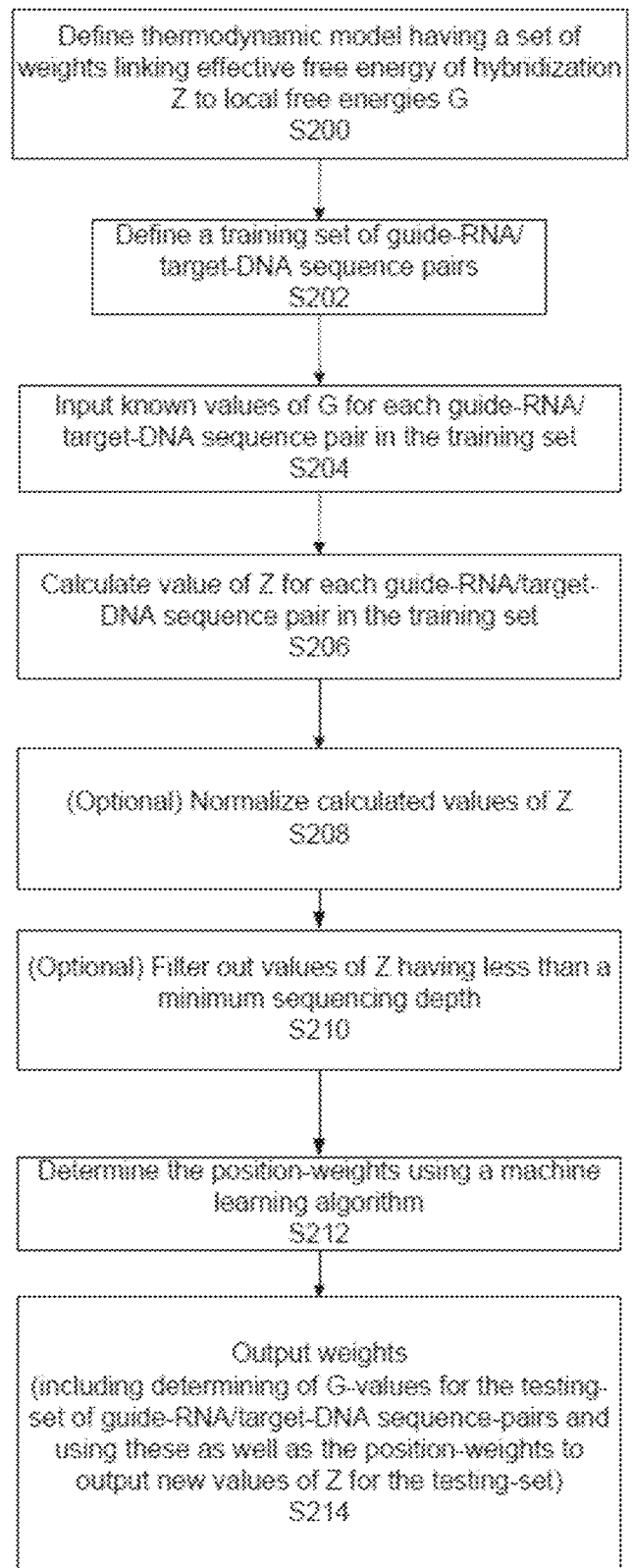
Figure 3:
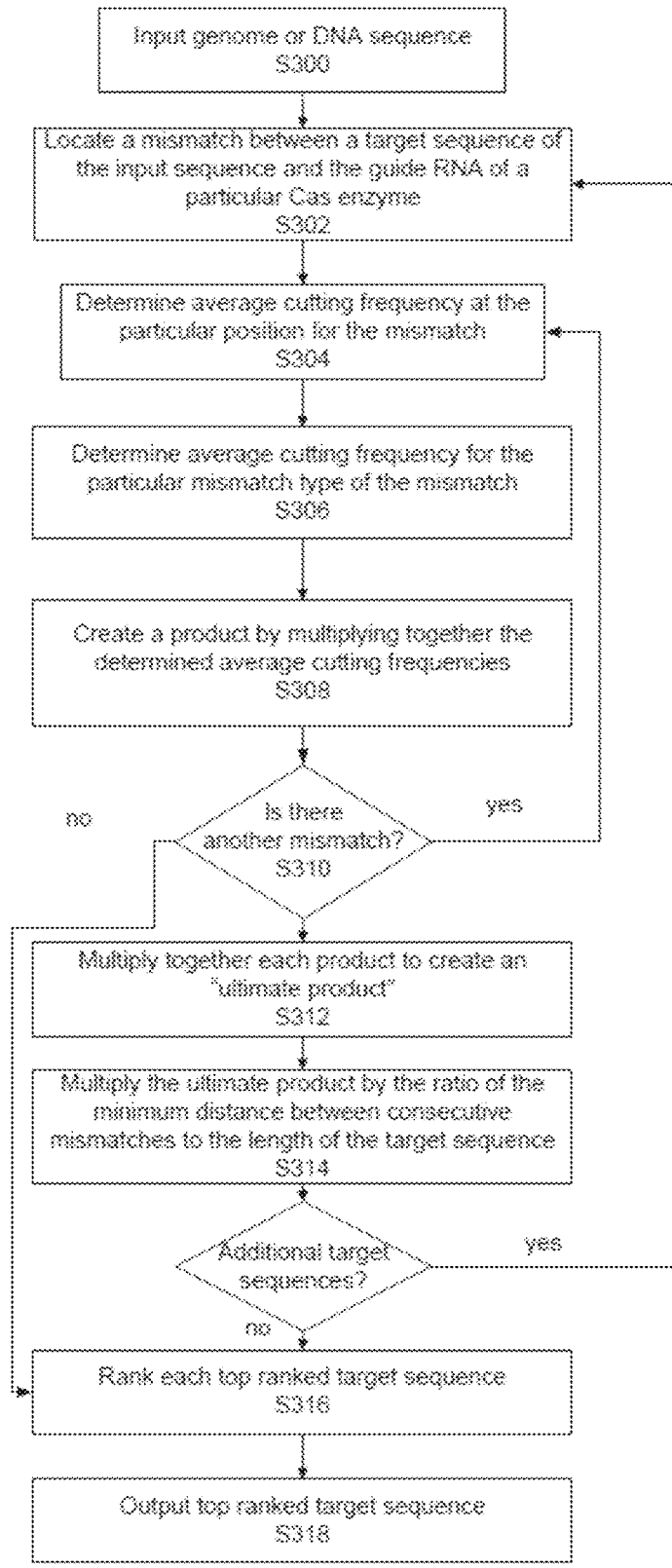
FIG. 3 shows a flow diagram as to multiplication methods of the invention.

FIGS. 2A and 2B each provides a flow diagram as to thermodynamic methods of the invention. FIG. 3 provides a flow diagram as to multiplication methods of the invention. Referring to FIGS. 2A and 2B, and considering the least squares thermodynamic model of CRISPR-Cas cutting efficiency, for arbitrary Cas9 target sites, Applicants generated a numerical thermodynamic model that predicts Cas9 cutting efficiency. Applicants propose 1) that the Cas9 guide RNA has specific free energies of hybridization to its target and any off-target DNA sequences and 2) that Cas9 modifies RNA:DNA hybridization free-energies locally in a position-dependent but sequence-independent way. Applicants trained a model for predicting CRISPR-Cas cutting efficiency based on their CRISPR-Cas guide RNA mutation data and RNA:DNA thermodynamic free energy calculations using a machine learning algorithm. Applicants then validated their resulting models by comparing their predictions of CRISPR-Cas off-target cutting at multiple genomic loci with experimental data assessing locus modification at the same sites. The methodology adopted in developing this algorithm is as follows: The problem summary states that for arbitrary spacers and targets of constant length, a numerical model that makes thermodynamic sense and predicts Cas9 cutting efficiency is to be found. Suppose Cas9 modifies DNA:RNA hybridization free-energies locally in a position-dependent but sequence-independent way. The first step is to define a model having a set a weights which links the free energy of hybridization Z with the local free energies G (Step S200). Then for DNA:RNA hybridization free-energies $\Delta G_{ij}(k)$ (for position k between 1 and N) of spacer i and target j $$Z_{ij} = \sum_{k=1}^{N} \alpha_k \Delta G_{ij}(k)$$

$Z_{ij}$ can be treated as an "effective" free-energy modified by the multiplicative position-weights $\alpha_k$. The "effective" free-energy $Z_{ij}$ corresponds to an associated cutting-probability $\sim e^{-\beta Z_{ij}}$ (for some constant $\beta$) in the same way that an equilibrium model of hybridization (without position-weighting) would have predicted a hybridization-probability $\sim e^{-\beta \Delta G_{ij}}$. Since cutting-efficiency has been measured, the values $Z_{ij}$ can be treated as their observables. Meanwhile, $\Delta G_{ij}(k)$ can be calculated for any experiment's spacer-target pairing. Applicants task was to find the values $\alpha_k$, since this would allow them to estimate $Z_{ij}$ for any spacer-target pair. The weights are determined by inputting known values for Z and G from a training set of sequences with the known values being determined by experimentation as necessary. Thus, Applicants need to define a training set of sequences (Step S202) and calculate a value of Z for each sequence in the training set (Step S204). Writing the above equation for in matrix form Applicants get:

$$\vec{Z} = G\vec{\alpha} \qquad (1)$$

Figure 10:
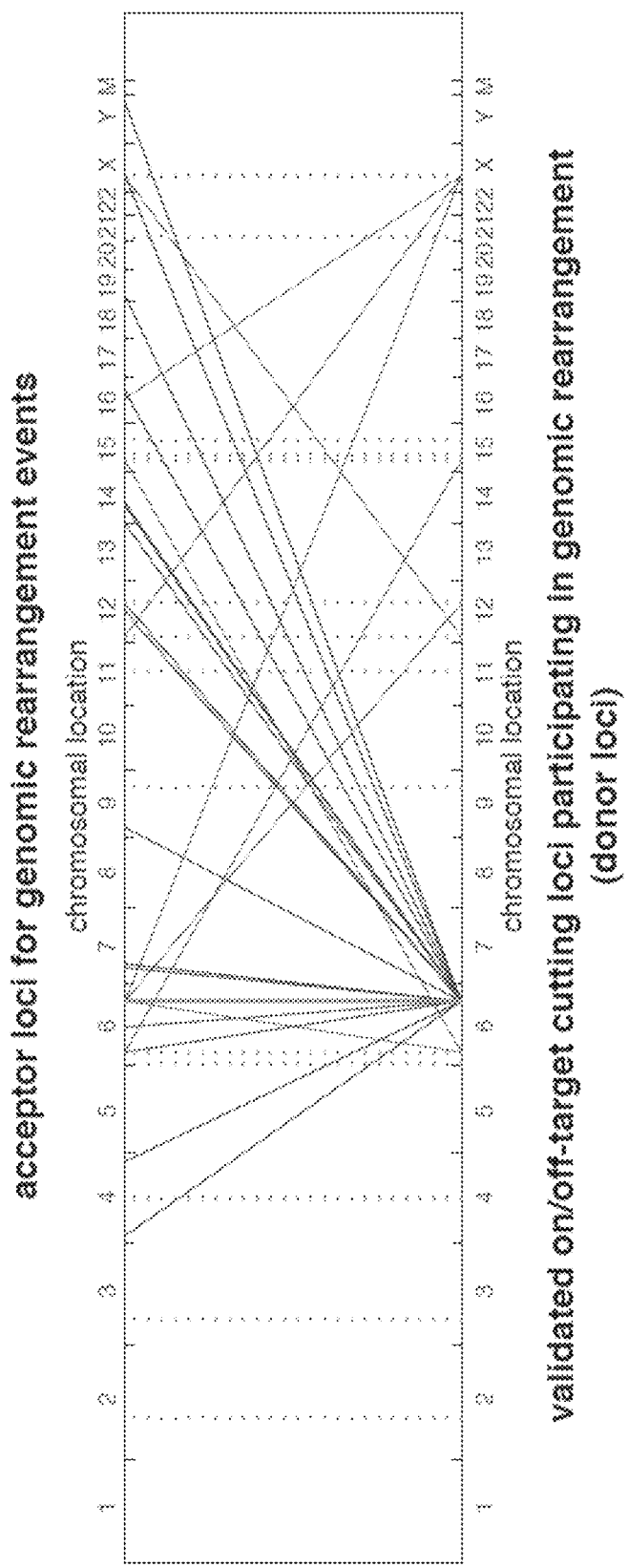
FIG. 10: VEGFA3 Genomic Rearrangement Mappings: Detected mappings of genomic rearrangement events (long deletions, translocations) from validated VEGFA3 on-target and off-target loci (lower nodes) to junction loci (upper nodes).
Figure 11:
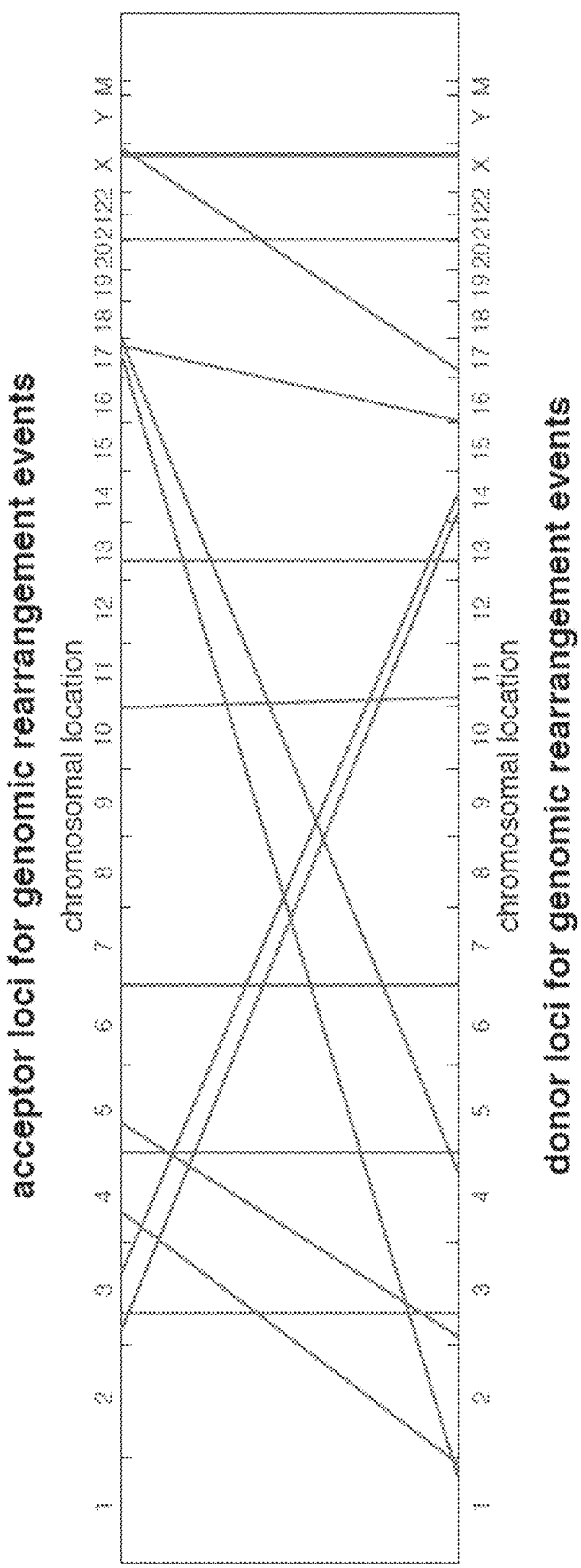
FIG. 11: Baseline Genomic Rearrangement Mappings: Detected mappings of genomic rearrangement events (long deletions, translocations) from donor loci (lower nodes) to acceptor loci (upper nodes) in cells containing only insert.
Figure 12:
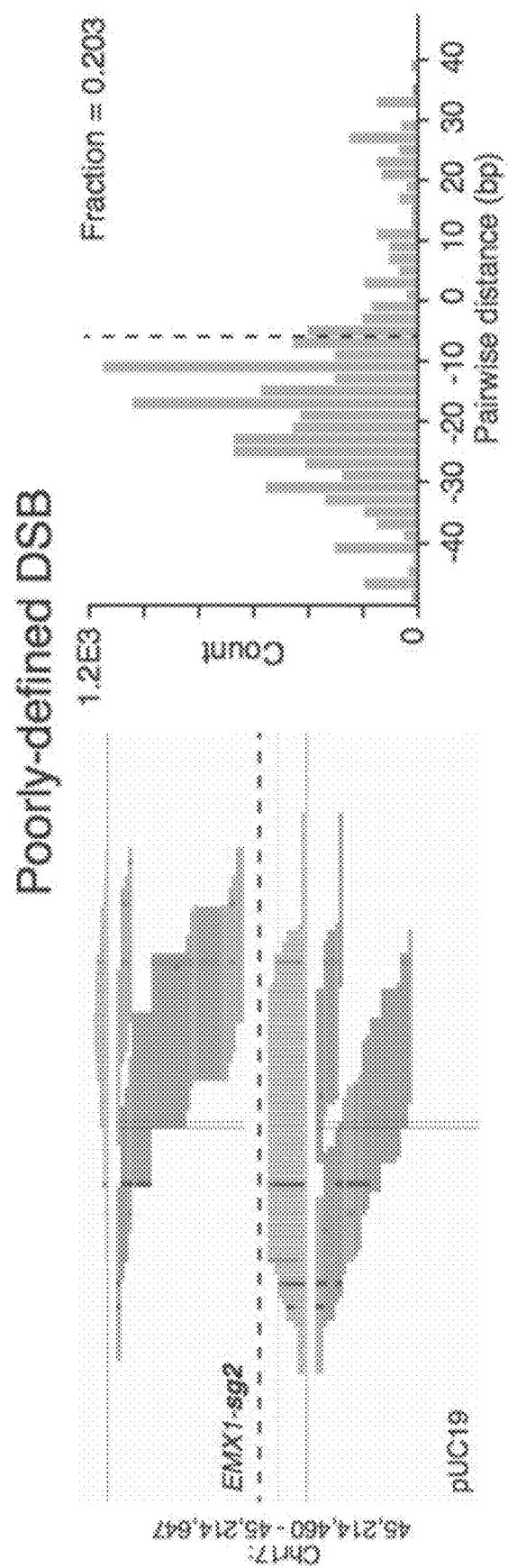
FIG. 12 depicts a pooly defined DSB site. Representative sequence read mappings (left) and corresponding histograms of the pairwise distances between all forward orientation (red) reads and reverse orientation (blue) reads (right) are shown. Individual DSBs mapped from a collection of cells show a broad range of break points.

The least-squares estimate is then $$\vec{\alpha}_{est} = (G^T G)^{-1} G^T \vec{Z}$$

where $G^1$ is the matrix-transpose of the G and $(G^T G)^{-1}$ is the inverse of their matrix-product. In the above G is a matrix of local DNA:RNA free-energy values whose rth row corresponds to experimental trial r and whose kth column corresponds to the kth position in the DNA:RNA hybrid tested in that experimental trial. These values of G are thus input into the training system (Step S204). $\vec{Z}$ is meanwhile a column-vector whose rth row corresponds to observables from the same experimental trial as G's rth row. Because of the relation described above wherein the CRISPR cutting frequencies are estimated to vary as $\sim e^{-\beta Z_{ij}}$, these observables, $Z_{ij}$, were calculated as the natural logarithm of the observed cutting frequency. The observable is the cleavage efficiency of Cas, e.g., Cas9, at a target DNA for a particular guide RNA and target DNA pair. The experiment is Cas, e.g., Cas9, with a particular sgRNA/DNA target pairing, and the observable is the cleavage percentage (whether measured as indel formation percentage from cells or simply cleavage percentage in vitro) (see herein discussion on generating training data set). More in particular, every unique PCR reaction that was sequenced should be treated as a unique experimental trial to encompass replicability within the vector. This means that experimental replicates each go into separate rows of equation 1 (and because of this, some rows of G will be identical). The advantage of this is that when $\vec{\alpha}$ is fit, all relevant information—including replicability—is taken into account in the final estimate. Observable $\vec{Z}$, values were calculated as log (observed frequency of cutting) (Step S206). Cutting frequencies were optionally normalized identically (so that they all have the same "units") (Step S208). For plugging in sequencing indel-frequency values, it may be best, however, to standardize sequencing depth. The preferred way to do this would be to set a standard sequencing-depth D for which all experiments included in $\vec{Z}$ have at least that number of reads. Since cutting frequencies below 1/D cannot be consistently detected, this should be set as the minimum frequency for the data-set, and the values in $\vec{Z}$ should range from log(1/D) to log(1). One could vary the value of D later on to ensure that the $\vec{\alpha}$ estimate isn't too dependent on the value chosen. Thus, values of Z could be filtered out if they do not meet the minimum sequencing depth (Step S210). Once the values of G and Z are input to the machine learning system, the weights can be determined (Step S212) and output (Step S214). These weights can then be used to estimate the free energy Z and the cutting frequency for any sequence. In a further aspect, there are different methods of graphing NGG and NNAGAAW sequences. One is with the 'non-overlapping' method. NGG and NRG may be regraphed in an "overlapping" fashion, as indicated in FIG. 6A-C. Applicants also performed a study on off target Cas9 activity as indicated in FIGS. 10, 11 and 12. Aspects of the invention also relate to predictive models that may not involve hybridization energies but instead simply use the cutting frequency information as a prediction.

FIG. 3 shows the steps in one method relating to the multiplicative algorithm which may be applied in identifying one or more unique target sequences in a genome of a eukaryotic organism, whereby the target sequence is susceptible to being recognized by a CRISPR-Cas system. The method comprises: a) creating a data training set as to a particular Cas. The data training set may be created as described in more detail later by determining the weights associated with a model. Once a data training set has been established, it can be used to predict the behavior of an input sequence and to identify one or more unique target sequences therein. At step S300, the genome sequence is input to the system. For a particular Cas, the next step is to locate a mismatch between a target sequence within the input sequence and guide RNA for the particular Cas (Step S302). For the identified mismatch, two average cutting frequencies are determined using the data training set. These are the average cutting frequency at the position of the mismatch (step S304) and the average cutting frequency associated with that type of mismatch (Step S306). These average cutting frequencies are determined from the data training set which is particular to that Cas. The next step S308 is to create a product by multiplying the average cutting frequency at a particular position by the average cutting frequency of a particular mismatch to obtain a first product. It is then determined at step S310 whether or not there are any other mismatches. If there are none, the target sequence is output as the unique target sequence. However, if there are other mismatches, steps 304 to 308 are repeated to obtain second and further products for any further particular position (s) of mismatches and particular mismatches. Where second and further products are created and all products are multiplied together to create an ultimate product. The ultimate product is then multiplied by the result of dividing the minimum distance between consecutive mismatches by the length of the target sequence (e.g. 18) (step S314) which effectively scales each ultimate product.

It will be appreciated that steps 312 and 314 are omitted if there is no mismatch at any position or if there is only one particular mismatch at one particular position. The process is then repeated for any other target sequences. The "scaled" ultimate products for each target sequence are each ranked to thereby obtain a ranking (Step S316), which allows for the identification of one or more unique target sequences by selecting the highest ranked one (Step S318): Thus the "scaled" ultimate product which represents the predicted cutting frequencies for genome-wide targets may be calculated by: $f_{est}=f(1)g(N_1, N_1')\times f(2)g(N_2, N_2')\times \ldots f(19)g(N_{19}, N_{19}')\times h$ with values $f(i)$ and $g(N_i N_j')$ at position i corresponding, respectively, to the aggregate position- and base-mismatch cutting frequencies for positions and pairings indicated in a generalized base transition matrix or an aggregate matrix, e.g. a matrix as indicated in FIG. 12c. In other words, $f(i)$ is the average cutting frequency at the particular position for the mismatch and $g(N_i, N'_i)$ is the average cutting frequency for the particular mismatch type for the mismatch. Each frequency was normalized to range from 0 to 1, such that $f \rightarrow (f-f_{min})/(f_{max}-f_{min})$. In case of a match, both were set equal to 1. The value h meanwhile re-weighted the estimated frequency by the minimum pairwise distance between consecutive mismatches in the target sequence. This value distance, in base-pairs, was divided by a constant which was indicative of the length of the target sequence (e.g. 18) to give a maximum value of 1 (in cases where fewer than 2 mismatches existed, or where mismatches occurred on opposite ends of the 19 bp target-window). Samples having a read-count of at least 10,000 (n=43) were plotted. Those tied in rank were given a rank-average. The Spearman correlation coefficient, 0.58, indicated that the estimated frequencies recapitulated 58% of the rank-variance for the observed cutting frequencies. Comparing $f_{est}$ with the cutting frequencies directly yielded a Pearson correlation of 0.89: While dominated by the highest-frequency gRNA/target pairs, this value indicated that nearly 90% of all cutting-frequency variance was explained by the predictions above. In further aspects of the invention, the multiplicative algorithm or the methods mentioned herein may also include thermodynamic factors, e.g. hybridization energies, or other factors of interest being multiplied in series to arrive at the ultimate product.

Figure 4:
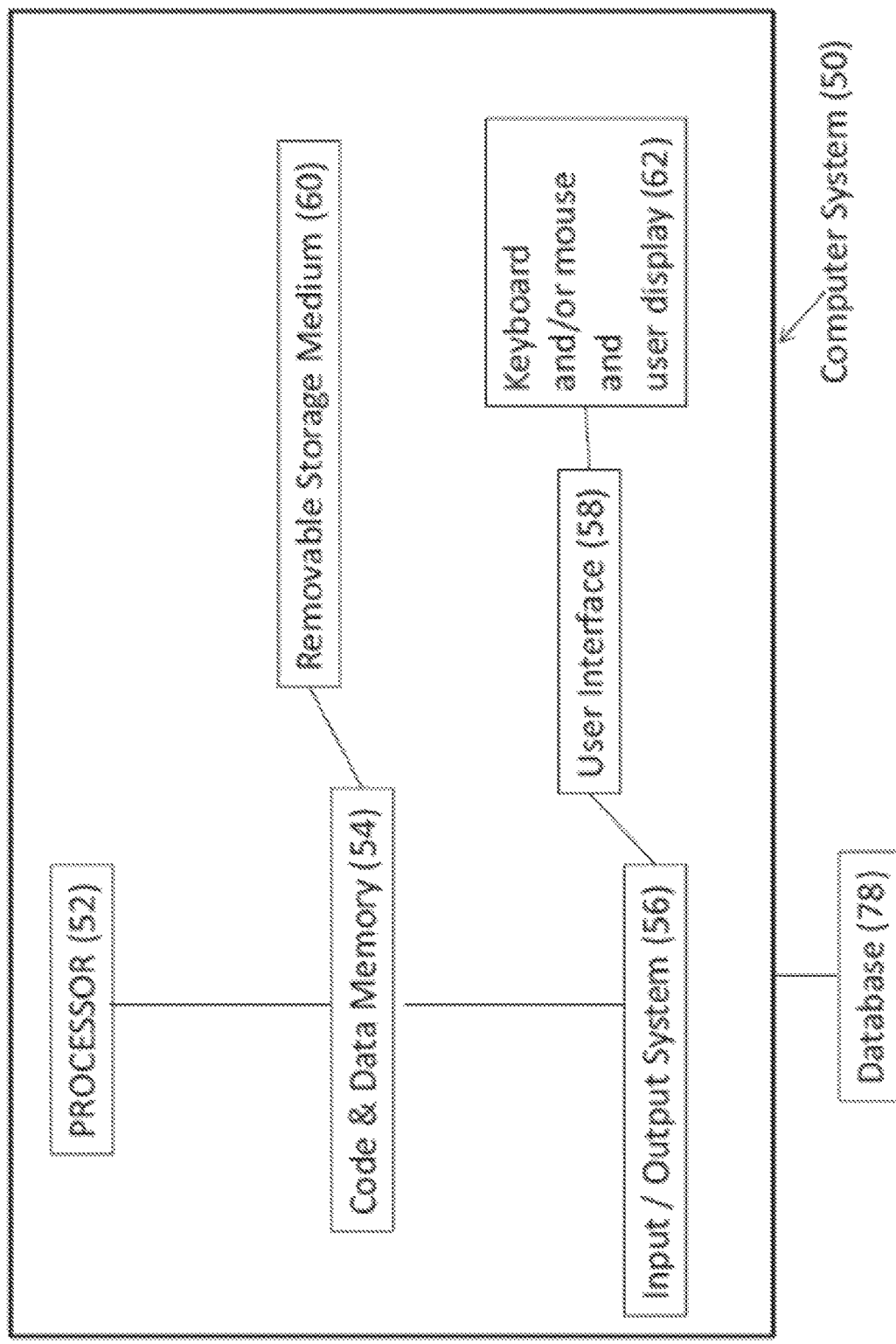
FIG. 4 shows a schematic block diagram of a computer system which can be used to implement the methods described herein.

FIG. 4 shows a schematic block diagram of a computer system which can be used to implement the methods described herein. The computer system 50 comprises a processor 52 coupled to code and data memory 54 and an input/output system 56 (for example comprising interfaces for a network and/or storage media and/or other communications). The code and/or data stored in memory 54 may be provided on a removable storage medium 60. There may also be a user interface 58 for example comprising a keyboard and/or mouse and a user display 62. The computer system is connected to a database 78. The database 78 comprises the data associated with the data training sets. The computer system is shown as a single computing device with multiple internal components which may be implemented from a single or multiple central processing units, e.g. microprocessors. It will be appreciated that the functionality of the device may be distributed across several computing devices. It will also be appreciated that the individual components may be combined into one or more components providing the combined functionality. Moreover, any of the modules, databases or devices shown may be implemented in a general purpose computer modified (e.g. programmed or configured) by software to be a special-purpose computer to perform the functions described herein. The processor may be configured to carry out the steps shown in the various flowcharts. The user interface may be used to input the genome sequence, the CRISPR motif and/or Cas for which a target sequence is to be identified. The output unique target sequence(s) may be displayed on the user display.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarily is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactetcaagatttaGAAAtaaatcttgcagaagctacaaagataaggcttcatgccgaaatcaacaccagtcattttatggcagggtgttttcgttatttaaTTTTTT (SEQ ID NO: 13); (2) NNNNNNNNNNNNNNNNNNNNgttttgtactctcaGAAAtgcagaagctacaaagataaggcttcatgccgaaatcaacaccetgtcattttatggcagggtgttacgttatttaaTTTTTT (SEQ ID NO: 14); (3) NNNNNNNNNNNNNNNNNNNNgttntgtactetcaGAAAtgcagaagetacaaagataaggcttcatgccgaaatcaacaccctgtcattttatgcagggtgtTTTTTT (SEQ ID NO: 15); (4) NNNNNNNNNNNNNNNNNNNNgttttagagetaGAAAtagcaagttaaaataaggetagtccgttatcaacttgaaaaagtggcaccgagteggtgaTTTTTT (SEQ ID NO: 16); (5) NNNNNNNNNNNNNNNNNNNNgttttagagctaGANA-TAGcaagttaaaataaggctagtccgttatcaacttgaaaaagtgTTTTTTT (SEQ ID NO: 17); and (6) NNNNNNNNNNNNNNNNNNNNgttttagagctagAAATAG-caagttaaaataaggctagtccgttatcaTTTTTTTT (SEQ ID NO: 1.8), In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 19) in the EMX1 gene of the human genome, deep sequencing can be used to assess the level of modification at the following two off-target loci, 1: 5'-GAGTC-CTAGCAGGAGAAGAA-3' (SEQ ID NO: 20) and 2: 5'-GAGTCTAAGCAGAAGAAGAA-3' (SEQ ID NO: 21). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to mimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx1.2), Cas10, Csy1, Csy2, Csy3, Cse1, Cse2, Csc1, Csc2, Csa5, Csn2, Csm2, Cstn3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0,01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S. pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR, locus in *Streptococcus pyogenes*. However, it will be appreciated that this invention includes many more Cas9s from other species of microbes, such as SpCas9, SaCa9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon. The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target comprising, consisting essentially of, or consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array comprising, consisting essentially of, or consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7,8, 9, 10, 20, 50, or more base pairs from) the target sequence. Without wishing to be bound by theory, the tracr sequence, which may comprise, consist essentially of, or consist of all or a portion of a wild-type tract: sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans being optimized for expression in humans), or for another eukaryote, animal or mammal as herein discussed; see, SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino add sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura. Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 22); the NLS from nucleoplasmin (e.g., the nucleoplasmin bipartite NLS with the sequence KRPAATKKAGQAKKKK (SEQ ID NO: 23)); the c-myc NLS having the amino acid sequence PAAKRVKLD (SEQ ID NO: 24) or RQRRNFLKRSP (SEQ ID NO: 25); the hRNPA1 M9 NLS having the sequence NQSSNFGPMKGGNFGGRSSGPYGGGGQNTAKPRNQGGY (SEQ ID NO: 26); the sequence RMRITFKNKGKDTAELRRRRVEVSVELRKAKKDEQILKRRNV (SEQ ID NO: 27) of the IBB domain from importin-alpha; the sequences VSRKRPRP (SEQ ID NO: 28) and PPKKARED(SEQ ID NO: 29) of the myoma T protein; the sequence PQRKIKKPL (SEQ ID NO: 30) of human p53; the sequence SALIKKKKKMAP (SEQ ID NO: 31) of mouse c-abl IV; the sequences DRLRR (SEQ ID NO: 32) and PKQKKRK (SEQ ID NO: 33) of the influenza virus NS1; the sequence RKLKKKIKKL (SEQ ID NO: 34) of the Hepatitis virus delta antigen; the sequence REKKKFLKRR (SEQ ID NO: 35) of the mouse Mx1, protein; the sequence KRKGDEVDGVDEVAKKKSKK (SEQ ID NO: 36) of the human poly(ADP-ribose) polymerase; and the sequence RKCLQAGMNLEARKTKK (SEQ ID NO: 37) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR, complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g., about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9; or an animal or mammal that is otherwise expressing Cas9 or has cells containing Cas9, such as by way of prior administration thereto of a vector or vectors that code for and express in vivo Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a. CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a particle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA,e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 by to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). The tareget can be a control element or a regulatory element or a promoter or an enhancer or a silencer. The promoter may, in some embodiments, be in the region of +200 bp or even +1000 bp from the TTS. In some embodiments, the regulatory region may be an enhancer. The enhancer is typically more than +1000 bp from the TTS. More in particular, expression of eukaryotic protein-coding genes generally is regulated through multiple cis-acting transcription-control regions. Some control elements are located close to the start site (promoter-proximal elements), whereas others lie more distant (enhancers and silencers) Promoters determine the site of transcription initiation and direct binding of RNA polymerase II. Three types of promoter sequences have been identified in eukaryotic DNA. The TATA box, the most common, is prevalent in rapidly transcribed genes. Initiator promoters infrequently are found in some genes, and CpG islands are characteristic of transcribed genes, Promoter-proximal elements occur within ≈200 base pairs of the start site. Several such elements, containing up to ≈20 base pairs, may help regulate a particular gene. Enhancers, which are usually ≈100-200 base pairs in length, contain multiple 8- to 20-bp control elements. They may be located from 200 base pairs to tens of kilobases upstream or downstream from a promoter, within an intron, or downstream from the final exon of a gene. Promoter-proximal elements and enhancers may be cell-type specific, functioning only in specific differentiated cell types. However, any of these regions can be the target sequence and are encompassed by the concept that the tareget can be a control element or a regulatory element or a promoter or an enhancer or a silencer.

Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9. An advantage of the present methods is that the CRISPR system minimizes or avoids off-target binding and its resulting side effects. This is achieved using systems arranged to have a high degree of sequence specificity for the target DNA.

In relation to a CRISPR-Cas complex or system preferably, the tracr sequence has one or more hairpins and is 30 or more nucleotides in length, 40 or more nucleotides in length, or 50 or more nucleotides in length; the guide sequence is between 10 to 30 nucleotides in length, the CRISPR/Cas enzyme is a Type II Cas9 enzyme.

One guide with a first aptamer/RNA-binding protein pair can be linked or fused to an activator, whilst a second guide with a second aptamer/RNA-binding protein pair can be linked or fused to a repressor. The guides are fir different targets (loci), so this allows one gene to be activated and one repressed. For example, the following schematic shows such an approach:
Guide 1—MS2 aptamer - - - MS2 RNA-binding protein - - - VP64 activator; and
Guide 2—PP7 aptamer - - - PP7 RNA-binding protein - - - SID4× repressor.

The present invention also relates to orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage Pseudomonas. Like MS2, it binds a specific RNA sequence and secondary structure. The PP7 RNA-recognition motif is distinct from that of MS2. Consequently, PP7 and NIS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as C7-beta.

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g., using the Alu repressor (in RNA) that interferes with RNA polymerase II in mammalian cells). The Alu RNA sequence was located: in place of the MS2 RNA sequences as used herein (e.g., at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of Cas9s to be delivered, as a comparatively small number of Cas9s can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the enzyme-guide complex as a whole may be associated with two or more functional domains. For example, there may be two or more functional domains associated with the enzyme, or there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS (SEQ ID NO: 43) can be used. They can be used in repeats of 3 ((GGGGS)$_3$) (SEQ ID NO: 38) or 6 (SEQ ID NO: 39), 9 (SEQ ID NO: 40) or even 12 (SEQ ID NO: 41) or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

The invention comprehends a CRISPR Cas complex comprising a CRISPR enzyme and a guide RNA (sgRNA), wherein the CRISPR enzyme comprises at least one mutation, such that the CRISPR enzyme has no more than 5% of the nuclease activity of the CRISPR enzyme not having the at least one mutation and, optional, at least one or more nuclear localization sequences; the guide RNA (sgRNA) comprises a guide sequence capable of hybridizing to a target sequence in a genomic locus of interest in a cell; and wherein: the CRISPR enzyme is associated with two or more functional domains; or at least one loop of the sgRNA is modified by the insertion of distinct RNA sequence(s) that bind to one or more adaptor proteins, and wherein the adaptor protein is associated with two or more functional domains; or the CRISPR enzyme is associated with one or more functional domains and at least one loop of the sgRNA is modified by the insertion of distinct RNA sequence(s) that bind to one or more adaptor proteins, and wherein the adaptor protein is associated with one or more functional domains.

Delivery Generally

Vector delivery, e.g., plasmid, viral delivery: The CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking, agents, fillers chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub, Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$–$1 \times 10^{12}$ particles), more preferably at least about $1 \times 10^7$ particles, more preferably at least about $1 \times 10^8$ particles (e.g., about $1 \times 10^8$–$1 \times 10^{11}$ particles or about $1 \times 10^8$–$1 \times 10^{12}$ particles), and most preferably at least about $1 \times 10^0$ particles (e.g., about $1 \times 10^9$–$1 \times 10^{10}$ particles or about $1 \times 10^9$–$1 \times 10^{12}$ particles), or even at least about $1 \times 10^{10}$ particles (e.g., about $1 \times 10^{10}$–$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al, Retina 24(4):660 which may also be applied to the present invention.

Indeed, RNA delivery is a useful method of in vivo delivery. It is possible to deliver Cas9 and gRNA. (and, for instance, HR repair template) into cells using liposomes or particles. Thus delivery of the CRISPR enzyme, such as a Cas9 and/or delivery of the RNAs of the invention may be in RNA form and via microvesicles, liposomes or particles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, P:MID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of 1×10$^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR. Cas targeted to the brain in a lentivirus having a titer of 1×10$^9$ transducing units (IU)/ml may be contemplated.

In terms of local delivery to the brain, this can be achieved in various ways. For instance, material can be delivered intrastriatally e.g., by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package Cas9 coding nucleic acid molecules, e.g., DNA, into vectors, e.g., viral vectors, to mediate genome modification in vivo include:

To achieve NHEJ-mediated gene knockout:
Single Virus Vector:
Vector containing two or more expression cassettes:
Promoter-Cas9 coding nucleic acid molecule-terminator
Promoter-gRNA1-terminator
Promoter-gRN A2-terminator
Promoter-gRNA(N)-terminator (up to size limit of vector)
Double Virus Vector:
Vector 1 containing one expression cassette for driving the expression of Cas9
Promoter-Cas9 coding nucleic acid molecule-terminator
Vector 2 containing one more expression cassettes for driving the expression of one or more guideRNAs
Promoter-gRNA1-terminator
Promoter-gRNA(N)-terminator (up to size limit of vector)
To mediate homology-directed repair.

In addition to the single and double virus vector approaches described above, an additional vector is used to deliver a homology-direct repair template.

The promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.

For ubiquitous expression, can use promoters: CMV, GAG, CBh, PGK, SV40, Ferritin heavy or light chains, etc.

For brain or other CNS expression, can use promoters: SynaspsinI for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.

The promoter used to drive guide RNA can include:
Pol III promoters such as U6 or H1
Use of Pol II promoter and intronic cassettes to express gRNA Adeno Associated Virus (AAV)

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cas9 can be driven by a cell-type specific promoter. For example, liver-specific expression might use the Albumin promoter and neuron-specific expression (e.g., for targeting CNS disorders) might use the Synapsin I promoter.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In terms of in vivo delivery, AAV is advantageous over other viral vectors for a couple of reasons:
Low toxicity (this may be due to the purification method not requiring ultra centrifugation of cell particles that can activate the immune response) and
Low probability of causing insertional mutagenesis because it doesn't integrate into the host genome, AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species.

Lentivirus

Lentiviruses are complex retroviruses that have the ability to infect and express their genes in both mitotic and post-mitotic cells. The most commonly known lentivirus is the human immunodeficiency virus (HIV) which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 µl of DMEM overnight at 4 C. They were then aliquotted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275 285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of $2.5 \times 10^6$ CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (Cell-Genix) at a density of $2 \times 10^6$ cells/ml. Prestimulated cells may be transduced with lentiviral at a multiplicity of infection of 5 for 16 to 24 hours in 75-cm$^2$ tissue culture flasks coated with fibronectin (25 mg/cm$^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543 US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GC-CACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g., using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particles

CRISPR enzyme mRNA and guide RNA may be delivered simultaneously using particles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10:1021/mp100390w Epub 2011 Apr. 1) describes biodegradable core-shell structured particles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Phartn, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al, J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver RNA to a cancer cell to stop tumor growth developed by Dan Anderson's lab at MIT may be used/and or adapted to the CRISPR Cas system of the present invention: In particular, the Anderson lab developed fully automated, combinatorial systems for the synthesis, purification, characterization, and formulation of new biomaterials and nanoformulations, See, e.g., Alabi et al., Prod Natl Acad Sci U S A. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, particles, liposomes, or micelles. The agent to be delivered by the particles, liposomes, or micelles may be in the form of a gas, liquid, or solid, and the agent may be a polynucleotide, protein, peptide, or small molecule. The minoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid particles (LNPs) are contemplated. An antitransthyretin small interfering RNA has been encapsulated in lipid particles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or CRISPR-Cas RNA in or associated with the LNP may be contemplated, especially for a formulation containing DLinKC2-DMA.

Preparation of LNPs and CRISPR. Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dim ethyl-3-aminopropane (DLinK-DMA). 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω- methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR Cas RNA may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DAM in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Spherical Nucleic Acid (SNA™) constructs and other particles (particularly gold nanoparticles) are also contemplated as a means to delivery CRISPR-Cas system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am, Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci, USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling particles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclodo-decane-1,4,7,10-tetraacetic acid mono(N-hydroxysuccinimide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield IOTA-siRNA. All liquids were pretreated with Chelex-100 (Bio-Rad, Hercules, Calif.) to remove trace metal contaminants. Tf-targeted and nontargeted siRNA particles may be formed by using cyclodextrin-containing polycations. Typically, particles were formed in water at a charge ratio of 3 (+/−) and an siRNA concentration of 0.5 g/liter. One percent of the adamantane-PEG molecules on the surface of the targeted particles were modified with Tf (adamantane-PEG-Tf). The particles were suspended in a 5% (wt/vol) glucose carrier solution for injection.

Davis et al. (Nature, Vol 464, 15 Apr. 2010) conducts a RNA clinical trial that uses a targeted particle-delivery system (clinical trial registration number NCT00689065). Patients with solid cancers refractory to standard-of-care therapies are administered doses of targeted particles on days 1, 3, 8 and 10 of a 21-day cycle by a 30-min intravenous infusion. The particles comprise, consist essentially of, or consist of a synthetic delivery system containing: (1) a linear, cyclodextrin-based polymer (CDP), (2) a human transferrin protein (TF) targeting ligand displayed on the exterior of the particle to engage TF receptors (TFR) on the surface of the cancer cells, (3) a hydrophilic polymer (polyethylene glycol (PEG) used to promote particle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These particles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR Cas system of the present invention. The delivery of the invention may be achieved with particles containing a linear, cyclodextrin-based polymer (CDP), a human transferrin protein (TF) targeting ligand displayed on the exterior of the particle to engage TF receptors (TFR) on the surface of the cancer cells and/or a hydrophilic polymer (for example, polyethylene glycol (PEG) used to promote particle stability in biological fluids).

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g., diameter) of less than 100 microns (□m). In some embodiments, inventive particles have a greatest dimension of less than 10 □m. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E, Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

In terms of this invention, it is preferred to have one or more components of CRISPR complex, e.g., CRISPR enzyme or mRNA or guide RNA delivered using particles or lipid envelopes. Other delivery systems or vectors are may be used in conjunction with the particle aspects of the invention.

In general, a "nanoparticle" refers to any particle having a diameter of less than 1000 nm. In certain preferred embodiments, particles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm.

Particles encompassed in the present invention may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome articles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 □m and 30 □m, incorporating a surfactant on the snake thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable nanoparticles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated azamacrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the particle may be epoxide-modified lipid-polymer, advantageously 7C1 (see, e.g., James E. Dahlman and Carmen Barnes et al. Nature Nanotechnology (2014) published online 11 May 2014, doi:10.1038/nnano.2014.84). C71 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered. GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al, harvested bone marrow from inbred CS7BL/6 mice with a homogenous major histocompatibility complex (MHC) haplotype. As immature dendritic cells produce large quantities of exosomes devoid of T-cell activators such as MHC-II and CD86, Alvarez-Erviti et al, selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by particle tracking analysis (NTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 µF resulted in the greatest retention of RNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P <0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al may be applied to deliver the CRISPR-Cas system of the present invention to therapeutic targets, especially neurodegenerative diseases. A dosage of about 100 to 1000 mg of CRISPR. Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al, explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing CRISPR Cas may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at (cshprotocols.cshl-p.org/content/2010/4/pdb.prot5407.long). These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA'DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravascular infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl) aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA dining particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR10 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-Ira were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 February 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_7HPO_4$, 1 mM $KH_2PO_d$, pH 7.5) by either dialysis or tangential flow diafiltration. siRNA were encapsulated in SNALP using a controlled step-wise dilution method process. The lipid constituents of KC2-SNALP were DLin-ICC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas or components thereof or nucleic acid molecule(s) coding therefor e.g., similar to SiRNA. (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CRISPR Cas system of the present invention to form lipid particles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA. (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid particles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailabillity challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release, 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo, David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (Mc-Naughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1\times10^5$ cells per well in a 48-well plate.

(2) On the day of treatment, dilute purified +36 GFP protein in serumfree media to a final concentration 200 nM. Add RNA to a final concentration of 50 nM. Vortex to mix and incubate at room temperature for 10 min.

(3) During incubation, aspirate media from cells and wash once with PBS.

(4) Following incubation of +36 GFP and RNA, add the protein-RNA complexes to cells.

(5) Incubate cells with complexes at 37° C. for 4 h.

(6) Following incubation, aspirate the media and wash three times with 20 U/mL heparin PBS. Incubate cells with serum-containing media for a further 48 h or longer depending upon the assay for activity.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1\times10^5$ per well in a 48-well plate.

(2) On the day of treatment, dilute purified k36 GFP protein in serumfree media to a final concentration 2 mM. Add 1 mg of plasmid DNA. Vortex to mix and incubate at room temperature for 10 min.

(3) During incubation, aspirate media from cells and wash once with PBS.

(4) Following incubation of p36 GFP and plasmid DNA, gently add the protein-DNA complexes to cells.

(5) Incubate cells with complexes at 37 C for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in inconjunction with herein teachints can be employed in the delivery of CRISPR Cas system(s) or component(s) thereof or nucleic acid molecule(s) coding therefor.

Implantable Devices

In another embodiment, implantable devices are also contemplated for delivery of the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 $m^3$ to 1 000 $mm^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear-auditory system, labyrinth of the inner ear, vestibular system; 11. Intra tracheal; 12. Intracardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, hi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Patient-Specific Screening Methods

A CRISPR-Cas system that targets nucleotide, e.g., tri-nucleotide repeats can be used to screen patients or patent samples for the presence of such repeats. The repeats can be the target of the RNA of the CRISPR-Cas system, and if there is binding thereto by the CRISPR-Cas system, that binding can be detected, to thereby indicate that such a repeat is present. Thus, a CRISPR-Cas system can be used to screen patients or patient samples for the presence of the repeat. The patient can then be administered suitable compound(s) to address the condition; or, can be administed a CRISPR-Cas system to bind to and cause insertion, deletion or mutation and alleviate the condition.

Nucleic Acids, Amino Acids and Proteins, Regulatory Sequences, Vectors, etc

Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarily that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques in Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SUS at 65° C., with wash in 0.2×SSC and 0.1% SUS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidornimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubell et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4$^{th}$ Ed.—Chapter 18), FASTA (Altschul et 1990 J. Mol. Biol. 403-410) and the GENEWORKS suite of comparison tools. Both BLAST and FASTA are available for offline and online searching (see Ausubel et al, 1999. Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| Set | | Sub-set | |
|---|---|---|---|
| Hydrophobic | FWYHKMILVAGC | Aromatic | F W Y H |
| | | Aliphatic | I L V |
| Polar | WYHKREDCSTNQ | Charged | H K R E D |
| | | Positively charged | H K R |
| | | Negatively charged | E D |
| Small | VCAGSPTND | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or 3-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E.coli* DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol. III promoter, such as a U6 promoter. Ideally the two are combined. The chimeric guide RNA typically comprises, consists essentially of, or consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCLIA (SEQ ID NO: 42). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECH- NOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pot II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-1 (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g., nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRITS (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mot. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al, MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific;

Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci, USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev,* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed. SSRs have been identified in Haloferax mediterranei, *Streptococcus pyogenes*, Anabaena, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochitn. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica. et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropymm, Pyrobaculum, Sulfolobus, Archaeoglobus, Hallocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobiutn, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga.*

In some embodiments, the CRISPR enzyme is part of a fusion protein comprising one or more heterologous protein domains (e.g., about or more than about 1, 2, 3, 4, 5, 6, 7, 8, 9, 10, or more domains in addition to the CRISPR, enzyme). A CRISPR enzyme fusion protein may comprise any additional protein sequence, and optionally a linker sequence between any two domains. Examples of protein domains that may be fused to a CRISPR, enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g., from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANLMAL CELL CULTURE (R. I. Freshney, ed. (1987)).

Modifying a Target

In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized or hybridizable to a target sequence, wherein said guide sequence may be linked to a tracr mate sequence which in turn may hybridize to a tracr sequence. Similar considerations and conditions apply as above for methods of modifying a target polynucleotide.

Kits

In one aspect, the invention provides kits containing any one or more of the elements disclosed in the above methods and compositions. Elements may be provided individually or in combinations, and may be provided in any suitable container, such as a vial, a bottle, or a tube. The kits may include the sgRNA and the unbound protector strand as described herein. The kits may include the sgRNA with the protector strand bound to at least partially to the guide sequence (i.e. pgRNA). Thus the kits may include the pgRNA in the form of a partially double stranded nucleotide sequence as described here. In some embodiments, the kit includes instructions in one or more languages, for example in more than one language. The instructions may be specific to the applications and methods described herein.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g., in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

Crystallization of CRISPR-Cas9 and Characterization of Crystal Structure

The crystals of the Cas9 can be obtained by techniques of protein crystallography, including batch, liquid bridge, dialysis, vapor diffusion and hanging drop methods. Generally, the crystals of the invention are grown by dissolving substantially pure CRISPR-Cas9 and a nucleic acid molecule to which it binds in an aqueous buffer containing a precipitant at a concentration just below that necessary to precipitate. Water is removed by controlled evaporation to produce precipitating conditions, which are maintained until crystal growth ceases. The crystal structure information is described in U.S. provisional applications 61/915,251 filed Dec. 12, 2013, 61/930,214 filed on Jan. 22, 2014, 61/980,012 filed Apr. 15, 2014; and Nishimasu et al, "Crystal Structure of Cas9 in Complex with Guide RNA and Target DNA," Cell 156(5):935-949, DOI: (dx.doi.org/10.1016/j.cell.2014.02.001) (2014), each and all of which are incorporated herein by reference.

Uses of the Crystals, Crystal Structure and Atomic Structure Co-Ordinates: The crystals of the Cas9, and particularly the atomic structure co-ordinates obtained therefrom, have a wide variety of uses. The crystals and structure co-ordinates are particularly useful for identifying compounds (nucleic acid molecules) that bind to CRISPR-Cas9, and CRISPR-Cas9s that can bind to particular compounds (nucleic acid molecules). Thus, the structure co-ordinates described herein can be used as phasing models in determining the crystal structures of additional synthetic or mutated CRISPR-Cas9s, Cas9s, nickases, binding domains. The provision of the crystal structure of CRISPR-Cas9 complexed with a nucleic acid molecule as applied in conjunction with the herein teachings provides the skilled artisan with a detailed insight into the mechanisms of action of CRISPR-Cas9. This insight provides a means to design modified CRISPR-Cas9s, such as by attaching thereto a functional group, such as a repressor or activator. While one can attach a functional group such as a repressor or activator to the N or C terminal of CRISPR-Cas9, the crystal structure demonstrates that the N terminal seems obscured or hidden, whereas the C terminal is more available for a functional group such as repressor or activator. Moreover, the crystal structure demonstrates that there is a flexible loop between approximately CRISPR-Cas9 (S. pyogenes) residues 534-676 which is suitable for attachment of a functional group such as an activator or repressor. Attachment can be via a linker, e.g., a flexible glycine-serine (GlyGlyCilySer) (SEQ ID NO: 43) or (GGGS)$_3$ (SEQ ID NC: 44) or a rigid alpha-helical linker such as (Ala(GluAlaAlaAlaLys)Ala) (SEQ ID NO: 45). In addition to the flexible loop there is also a nuclease or 1-13 region, an H2 region and a helical region. By "helix" or "helical", is meant a helix as known in the art, including, but not limited to an alpha-helix. Additionally, the term helix or helical may also be used to indicate a c-terminal helical element with an N-terminal turn.

The provision of the crystal structure of CRISPR-Cas9 complexed with a nucleic acid molecule allows a novel approach for drug or compound discovery, identification, and design for compounds that can bind to CRISPR-Cas9 and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans.

In any event, the determination of the three-dimensional structure of CRISPR-cas 9 (*S. pyogenes* Cas9) complex provides a basis for the design of new and specific nucleic acid molecules that bind to CRISPR-cas 9 (e.g., *S. pyogenes* Cas9), as well as the design of new CRISPR-Cas9 systems, such as by way of modification of the CRISPR-Cas9 system to bind to various nucleic acid molecules, by way of modification of the CRISPR-Cas9 system to have linked thereto to any one or more of various functional groups that may interact with each other, with the CRISPR-Cas9 (e.g., an inducible system that provides for self-activation and/or self-termination of function), with the nucleic acid molecule nucleic acid molecules (e.g., the functional group may be a regulatory or functional domain which may be selected from the group comprising, consisting essentially of, or consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase; and, in some aspects, the functional domain is an epigenetic regulator; see, e.g., Zhang et al., U.S. Pat. No. 8,507,272, and it is again mentioned that it and all documents cited herein and all apple cited documents are hereby incorporated herein by reference), by way of modification of Cas9, by way of novel nickases). Indeed, the herewith CRISPR-Cas9 (*S. pyogenes* Cas9) crystal structure has a multitude of uses. For example, from knowing the three-dimensional structure of CRISPR-Cas9 (*S. pyogenes* Cas9) crystal structure, computer modelling programs may be used to design or identify different molecules expected to interact with possible or confirmed sites such as binding sites or other structural or functional features of the CRISPR-Cas9 system (e.g., *S. pyogenes* Cas9). Compound that potentially bind ("binder") can be examined through the use of computer modeling using a docking program. Docking programs are known; for example GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders ascertain how well the shape and the chemical structure of the potential binder will bind to a CRISPR-Cas9 system (e.g., *S. pyogenes* Cas9). Computer-assisted, manual examination of the active site or binding site of a CRISPR-Cas9 system (e.g., *S. pyogenes* Cas9) may be performed. Programs such as GRID (P. Goodford, J. Med. Chem, 1985, 28, 849-57)—a program that determines probable interaction sites between molecules with various functional groups—may also be used to analyze the active site or binding site to predict partial structures of binding compounds. Computer programs can be employed to estimate the attraction, repulsion or steric hindrance of the two binding partners, e.g., CRISPR-Cas9 system (e.g., *S. pyogenes* Cas9) and a candidate nucleic acid molecule or a nucleic acid molecule and a candidate CRISPR-Cas9 system (e.g., *S. pyogenes* Cas9); and the CRISPR-Cas9 crystral structure (*S. pyogenes* Cas9) herewith enables such methods. Generally, the tighter the fit, the fewer the steric hindrances, and the greater the attractive forces, the more potent the potential binder, since these properties are consistent with a tighter binding constant. Furthermore, the more specificity in the design of a candidate CRISPR-Cas9 system (e.g., *S. pyogenes* Cas9), the more likely it is that it will not interact with off-target molecules as well. Also, "wet" methods are enabled by the instant invention. For example, in an aspect, the invention provides for a method for determining the structure of a binder (e.g., target nucleic acid molecule) of a candidate CRISPR-Cas9 system (e.g., *S. pyogenes* Cas9) bound to the candidate CRISPR-Cas9 system (e.g., *S. pyogenes* Cas9), said method comprising, (a) providing a first crystal of a candidate CRISPR-Cas9 system (*S. pyogenes* Cas9) according to the invention or a second crystal of a candidate a candidate CRISPR-Cas9 system (e.g., *S. pyogenes* Cas9), (b) contacting the first crystal or second crystal with said hinder under conditions whereby a complex may form; and (c) determining the structure of said a candidate (e.g., CRISPR-Cas9 system (e.g., *S. pyogenes* Cas9) or CRISPR-Cas9 system (*S. pyogenes* Cas9) complex. The second crystal may have essentially the same coordinates discussed herein, however due to minor alterations in CRISPR-Cas9 system (e.g., from the Cas9 of such a system being e.g., *S. pyogenes* Cas9 versus being *S. pyogenes* Cas9), wherein "e.g., *S. pyogenes* Cas9" indicates that the Cas9 is a Cas9 and can be of or derived from *S. pyogenes* or an ortholog thereof), the crystal may form in a different space group.

The invention further involves, in place of or in addition to "in silica" methods, other "wet" methods, including high throughput screening of a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)), to select compounds with binding activity. Those pairs of binder and CRISPR-Cas9 system which show binding activity may be selected and further crystallized with the CRISPR-Cas9 crystal having a structure herein, e.g., by co-crystallization or by soaking, for X-ray analysis. The resulting X-ray structure may be compared with that of the Cas9 Crystal Structure for a variety of purposes, e.g., for areas of overlap. Having designed, identified, or selected possible pairs of binder and CRISPR-Cas9 system by determining those which have favorable fitting properties, e.g., predicted strong attraction based on the pairs of binder and CRISPR-Cas9 crystal structure data herein, these possible pairs can then be screened by "wet" methods for activity. Consequently, in an aspect the invention can involve: Obtaining or synthesizing the possible pairs; and contacting a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex (es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-Cas9 system or components thereof. These steps may be repeated and re-repeated as necessary. Alternatively or additionally, potential CRISPR-Cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom.

The invention further involves a method of determining three dimensional structures of CRISPR-cas systems or complex(es) of unknown structure by using the structural co-ordinates of the Cas9 Crystal Structure. For example, if X-ray crystallographic or NMR spectroscopic data are provided for a CRISPR-cas system or complex of unknown crystal structure, the structure of a CRISPR-Cas9 complex may be used to interpret that data to provide a likely structure for the unknown system or complex by such techniques as by phase modeling in the case of X-ray crystallography. Thus, an inventive method can comprise: aligning a representation of the CRISPR-cas system or complex having an unknown crystal structure with an analogous representation of the CRISPR-cas(9) system and complex of the crystal structure herein to match homologous or analogous regions (e.g., homologous or analogous sequences); modeling the structure of the matched homologous or analogous regions sequences) of the CRISPR-cas system or complex of unknown crystal structure based on the structure of the Cas9 Crystal Structure of the corresponding regions (e.g., sequences); and, determining a conformation (e.g., taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as of nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art: Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the CRISPR-Cas9 crystal structure and those of a CRISPR-cas system of unknown crystal structure aid in the prediction and determination of the crystal structure of the CRISPR-cas system of unknown crystal structure.

Further still, the aspects of the invention which employ the CRISPR-Cas9 crystal structure in silico may be equally applied to new CRISPR-cas crystal structures divined by using the herein-referenced CRISPR-Cas9 crystal structure. In this fashion, a library of CRISPR-cas crystal structures can be obtained. Rational CRISPR-cas system design is thus provided by the instant invention. For instance, having determined a conformation or crystal structure of a CRISPR-cas system or complex, by the methods described herein, such a conformation may be used in a computer-based methods herein for determining the conformation or crystal structure of other CRISPR-cas systems or complexes whose crystal structures are yet unknown. Data from all of these crystal structures can be in a database, and the herein methods can be more robust by having herein comparisons involving the herein crystal structure or portions thereof be with respect to one or more crystal structures in the library. The invention further provides systems, such as computer systems, intended to generate structures and/or perform rational design of a CRISPR-cas system or complex. The system can contain: atomic co-ordinate data according to the herein-referenced. Crystal Structure or be derived therefrom e.g., by modeling, said data defining the three-dimensional structure of a CRISPR-cas system or complex or at least one domain or sub-domain thereof, or structure factor data therefor, said structure factor data being derivable from the atomic co-ordinate data of the herein-referenced Crystal Structure. The invention also involves computer readable media with: atomic co-ordinate data according to the herein-referenced Crystal Structure or derived therefrom e.g., by homology modeling, said data defining the three-dimensional structure of a CRISPR-cas system or complex or at least one domain or sub-domain thereof, or structure factor data therefor, said structure factor data being derivable from the atomic co-ordinate data of the herein-referenced Crystal Structure. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silica" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-cas systems or complexes; advantageously, the three-dimensional structure being as defined by the atomic co-ordinate data according to the herein-referenced Crystal Structure. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein-referenced Crystal Structure gives atomic co-ordinate data for a CRISPR-Cas9 (*S. pyogenes*), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number.

In particular embodiments of the invention, the conformational variations in the crystal structures of the CRISPR-Cas9 system or of components of the CRISPR-Cas9 provide important and critical information about the flexibility or movement of protein structure regions relative to nucleotide (RNA or DNA) structure regions that may be important for CRISPR-Cas system function. The structural information provided for Cas9 (e.g., pyogenes Cas9) as the CRISPR enzyme in the present application may be used to further engineer and optimize the CRISPR-Cas system and this may be extrapolated to interrogate structure-function relationships in other CRISPR enzyme systems as well. An aspect of the invention relates to the crystal structure of *S. pyogenes* Cas9 in complex with sgRNA and its target DNA at 2.4 Å resolution. The structure revealed a bilobed architecture composed of target recognition and nuclease lobes, accommodating a sgRNA:DNA duplex in a positively-charged groove at their interface. The recognition lobe is essential for sgRNA and DNA binding and the nuclease lobe contains the HNH and RuvC nuclease domains, which are properly positioned for the cleavage of complementary and non-complementary strands of the target DNA, respectively. This high-resolution structure and the functional analyses provided herein elucidate the molecular mechanism of RNA-guided DNA targeting by Cas9, and provides an abundance of information for generating optimized CRISPR-Cas systems and components thereof.

In particular embodiments of the invention, the crystal structure provides a critical step towards understanding the molecular mechanism of RNA-guided DNA targeting by Cas9. The structural and functional analyses herein provide a useful scaffold for rational engineering of Cas9-based genome modulating technologies and may provide guidance as to Cas9-mediated recognition of PAM sequences on the target DNA or mismatch tolerance between the sgRNA:DNA duplex. Aspects of the invention also relate to truncation mutants, e.g., an *S. pyogenes* Cas9 truncation mutant may facilitate packaging of Cas9 into size-constrained viral vectors for in vivo and therapeutic applications. Similarly, future engineering of the PAM Interacting (PI) domain may allow programing of PAM specificity, improve target site recognition fidelity, and increase the versatility of the Cas9 genome engineering platform.

The invention comprehends optimized functional CRISPR-Cas enzyme systems. In particular the CRISPR enzyme comprises one or more mutations that converts it to a DNA binding protein to which functional domains exhibiting a function of interest may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain.

The structural information provided herein allows for interrogation of sgRNA (or chimeric RNA) interaction with the target DNA and the CRISPR enzyme (e.g., Cas9) permitting engineering or alteration of sgRNA structure to optimize functionality of the entire CRISPR-Cas system. For example, loops of the sgRNA may be extended, without colliding with the Cas9 protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, F1, ID2, NL95, TW19, AP205, 4ϕCb5, ϕCb8r, ϕCb12r, ϕCb23r, 7s and PRR1. These adaptor proteins or orthogonal RNA binding proteins can further recruit effector proteins or fusions which comprise one or more functional domains. In some embodiments, the functional domain may be selected from the group comprising, consisting essentially of, or consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

In one aspect surveyor analysis is used for identification of indel activity/nuclease activity. In general survey analysis includes extraction of genomic DNA, PCR amplification of the genomic region flanking the CRISPR target site, purification of products, re-annealing to enable heteroduplex formation. After re-annealing, products are treated with SURVEYOR nuclease and SURVEYOR enhancer S (Transgenomics) following the manufacturer's recommended protocol. Analysis may be performed with poly-acrylamide gels according to known methods. Quantification may be based on relative band intensities.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publication US 2015-0031134 (U.S. application Ser. No. 14/497,627), which is allowed; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830, Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/835,973, 61/836,080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915,251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010,879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014.

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692. 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOMF EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE. INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. Applicatory 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR. MEDIATED IN VIVO MODELING AND GENETIC SCREENING TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, and filed 22 Oct. 2015, NOVEL CRISPR ENZYMES AND SYSTEMS, U.S. application 62/232,067, 24 Sep. 2015, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR Cas systems. Cong, L., Ran, F. A., Cox, D., Lin, S., Barretto, R., Habib, N., Hsu, P. D., Wu, X., Jiang, W., Marraffini, & Zhang, F. Science February 15; 339(6121):819-23 (2013);

RNA-guided editing of bacterial genomes using CRISPR-Cas systems. Jiang W., Bikard D., Cox D Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10. 1038,Nature12466 Epub 2013 Aug. 23;

Double Nicking by RNA-Guided CRISPR Cas9 for Enhanced Genome Editing Specificity. Ran, F A., Hsu, P D., Lin, C Y., Gootenberg, J S., K.onermann, S., Trevino, A E., Scott, D A., Inoue, A., Matoba, S., Zhang, & Zhang, F. Cell August 28. pii: S0092-8674 (13)01015-5. (2013);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308. (2013);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27. (2014). 156 (5):935-49;

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol.* (2014) April 20. doi: 10.1038/nbt.2889,

*CRISPR-Cas9 Knockin Mice for Genome Editing and Cancer Modeling*, Platt et al., Cell 159(2): 440-455 (2014) DOI: 10.1016/j.ce11.2014.09.014,

*Development and Applications of CRISPR-Cas9 for Genome Engineering*, Hsti et al, Cell 157, 1262-1278 (Jun. 5, 2014) (Hsu 2014),

*Genetic screens in human cells using the CRISPR/Cas9 system*, Wang et al., Science. 2014 Jan. 3; 343(6166): 80-84. doi: 10.1126/science.1246981,

*Rational design of highly active sgRATAs for CRISPR-Cas9-mediated gene inactivation*, Doench et al., Nature Biotechnology published online 3 Sep. 2014; doi: 10.1038/nbt.3026, and

*In vivo interrogation of gene function in the mammalian brain using CRISPR-Cas9*, Swiech et al, Nature Biotechnology; published online 19 Oct. 2014; doi: 10.1038/nbt.3055.

*Genome-scale transcriptional activation by an engineered CRISPR-Cas9 complex*, Konermann S, Brigham M D, Trevino A E, Joung J, Abudayyeh O O, Barcena C, Hsu P D, Habib N, Gootenberg J S, Nishimasu H, Nureki O; Zhang F., Nature. January 29; 517(7536):583-8 (2015).

*A split-Cas9 architecture for inducible genome editing and transcription modulation*, Zetsche B, Volz S E, Zhang F., (published online 2 Feb. 2015) Nat Biotechnol. February; 33(2):139-42 (2015);

*Genome-wide CRISPR Screen in a Mouse Model of Tumor Growth and Metastasis*, Chen S, Sanjana N E, Zhang K, Shalem O, Lee K, Shi X, Scott D A, Song J, Pan J O, Weissleder R, Lee H, Zhang F, Sharp P A. Cell 160, 1246-1260, Mar. 12, 2015 (multiplex screen in mouse), and)

In vivo genome editing using *Staphylococcus aureus* Cas9, Ran F A, Cong L, Yan W X, Scott D A, Gootenberg J S, Kriz A J, Zetsche B. Shalem O, Wu X, Makarova K S, Koonin E V, Sharp P A, Zhang F., (published online 1 Apr. 2015), Nature. April 9; 520 (7546):186-91 (2015).

*High-throughput functional genomics using CRISPR-Cas9*, Shalem et al., Nature Reviews Genetics 16, 299-311 (May 2015).

*Sequence determinants of improved CRISPR sgRNA design*, Xu et al., Genome Research 25, 1147-1157 (August 2015).

*A Genome-wide CRISPR Screen in Primary Immune Cells to Dissect Regulatory Networks*, Parnas et al., Cell 162, 675-686 (Jul. 30, 2015).

*CRISPR/Cas9 cleavage of viral DNA efficiently suppresses hepatitis B virus*, Ramanan et al., Scientific Reports 5:10833. doi: 10.1038/srep10833 (Jun. 2, 2015).

*Crystal Structure of Staphylococcus aureus Cas9*, Nishimasu et al., Cell 162, 1113-1126 (Aug. 27, 2015).

BCL11A enhancer dissection by Cas9-mediated in situ saturating mutagenesis, Canver et al., Nature 527 (7577):192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.201.5.10.008 Epub Oct. 22, 2015.

*Rationally engineered Cas9 nucleases with improved specificity*, Slaymaker et al., Science 2015 Dec. 1. pii: aad5227. [Epub ahead of print]

each of which is incorporated herein by reference, and discussed briefly below:

Cong et al. engineered type II CRISPR/Cas systems for use in eukaryotic cells based on both *Streptococcus thermophilus* Cas9 and also *Streptoccocus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided. nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in S. pneumankte, nearly 100% of cells that were recovered using the described approach contained the desired mutation, and in *E. coli*, 65% that were recovered contained the mutation.

Wang Epi al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPRICas system will greatly accelerate the in vivo study of functionally redundant genes and of epistatic gene interactions.

Konermann et al. addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-rnediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NEED) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF Their studies showed that the highest-ranking candidates included previously validated genes NF1 and MEDI2 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 Å° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HMI and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et at mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed. their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.)

Chen et al. relates to multiplex screening by demonstrating that a genome-wide in vivo CRISPR-Cas9 screen in mice reveals genes regulating lung metastasis.

Ran et al, (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.)

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnt) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA. (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TIGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2015) reported the use of structure-guided protein engineering to improve the specificity of Streptococcus pyogenes Cas9 (SpCas9). The authors developed "enhanced specificity" SpCas9 (eSpCas9) variants which maintained robust on-target cleavage with reduced off-target effects.

Mention is also made of Tsai et al, "Dimeric CRISPR RNA-guided FokI nucleases for highly specific genome editing," Nature Biotechnology 32(6): 569-77 (2014) which is not believed to be prior art to the instant invention or application, but which may be considered in the practice of the instant invention. Mention is also made of Konermann et al., "Genome-scale transcription activation by an engineered CRISPR-Cas9 complex," doi:10.1038/nature14136, incorporated herein by reference.

The present invention will be further illustrated in the following Examples which are given for illustration purposes only and are not intended to limit the invention in any way.

EXAMPLES

Example 1—Procedure for Design 1.0 Insert

Reagent Setup
D10 Media

To prepare D10 media, dissolve 50 mL of fetal bovine serum (1×) and 5.5 mL of Penicillin-Streptomycin (10,000 U/mL) in 500 mL Dulbecco's Modified Eagle Medium (1×). Filtrate the media by using a 0.5 µm filter. Store for several months at 4° C.

PBS-BSA Solution

To prepare 1 L of PBS-0.1% BSA solution, dissolve 1 g of BSA in 1 L of PBS. Store at room temperature (25° C.) for up to 1 year.

6M LiCl Solution

To prepare 6M LiCl solution, dissolve 12.72 g of LiCl in 0.5 mL 1M Tris-HCl (pH 7.5) and 0.1 mL 0.5M EDTA (pH 8.0) and adjust the volume with water to 50 mL. Filtrate the solution by using a 0.5 µm filter. Store for several months at room temperature.

3M LiCl Solution

To prepare 3M LiCl solution, dilute 6M LiCl solution 1:2 in 0.5 mL 1M Tris-HCl (pH 7.5) and 0.1 mL 0.5M EDTA (pH 8.0).

Insert Production (Annealing of Bottom-Strand 5' Oligo)
Prepare second PNK anneal reaction as follows, incubate 37° C. for 30 minutes, and cool to 25° C. at 5° C./min:

| Component | Volume |
|---|---|
| ddH$_2$O | 32.5 µL |
| oligo 1 (top strand DNA insert) | 5 µL |
| oligo 1 (bottom strand 5' oligo) | 5 µL |

| Component | Volume |
|---|---|
| 10X T4 DNA ligation buffer | 5 µL |
| T4 PNK | 2.5 µL |

Insert Production (Second Strand Synthesis)

Prepare second synthesis reaction as follows and perform a 1.5× spri for isolation of dsDNA insert after second strand synthesis:

| Component | Volume |
|---|---|
| PNK anneal reaction | 50 µL |
| 10X T4 DNA ligation buffer | 1 µL |
| dNTPS (10 mM) | 3 µL |
| Klenow | 3 µL |
| ddH$_2$O | 3 µL |

U6-sgRNA Production

Set up a 50 µL reaction for each U6-sgRNA template to be amplified by exponential PCR from target sgRNA-specific primers as follows:

| Component | Volume | Final | |
|---|---|---|---|
| ddH$_2$O | 36.875 µL | | |
| Herc II buffer (5x) | 10 µL | 1x | |
| Herc II polymerase (0.5 µL reactions) | 1 µL | | 2 reactions |
| dNTPS (10 mM) | 1 µL | 10 nmol | |
| px362 (800 ng/µL) | 0.025 µL | 20 ng | |
| xrp596 (100 µM) | 0.1 µL | 10 pmol | |
| sgRNA Primer (10 µM) | 1 µL | 10 pmol | |

Amplify U6-sgRNA templates using the following PCR program:

| Cycle | Denaturation | Annealing | Elongation | Final |
|---|---|---|---|---|
| Start | 3 min at 95° C. | | | |
| 1-30 | 20 sec at 95° C. | 20 sec at 60° C. | 20 sec at 72° C. | |
| Hold | | | | 4° C. |

Transfection with dsDNA Insert

Culture HEK 293T cells in 40 mL, of D10 media in T-75 flasks. Maintain at 50-90% confluency, trypsinizing and splitting cells in fresh D10 media every 2-3 days;

The evening before transfection, plate cells at 30-40% confluency in 500 µL in 24-well culture plates;

The day of transfection, wait until cells have reached 60-70% confluency;

Transient transfect HEK 293T cells via lipofectamine with Cas9 plasmid, target U6-sgRNA template, and DNA inserts;

Replace with fresh D10 media 4-8 hours following transfection.

Propagation and Harvesting

Maintain cells at 50-90% confluency, trypsinizing and splitting cells 1:3 in fresh D10 media every 2-3 days.

At each time point, harvest two-thirds of cells in a 96-microwell plate. Pellet cells by centrifuging the plate at 300 g for 5 minutes and aspirating off media.

QuickExtract genomic DNA from cells by suspending pelleted cells in 50 µL of Illumina QuickExtract DNA Extraction Solution and using the following temperature program:

| Duration | Temperature |
|---|---|
| 15 min | 65° C. |
| 15 min | 68° C. |
| 10 min | 98° C. |
| Hold | 4° C. |

SPRI

To remove excess non-integrated genomic inserts, perform a 0.5×SPRI by first reconstituting each DNA sample up to 100 µL with ddH$_2$O.

Pipette-mix 50 µL SPRI beads into each sample, then incubate at room temperature for 5 minutes.

Magnetize samples and remove supernatant.

While still magnetized, wash samples 2× with 200 µL of 70% ethanol Aspirate excess ethanol.

Air-dry samples for 8-10 minutes, then elute in 41 µL of ddH$_2$O.

Non-Restrictive Linear PCR

Set up a 50 µL reaction for each DNA sample to be amplified by linear PCR from 5'-biotinylated dsDNA insert primer P1a/P1b as follows:

| Component | Volume | Final |
|---|---|---|
| Template DNA (100-1000 ng) | 41 µL | 100-100 ng |
| Taq buffer (10x) | 5 µL | 1x |
| Taq polymerase (2.5 U/µL) | 1 µL | 2.5U |
| dNTPS (10 mM) | 1 µL | 10 nmol |
| P1a/P1b (10 µM) | 1 µL | 10 pmol |

Amplify nucleic acid fragments using the following PCR program:

| Cycle | Denaturation | Annealing | Elongation | Final |
|---|---|---|---|---|
| Start | 2 min at 95° C. | | | |
| 1-35 | 45 sec at 95° C. | 45 sec at 58° C. | 5 sec at 72° C. | |
| Hold | | | | 4° C. |

Biotin Capture

Magnetize 20 µL of biotin beads at room temperature for 60 seconds, and then discard the supernatant.

Resuspend the beads 40 µL of PBS-BSA, magnetize, and discard the supernatant. Repeat this step once.

Wash the beads in 20 µL of 3M LiCl solution, magnetize, and then resuspend them in 50 µL of 6M LiCl.

Transfer 50 µL of the magnetic bead solution to the concentrated linear PCR product.

Incubate the samples for 2 hours at room temperature on a horizontal rotator to non-covalently link the biotinylated linear PCR product to the streptavidin coupled beads.

Magnetize the DNA-beads complex for 60 seconds, discard the supernatant, and elute in 100 µL of ddH$_7$O.

ssDNA Handle Ligation

Set up a 20 µL ligation reaction for each DNA-beads complex to ligate the ssDNA handle to the linear PCR product.

| Component | Volume | Final |
|---|---|---|
| ddH$_2$O | 3.6 µL | |
| PEG 8000 (50%, wt/vol) | 10 µL | 25% |
| Ligation buffer (10x) | 2 µL | 1x |
| ATP (10 mM) | 2 µL | 20 nmol |

-continued

| Component | Volume | Final |
|---|---|---|
| ssDNA handle (100 μM) | 0.2 μL | 20 pmol |
| Hexammine cobah(III) chloride (100 μM) | 0.2 μL | 20 pmol |
| T4 RNA ligase 1 (20 U/μL) | 2 μL | 40U |

Magnetize the DNA-beads complex for 60 seconds, discard the supernatant, and resuspend in the 20 μL ligation mixture, pipetting very slowly.

Incubate the samples overnight at room temperature on a horizontal rotator for 16 hours.

Add 80 μL of ddH$_2$O to the ligation mixture, magnetize, and discard the supernatant.

Resuspend the DNA-beads complex in 40 μL of ddH$_2$O.

First Exponential PCR

Set up a 50 μL PCR reaction for each ssDNA fragment to be exponentially amplified by dsDNA insert primer P2a/P2b and ssDNA handle primer P3 as follows:

| Component | Volume | Final |
|---|---|---|
| ddH$_2$O | 34 μL | |
| Herc II buffer (5x) | 10 μL | 1x |
| Herc II polymerase (0.5 μL reactions) | 1 μL | 2 reactions |
| dNTPS (10 mM) | 1 μL | 10 nmol |
| P2a/P2b (10 μM) | 1 μL | 10 pmol |
| P3 (10 μM) | 1 μL | 10 pmol |
| Template DNA (100-1000 ng) | 2 μL | 100-1000 ng |

Amplify nucleic acid fragments using the following PCR program:

| Cycle | Denaturation | Annealing | Elongation | Final |
|---|---|---|---|---|
| Start | 3 min at 95° C. | | | |
| 1-25 | 20 sec at 95° C. | 20 sec at 58° C. | 1 min at 72° C. | |
| Hold | | | | 4° C. |

Second Exponential PCR

Set up a 20 μL PCR reaction for each dsDNA fragment to be exponentially amplified by Illumina forward barcode primer R and reverse barcode R as follows:

| Component | Volume | Final |
|---|---|---|
| ddH$_2$O | 14.72 μL | |
| Herc II buffer (5x) | 4 μL | 1x |
| Herc II polymerase (0.5 μL reactions) | 0.4 μL | 0.8 reactions |
| dNTPS (10 mM) | 0.4 μL | 4 nmol |
| F (100 μM) | 0.04 μL | 4 pmol |
| R (100 μM) | 0.04 μL | 4 pmol |
| Template DNA (100-1000 ng) | 0.4 μL | 100-1000 ng |

Amplify nucleic acid fragments using the following PCR program:

| Cycle | Denaturation | Annealing | Elongation | Final |
|---|---|---|---|---|
| Start | 3 min at 95° C. | | | |
| 1-15 | 20 sec at 95° C. | 20 sec at 58° C. | 1 min at 72° C. | |
| Hold | | | | 4° C. |

Library Preparation and Next Generation Sequencing

Pool library from 2 μL of each sample. Mix library well by vortexing.

Run 25 μL of pooled library on gel. Cut band from 300 bp to 600 bp and gel-purify.

Dilute library to 4 nM in ddH$_2$O.

Denature library by pipette-mixing 5 μL of library with 5 μL 0.2N NaOH and incubate for 5 minutes.

Prepare for sequencing by pipette-mixing denatured library 990 μL Illumina loading buffer, then dilute by pipette-mixing 700 μL of this solution in 300 μL of Illumina loading buffer.

Load diluted, denatured library solution in an Illumina MiSeq Reagent Kit v3 600 and sequence with 250 bp forward reads and 250 bp reverse reads.

Demultiplex sequencing by Illumina barcodes F and R to identify unique insertion events through EBC and handle ligations through LBC.

Protocol (Design 2)

Reagent Setup

D10 Media

To prepare D10 media, dissolve 50 mL of fetal bovine serum (1×) and 5.5 mL of Penicillin-Streptomycin (10,000 U/mL) in 500 mL Dulbecco's Modified Eagle Medium (1×). Filtrate the media by using a 0.5 μm filter. Store for several months at 4° C.

PBS-BSA Solution

To prepare 11- of PBS-0.1% BSA solution, dissolve 1 g of BSA in 1 L of PBS. Store at room temperature (25° C.) for up to 1 year.

6M LiCl Solution

To prepare 6M LiCl solution, dissolve 12.72 g of LiCl in 0.5 mL 1M Tris-HCl (pH 7.5) and 0.1 mL 0.5M EDTA (pH 8.0) and adjust the volume with water to 50 mL. Filtrate the solution by using a 0.5 μm filter. Store for several months at room temperature.

3M LiCl Solution

To prepare 3M LiCl solution, dilute 6M LiCl solution 1:2 in 0.5 mL 1M Tris-HCl (pH 7.5) and 0.1 mL 0.5M EDTA (pH 8.0).

End Repair Buffer

To prepare 25 μL of end repair buffer, mix 6.7 μL T4 DNA ligase buffer (10×), 0.335 μL 1% BSA solution, 0.67 μL dNTPs (10 mM), and 17.295 μL ddH$_2$O.

A-Base Addition Buffer

To prepare 17 μL of Abase addition buffer, mix 6 μL NEB buffer 2 (10×), 0.1 dATP (100 mM), and 10.9 μL ddH$_2$O.

Procedure

Insert Production (Annealing of Bottom-Strand 5' Oligo)

Prepare second PNK anneal reaction as follows, incubate 37 C for 30 minutes, and cool to 25 C at 5 C/min:

| Component | Volume | Final |
|---|---|---|
| ddH$_2$O | 32.5 μL | |
| oligo 1 (top strand DNA insert) | 5 μL | |
| oligo 1 (bottom strand 5' oligo) | 5 μL | |
| 10X T4 DNA ligation buffer | 5 μL | |
| T4 PNK | 2.5 μL | |

Insert Production (Second Strand Synthesis for Biotin Labeled Top-Strand Oligo)

Prepare second synthesis reaction as follows and perform a 2.3× spri for isolation of dsDNA insert after second strand synthesis:

| Component | Volume | Final |
|---|---|---|
| PNK anneal reaction | 50 μL | |
| 10X T4 DNA ligation buffer | 1 μL | |
| dNTPS (10 mM) | 3 μL | |
| Klenow | 3 μL | |
| ddH₂O | 3 μL | |

NOTE: Insert Production (Second Strand Synthesis Biotin Labeling)

Prepare second strand synthesis reaction as above, substituting biotinylated nucleotides complimentary to target sites on top-strand oligo for biotin labeling:

U6-sgRNA Production

Set up a 50 μL reaction for each U6-sgRNA template to be amplified by exponential PCR from target sgRNA-specific primers as follows:

| Component | Volume | Final |
|---|---|---|
| ddH₂O | 36.875 μL | |
| Herc II buffer (5x) | 10 μL | 1x |
| Herc II polymerase (0.5 μL reactions) | 1 μL | 2 reactions |
| dNTPS (10 mM) | 1 μL | 10 nmol |
| px362 (800 ng/μL) | 0.025 μL | 20 ng |
| xrp596 (100 μM) | 0.1 μL | 10 pmol |
| sgRNA Primer (10 μM) | 1 μL | 10 pmol |

Amplify U6-sgRNA templates using the following PCR program:

| Cycle | Denaturation | Annealing | Elongation | Final |
|---|---|---|---|---|
| Start | 3 min at 95° C. | | | |
| 1-30 | 20 sec at 95° C. | 20 sec at 60° C. | 20 sec at 72° C. | |
| Hold | | | | 4° C. |

Transfection with Biotinylated dsDNA Insert

Culture HEK 293T cells in 40 mL of D10 media in T-75 flasks. Maintain at 50-90% confluency, trypsinizing and splitting cells in fresh D10 media every 2-3 days.

The evening before transfection, plate cells at 30-40% confluency in 10 mL of D10 media on 10 cm² plates. (While this protocol was performed on 10 cm² culture plates for which approximately 15 million cells can be harvested, it is expected that it could be performed on 24-well culture plates for which approximately 300,000 cells can be harvested.)

The day of transfection, wait until cells have reached 60-70% confluency.

Transient transfect HEK 293T cells via lipofectamine with Cas9 plasmid, target U6-sgRNA template, and DNA inserts.

Replace with fresh D10 media 4-8 hours following transfection.

Harvest cells at 24 hours-7 days post-transfection.

Genomic DNA Extraction and Fragmentation

Perform cell and tissue DNA midiprep of samples. Elute in 100 μL ddH₂O.

Normalize all DNA samples to same concentration.

Fragment the DNA samples to mean fragment size of 300 bp by sonicating for 15 minutes on high, with 60 second-on/30 second-off intervals.

Aliquot 100 μL fragmented genomic DNA samples.

Biotin Capture

Magnetize 60 μL of biotin beads at room temperature for 60 seconds, and then discard the supernatant.

Resuspend the beads 100 μL of PBS-BSA, magnetize, and discard the supernatant. Repeat this step once.

Wash the beads in 100 μL of 3M LiCl solution, magnetize, and then resuspend them in 100 μL of 6M LiCl.

Transfer 100 μL of the magnetic bead solution to the 100 μL of fragmented genomic DNA samples.

Incubate the samples for 1 hours at room temperature on a horizontal rotator to non-covalently link the biotinylated fragmented genomic DNA to the streptavidin coupled beads.

Magnetize the DNA-beads complex for 60 seconds, discard the supernatant, and resuspend in 200 μL of ddH₂O. Repeat this step twice.

Elute in 40 μL of ddH₂O.

End Repair and A-Tailing

Set up 67 μL end repair reaction to eliminate loose ends on fragmented genomic DNA:

| Component | Volume | Final |
|---|---|---|
| Genomic DNA fragment | 40 μL | |
| End repair buffer | 25 μL | |
| T4 polynucleotide kinase (10 U/μL) | 1 μL | 10 U |
| T4 polymerase (3 U/μL) | 1 μL | 3 U |

Incubate for 30 minutes at room temperature on a horizontal rotator to repair loose ends on fragmented genomic DNA.

Magnetize the DNA-beads complex for 60 seconds, discard the supernatant, and resuspend in 2004 of ddH₂O. Repeat this step twice.

Elute in 40 μL of ddH₂O.

Set up 60 μL A-tailing reaction to add 3' A-tails to end-repaired fragmented genomic DNA:

| Component | Volume | Final |
|---|---|---|
| End-repaired genomic DNA fragment | 40 μL | |
| A-base addition | 17 μL | |
| Klenow exo- (5 U/μL) | 3 μL | 15 U |

Incubate at 37° C., mixing vigorously every 5 minutes to keep DNA-heads complex in suspension, to A-tail end-repaired fragmented genomic DNA.

Magnetize the DNA-beads complex for 60 seconds, discard the supernatant, and resuspend in 2004 of ddH₂O. Repeat this step twice.

Elute in 20 μL of ddH2O.

Adapter Ligation and Enrichment

Set up 60 μL adapter ligation reaction to ligate Illumina Y-adapters onto A-tailed fragmented genomic DNA:

| Component | Volume | Final |
|---|---|---|
| A-tailed genomic DNA fragment | 20 μL | |
| DNA quick ligase buffer (2x) | 30 μL | 1x |
| DNA ligase | 5 μL | |
| Y-adapter (0.75 μM) | 5 μL | |

Incubate for 15 minutes at room temperature on a horizontal rotator to ligate Illumina Y-adapters onto A-tailed fragmented genomic DNA.

Magnetize the DNA-beads complex for 60 seconds, discard the supernatant, and resuspend in 200 μL of ddH₂O. Repeat this step twice.

Elute in 40 μL of ddH₂O.

Set up a 50 μL PCR reaction for Y-adapted genomic DNA fragments to be exponentially amplified:

| Component | Volume | Final |
|---|---|---|
| Y-adapted genomic DNA fragment | 40 μL | |
| Pfu Ultra II buffer (10x) | 5 μL | 1x |
| Pfu Ultra II fusion | 1 μL | |
| dNTPs (10 mM) | 2 μL | 20 nmol |
| ddH$_2$O | 2 μL | |

Amplify Y-adapted genomic DNA fragments using the following PCR program:

| Cycle | Denaturation | Annealing | Elongation | Final |
|---|---|---|---|---|
| Start | 2 min at 95° C. | | | |
| 1-28 | 2 min at 95° C. | 30 sec at 55° C. | 1 min at 72° C. | |
| Hold | | | 10 min at 72° C. | 4° C. |

Library Preparation and Next Generation Sequencing

Pool library from 2 μL of each sample. Mix library well by vortexing.

Run 25 μL of pooled library on gel. Cut band from 300 bp to 600 bp and gel-purify.

Dilute library to 4 nM in ddH$_2$O.

Denature library by pipette-mixing 5 μL of library with 5 μL 0.2N NaOH and incubate for 5 minutes.

Prepare for sequencing by pipette-mixing denatured library 990 μL Illumina loading buffer, then dilute by pipette-mixing 700 μL of this solution in 300 μL of Illumina loading buffer.

Load diluted, denatured library solution in an Illumina MiSeq Reagent Kit v3 600 and sequence with 250 bp forward reads and 250 bp reverse reads.

Example 2—Analysis of DSBs

In cells subject to genome editing, a DSB is induced at a target site in the cells DNA. Unintended DSBs may can also occur, for example, due to editing activity at off-target sites, and by other "background" mechanisms unrelated to genome editing. In evaluating specificity of genome editing processes, it is useful to distinguish DSBs at off-target sites from other background events.

To investigate genome-wide cleavage activity a data analysis pipline was developed, initially for use with BLESS (direct in situ breaks labelling, enrichment on streptavidin and next-generation sequencing). BLESS was applied to capture a snapshot of Cas9-induced DNA double-stranded breaks (DSBs) in cells. 293FT cells were transfected with SaCas9 or SpCas9 and EMX1 targeting guides, or pUC19 as a negative control. After cells were fixed, free genomic DNA ends from DSBs were captured using biotinylated adaptors and analysed by deep sequencing. With BLESS sequence reads and alignments to the genome in hand, to identify candidate Cas9-induced DSB sites genome-wide (as distinguished from genome wide DSBs arising from other sources), a three-step analysis pipeline was established.

Figure 13:
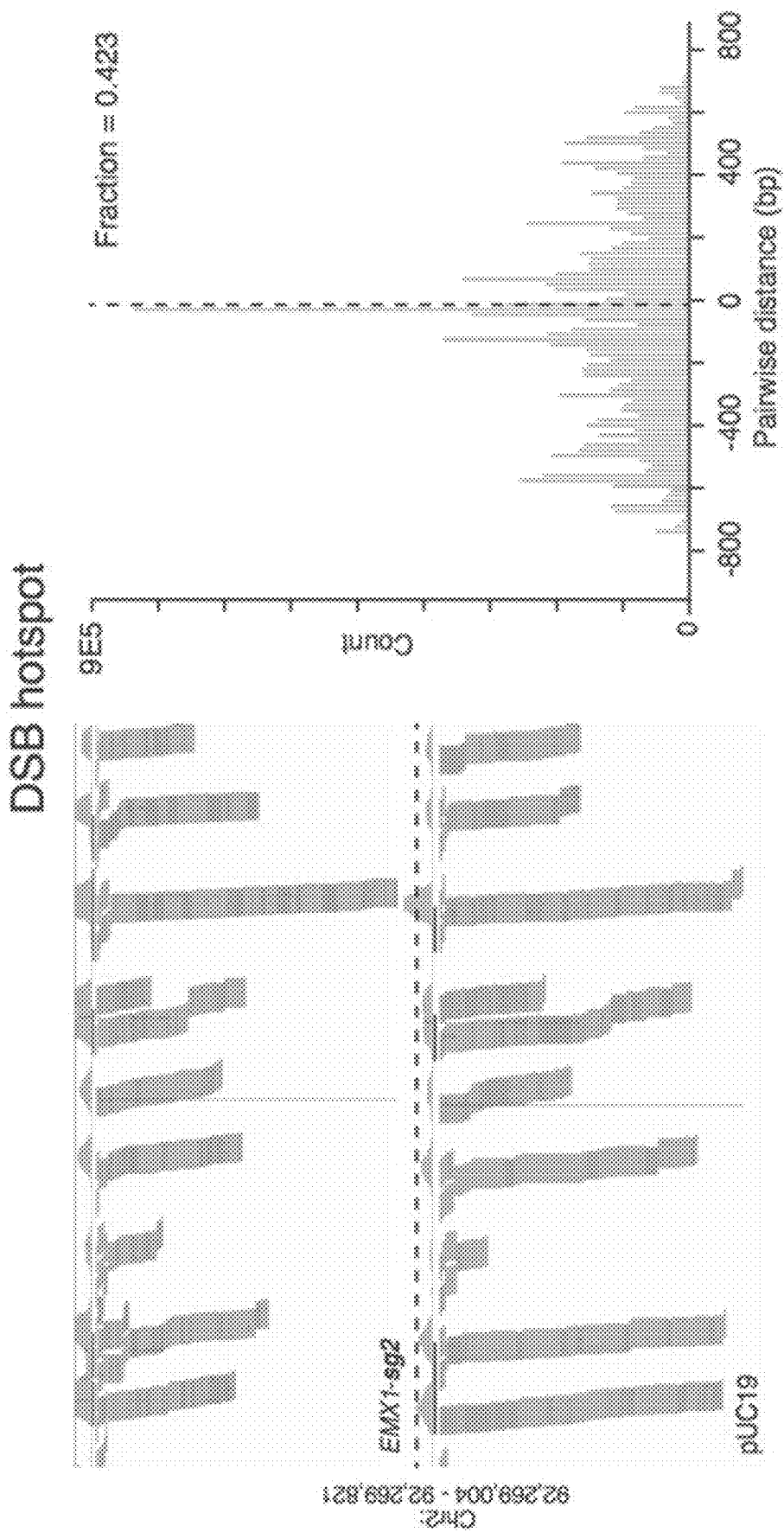
FIG. 13 depicts representative DSB hotspots. Representative sequence read mappings (left) and corresponding histograms of the pairwise distances between all forward orientation (red) reads and reverse orientation (blue) reads (right) are shown. DSBs at each hotspot show a range of break points; forward and reverse reads overlap.
Figure 14:
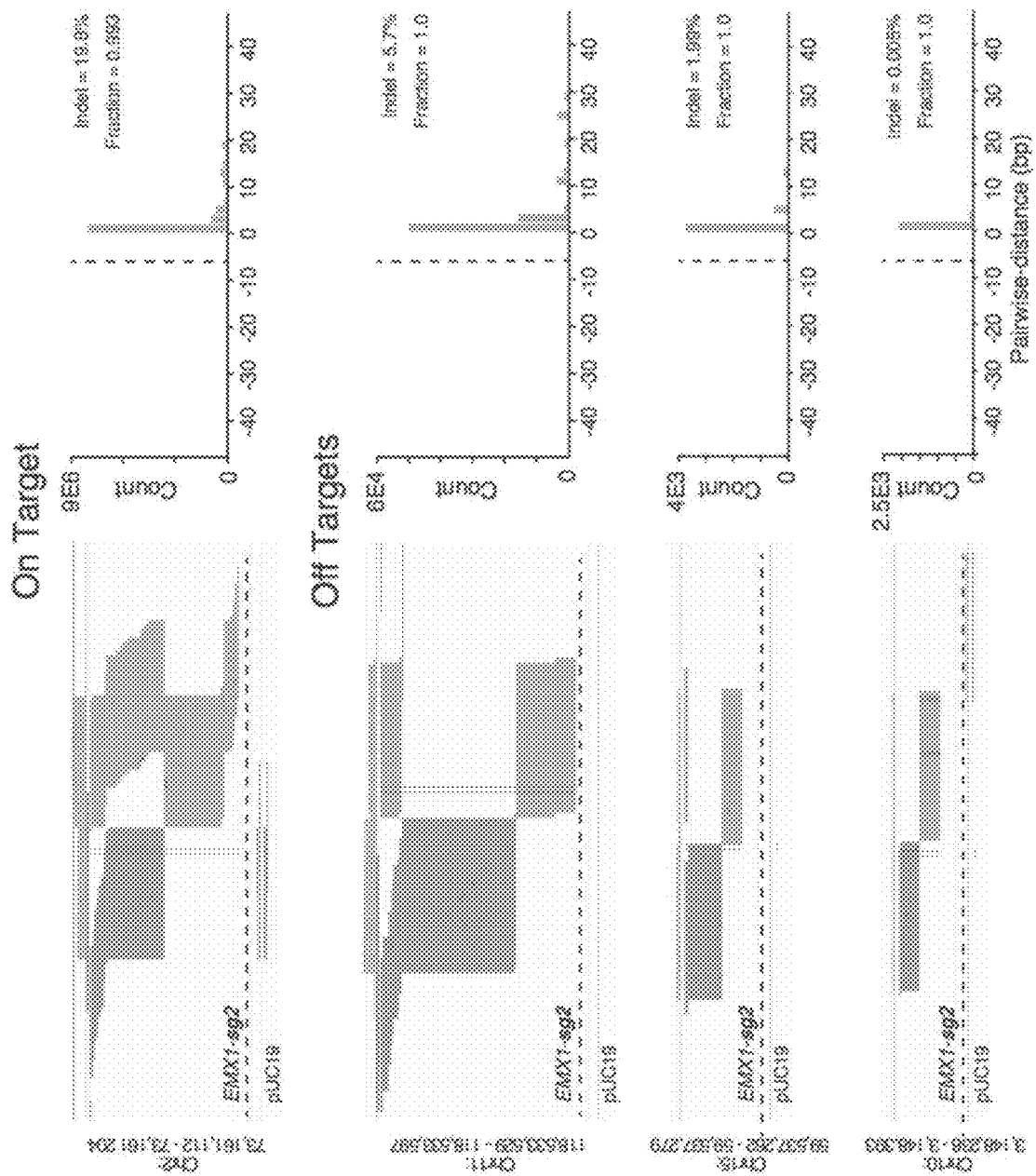
FIG. 14 depicts Cas9-induced DSBs with detectable indels. Representative sequence read mappings (left) and corresponding histograms of the pairwise distances between all forward orientation (red) reads and reverse orientation (blue) reads (right) are shown. The fraction of pairwise distances between reads overlapping by no more than 6 bp (dashed vertical line) are indicated over histogram plots.
Figure 15:
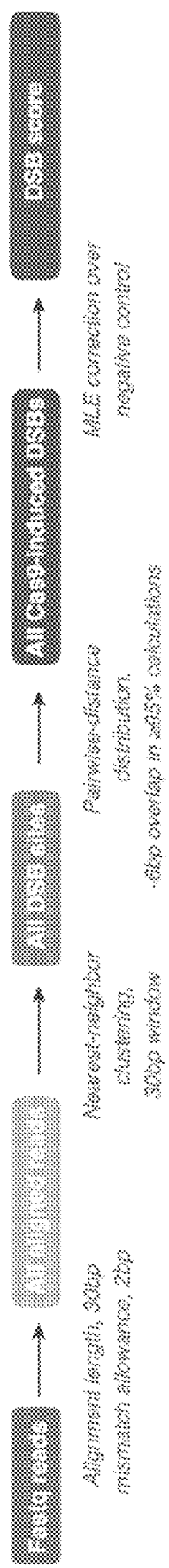
FIG. 15 depicts the analysis pipeline for sequencing data from BLESS or BLISS used to score on- and off target DSBs.

First, nearest-neighbor clustering was applied to the aligned reads to identify groups of DSBs (DSB clusters) across the genome. It was sought to separate potential Cas9-induced DSB clusters from background DSB clusters resulting from low frequency biological processes and technical artifacts, as well as high-frequency telomeric and centromeric DSB hotspots. From the on-target site and a small subset of verified off-target sites, it was observed that reads in Cas9-induced DSB clusters mapped to characteristic, well-defined genomic positions (FIG. 14) compared to the more diffuse alignment pattern at background DSB clusters (FIG. 12) and DSB hotspots (FIG. 13). A measure was developed to distinguish between the two types of DSB clusters: in each cluster the distance between all possible pairs of forward and reverse-oriented reads was calculated, and the background DSB clusters were filtered out based on the distinctive pairwise-distance distribution of these clusters. Third, the DSB score for a given locus was calculated by comparing the count of DSBs in the experimental and negative control samples using a maximum-likelihood estimate. This analysis identified the on-target loci for both SaCas9 and SpCas9 guides as the top scoring sites, and also revealed additional sites with high DSB scores.

Figure 8:
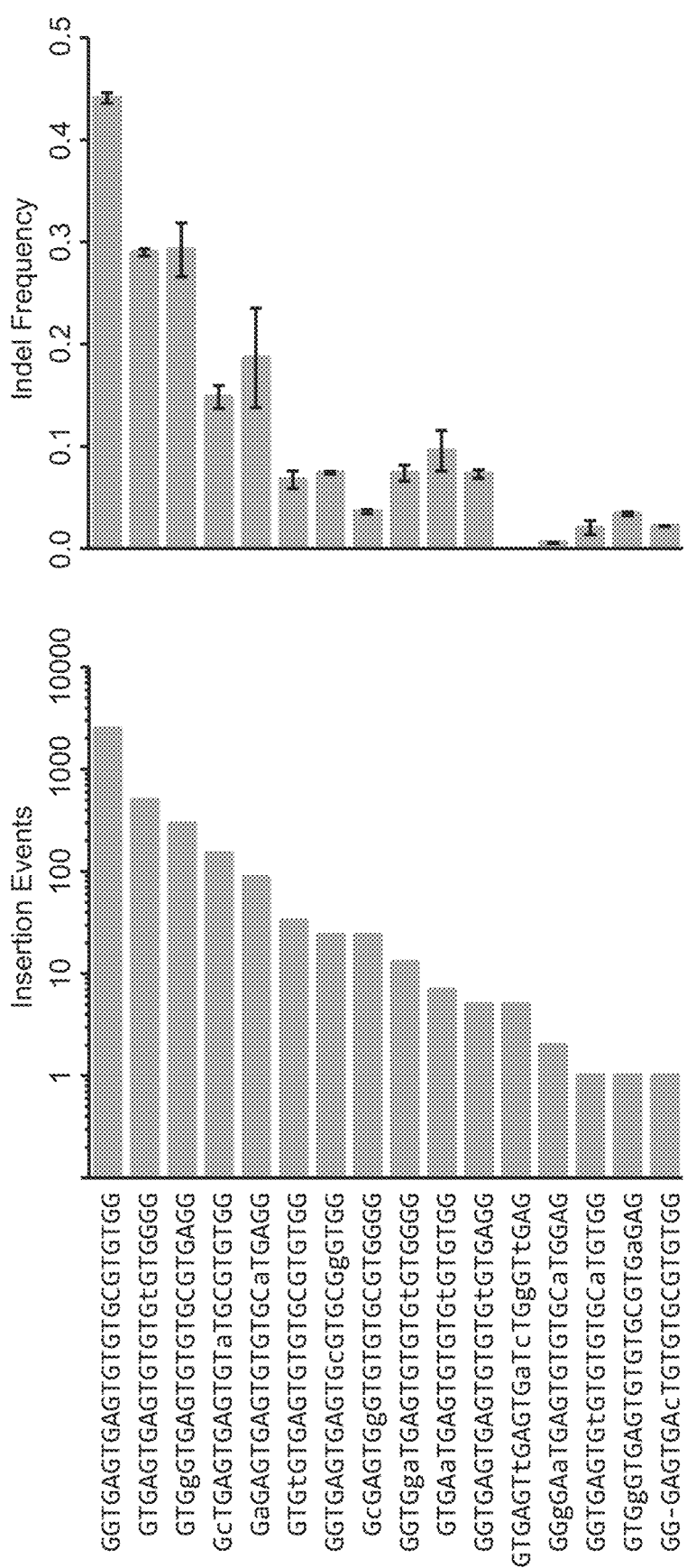
FIG. 8: On and off-target insert enrichment for VEGFA3 editing: (Left) enrichment plot of normalized insert event counts for on-target and validated off-target sites(SEQ ID NOS 52-67, respectively, in order of appearance) (Right) Maximum likelihood estimate (MLE) indel frequencies for on-target and validated off-target sites.
Figure 9:
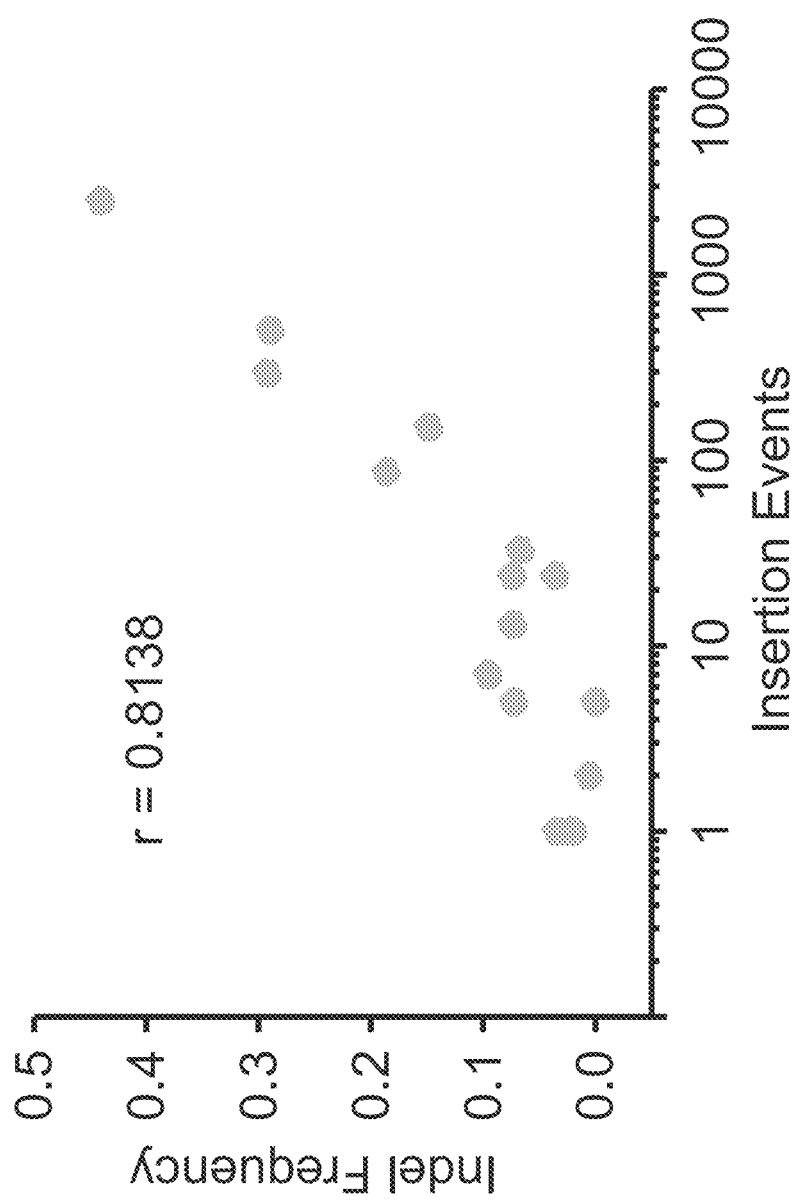
FIG. 9: Correlation between insert enrichment and indel frequencies for VEGFA3 on and off-target sites: Scatter plot shows MLE indel frequencies vs. insertion events for VEGFA3 on target and validated off-target sites. Pearson product-moment correlation coefficient (r) between indel and insert frequencies is 0.8138.

Targeted deep sequencing was used to detect indel formation on the ~30 top-ranking off-target sites identified by BLESS for each Cas9 and sgRNA combination. Only those sites that contained PAM and homology to the guide sequence exhibited indels (Extended Data FIG. 8). There was a strong linear correlation between DSB scores and indel levels for each Cas9 and sgRNA pairing.

After fixation, cells are lysed with a buffer containing Triton X-100 (to break the plasma membrane) followed by a buffer containing SDS (to break the nucleus membrane and partially unload protein complexes from DSB ends). The original BLESS method featured an incubation step with proteinase K to digest most of the cytoplasmic proteins and free DSB ends. However, this step required extensive optimization for every new cell line, and resulted in a pellet of nuclei difficult to visualize and easy to lose during centrifugation steps. The same proteinase K concentration range (100-200 micrograms per mL) cannot be used in BLISS, otherwise nuclei would detach from the microscope slide/coverslip. However, much lower concentrations of the enzyme can be scouted to determine if the amount of DSB ends sequenced substantially increases.

Example 3—BLISS Methods

Figure 16:
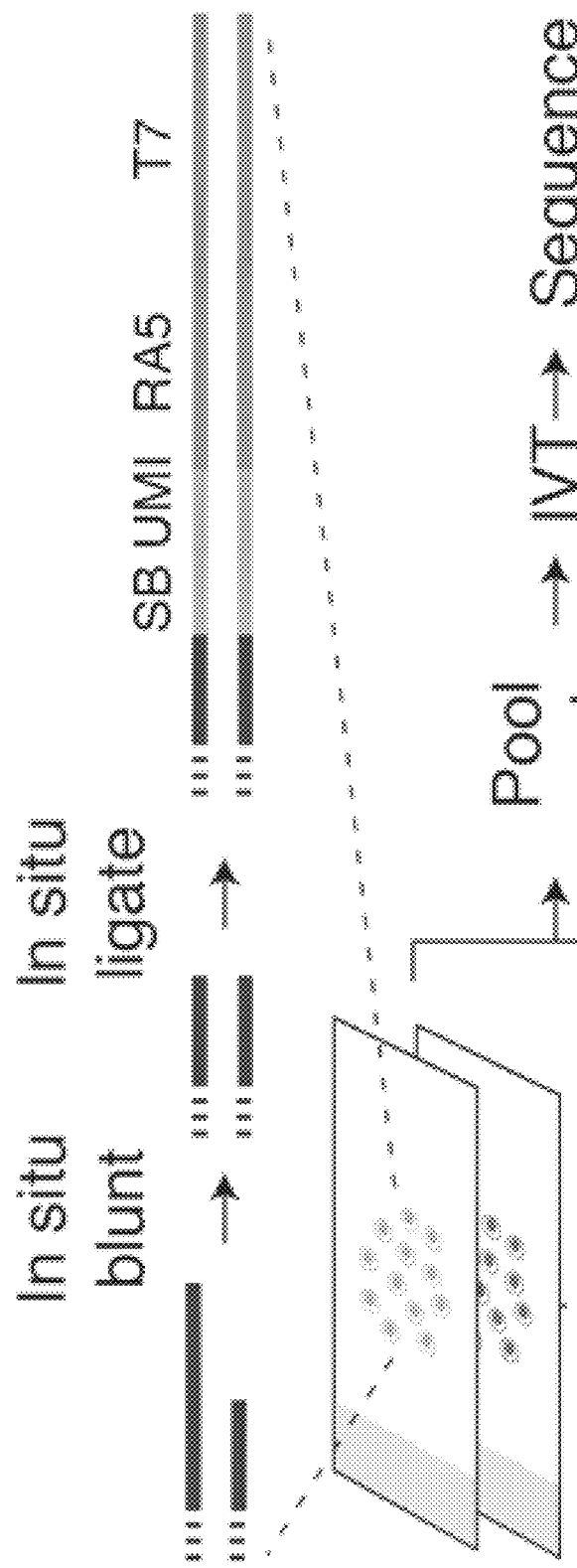
FIG. 16 depicts method workflow for BLISS. A defined number of cells are fixed onto a microscope slide and DSBs are in situ blunted and ligated with oligo. Linkers containing a sample barcode (SB), a Unique Molecular Identifier (UMI), the Illumina RA5 adaptor (RA5), and the T7 promoter sequence. After in situ ligation, DNA extracted from multiple differentially barcoded samples is pooled and linearly amplified by In Vitro Transcription (IVT). A sequencing library is prepared from the resulting amplified RNA, and finally sequenced on an Illumina platform.

A scheme of the BLISS method is shown in FIG. 16. Cells were first fixed onto microscope slides or microscope coverslips. Adherent cells can be directly grown onto coverslips or treated (e.g., Poly D lysine or Geltrex coated) cell culture media, while suspension cells are spotted onto adhesive slides or pre-coated coverslips (e.g. using poly-L-lysine or similar adhesion matrices). If needed, adherent cells can be first trypsinized and then spotted in desired amounts similarly to suspension cells. Cell fixation was performed using a cross-linking agent (typically, methanol-free paraformaldehyde) directly onto the microscope slide/coverslip for a short period of time (typically, <30 min at 20-25° C.). Slides/coverslips with fixed cells can be stored for several months in a suitable buffer solution at +4° C. (typically, Phosphate Buffer Saline with sodium azide to prevent bacterial growth). Samples in this format can also be conveniently shipped at +4° C. For slides, cells are typically spotted over a small circular area (usually, 1 cm in diameter), so that they can be covered with a suitable hybridization chamber to facilitate downstream steps (for example, we use SecureSeal chambers from Grace Bio-Labs). For tissues, 5-50 micron-thick sections can be cut and mounted on a microscope slide according to conventional histology procedures. Fresh-frozen tissues can be embedded in OCT and sectioned according to standard methods. Frozen sections can be mounted onto adhesive slides or coated coverslips, followed by fixation as for cells. Standard pathology formalin-fixed, paraffin-embedded (FFPE) tissues, are typically fixed for a longer period of time (typically, overnight). Pre-treatment of FFPE sections with standard antigen retrieval procedures used in immunohistochemistry is expected to be compatible with the in situ blunting and ligation steps of BLISS.

After fixation, cells were lysed with a buffer containing Triton X-100 (to break the plasma membrane) followed by a buffer containing SDS (to break the nucleus membrane and partially unload protein complexes from DSB ends). The original BLESS method featured an incubation step with proteinase K to digest most of the cytoplasmic proteins and free DSB ends. However, this step required extensive optimization for every new cell line, and resulted in a pellet of nuclei difficult to visualize and easy to lose during centrifugation steps. The same proteinase K concentration range (100-200 micrograms per mL) cannot be used in BUSS applications in which cells or tissue are fixed to a support, otherwise nuclei would detach. However, much lower concentrations of the proteinase K may increase the amount of DSB ends that can be sequenced without substantially increasing loss the support.

DSBs can be either repaired by non-homologous end-joining (NHEJ) or homologous recombination (HR). In the latter process, the 5' end of DSBs is partially resected by specialized endonucleases, resulting in 3' overhangs that need to be trimmed in order for universal linkers to be ligated. To do so, a blunting step is performed directly in situ, as in the original BLESS method. After blunting, DSBs are in situ ligated using oligonucleotide linkers comprising a sample barcode, a unique molecular identifier (UMI), the Illumina RA5 adaptor, and the T7 promoter sequence (FIG. 17; Table 1).

BLISS protocol below. In sense oligos exemplified in in Table 1, the order of the segments is Sample barcode (8 nt), UMI (8 nt), Illumina RA5 adapter (26 nt), T7 promoter (37 nt), "AA" overhang to block heat-to-tail concatemerization (2 nt). UMIs are recognizable as 8 contiguous "N"; not all linkers contain barcodes.

To facilitate ligation, an in situ A-tailing step following blunting is optional. Linkers containing a 5' T overhang can then be used for ligation instead of standard blunted BLISS linkers. In the usual procedure cells/tissue sections are attached to a solid support. Thus, all enzymatic reactions and washes until DNA extraction are done on-slide, avoiding sample loss for exam pie during centrifugations.

After in situ ligation, genomic DNA was fragmented in situ using a frequently cutting restriction endonuclease (for example, HaeIII) by digesting fixed cells in the presence of high concentrations of the enzyme. The choice of enzyme depends on the nature of the target (for example, when studying DSBs induced by specific endonucleases such as AsiSI, certain restriction enzymes cannot be used because their cutting site is too close to the recognition site of the enzyme under investigation). In situ fragmentation can be entirely substituted by sonication of DNA in applications where bias would not be introduced, such as in the case of using BLISS to evaluate off targets generated by targeted endonucleases such as CRISPR-Cas9.

After in situ DNA fragmentation, cells are captured from the slide/coverslip using a variety of alternative approaches: 1) cells can be mechanically scraped off using tissue culture scrapers; 2) cells are captured using the patented Pinpoint Slide DNA Isolation System™ (Zymo Research); 3) cells are captured using a Laser Capture Microdissection (LCM) system. The latter approach is particularly suitable for tissue sections to isolate select regions/cell populations of interest.

TABLE 1

BLISS linkers

| L linker | Sequence (5' to 3') | Description |
| --- | --- | --- |
| L1 | GCGTGATG-N-NNNNNNN-GATCGTCGGACTGTAGAACTCTGAAC-CCCTATAGTGAGTCGTATTACCGGCCTCAATCG-AA (SEQ ID NO: 46) | Sense oligo |
|  | CGATTGAGGCCGGTAATACGACTCACTATAGGG-GTTCAGAGTTTCTACAGTCCGACGATC-NNNNNNNN-CATCACGC (SEQ ID NO: 47) | Antisense oligo |
| L2 | NNNNNNNN-GATCGTCGGACTGTAGAACTCTGAAC-CCCTATAGTGAGTCGTATTACCGGCCTCAATCG-AA (SEQ ID NO: 48) | Sense oligo |
|  | CGATTGAGGCCGGTAATACGACTCACTATAGGG-GTTCAGAGTTCTACAGTCCGACGATC-NNNNNNNN-GTCGTTCC (SEQ ID NO: 49) | Antisense oligo |
| L3 | NNNNNNNN-GATCGTCGGACTGTAGAACTCTGAAC-CCCTATAGTGAGTCGTATTACCGGCCTCAATCG-AA (SEQ ID NO: 48) | Sense oligo |
|  | CGATTGAGGCCGGTAATACGACTCACTATAGGG-GTTCAGAGTTCTACAGTCCGACGATC-NNNNNNNNT-TGATGATC (SEQ ID NO: 50) | Antisense oligo |
| L4 | NNNNNNNN-GATCGTCGGACTGTAGAACTCTGAAC-CCCTATAGTGAGTCGTATTACCGGCCTCAATCG-AA (SEQ ID NO: 48) | Sense oligo |
|  | CGATTGAGGCCGGTAATACGACTCACTATAGGG-GTTCAGAGTTCTACAGTCCGACGATC-NNNNNNNN-TGATGCGC (SEQ ID NO: 51) | Antisense oligo |

Each BLISS linker is generated by annealing together a sense with an antisense oligo as described in the step-by-step Before capture, cells/tissue sections can be stained for example by DAPI, hematoxylineosin (H&E), or immunofluorescence to guide selective capture. Importantly, the precise amount of cells to be isolated can be quantified before capture by imaging the sample using a scanning microscope (for example, we use a Nikon TI-S-E Motorized stage microscope operated by NIS-Elements software). The measured cell count can then be used to normalize sequencing data when comparing different datasets.

After cell capture, DNA is extracted and purified using either standard phenolchloroform and alcohol precipitation methods, or commercially available silica column kits. Genomic DNA can be sonicated prior to in vitro transcription (IVT) aiming at obtaining a fragment size range of 200-500 nucleotides.

In the original BLESS method, DSBs are labeled with biotinylated linkers and enriched using streptavidin magnetic beads. This procedure requires relatively high amounts of purified genomic DNA, and is prone to bead loss during washes. To enable selective DSBs enrichment and simultaneously minimize sample loss, in BLISS advantage is taken of DSB labeling using the promoter sequence of the highly specific T7 RNA polymerase. During IVT, the T7 RNA polymerase only transcribes DNA molecules that had originated from DSBs. Moreover, during IVT the same target is copied multiple times in a linear fashion (unlike in PCR), therefore allowing DSBs to be detected even in very low-quantity samples. Importantly, multiple samples in which DSBs have been ligated using BLISS linkers carrying different barcodes can be pooled before IVT, enabling convenient and cost-effective multiplexing.

After IVT, the amplified RNA is used to prepare a sequencing library following a modified protocol based on the TruSeq Small RNA Library Preparation Kit (Illumina). Genomic DNA in the IVT reaction can be digested prior to purification of the amplified RNA. Finally, libraries can be sequenced using alumina platforms such as MiSeq or HiSeq.

Example 4—T7 Adapters

Figure 18:
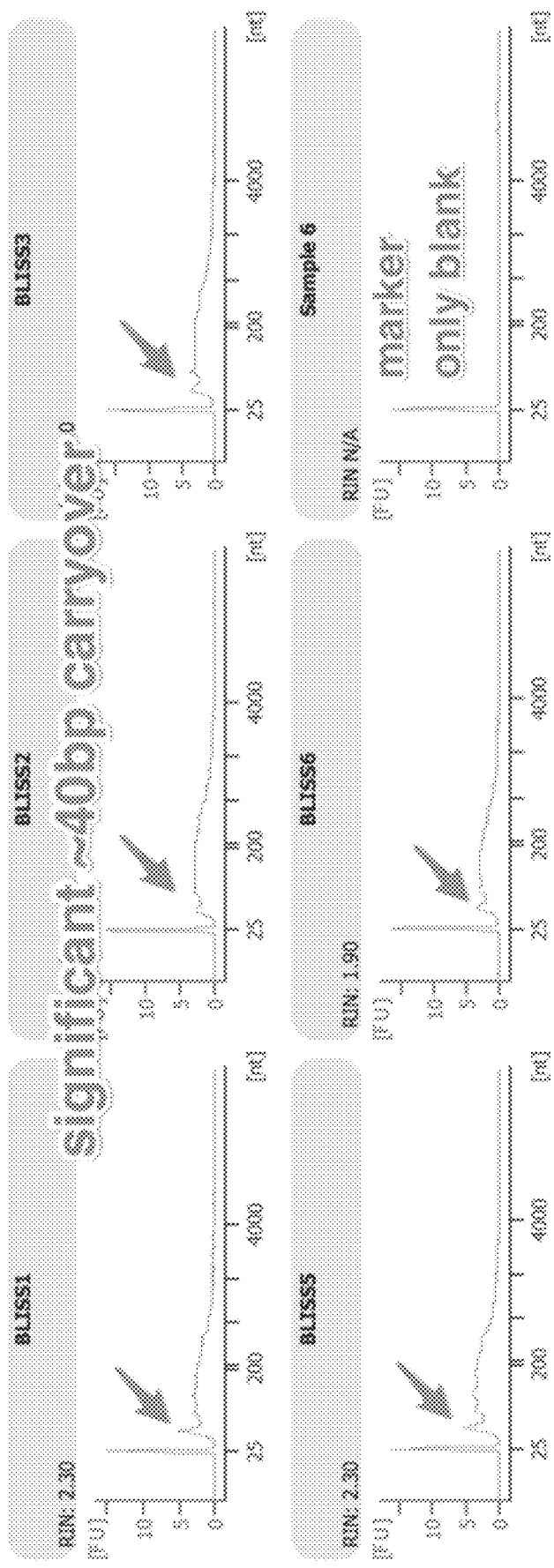
FIG. 18 depicts size distributions of reaction products. The arrows indicate 40 bp amplification products resulting from carryover of amplification primer.
Figure 19:
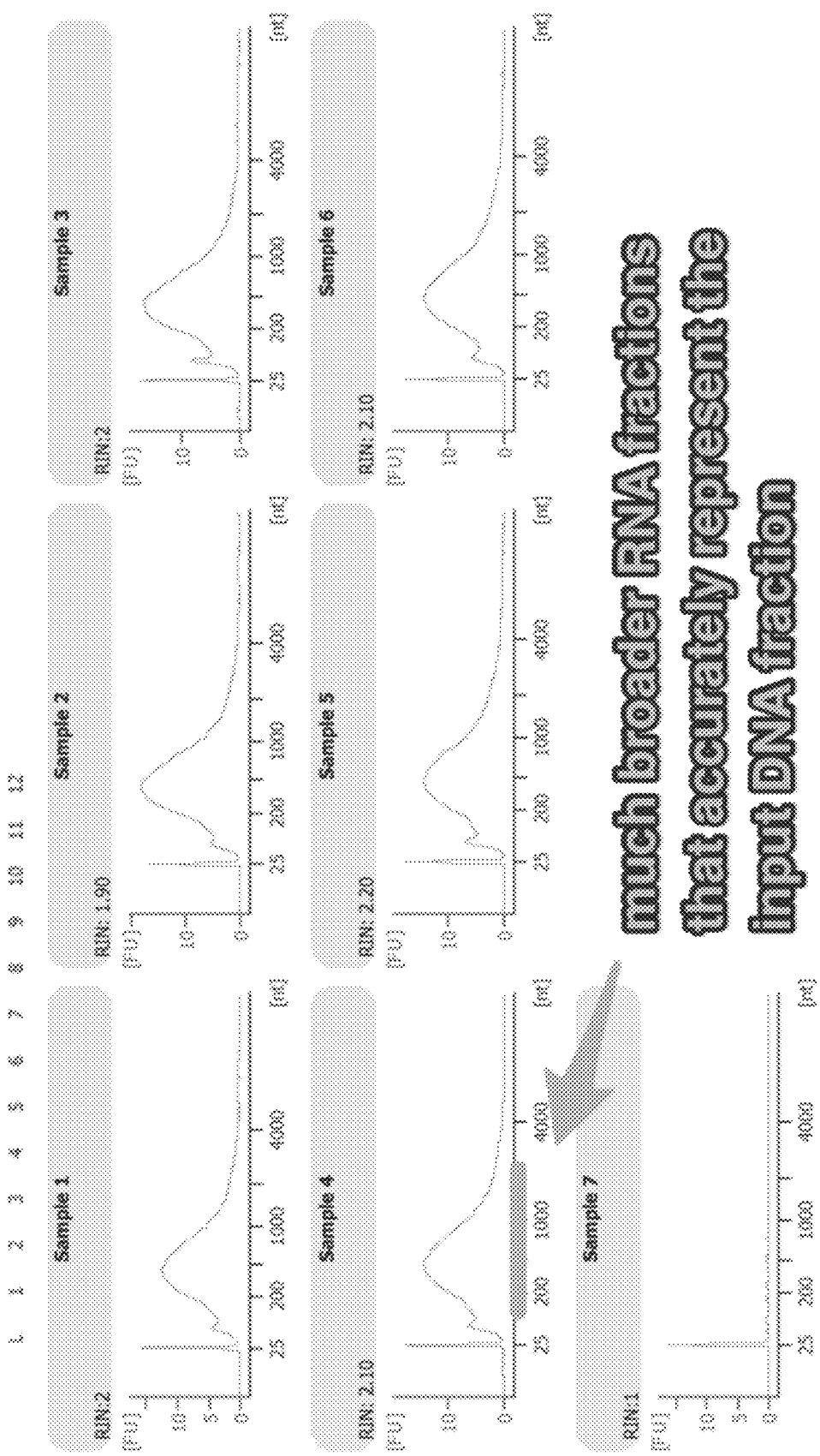
FIG. 19 depicts reactions in which carryover of amplification primer is minimized, showing relative decrease in transcripts originating from unligated primers and relative increase in RNA transcript representative of input DNA adjacent to DSBs.
Figure 20:
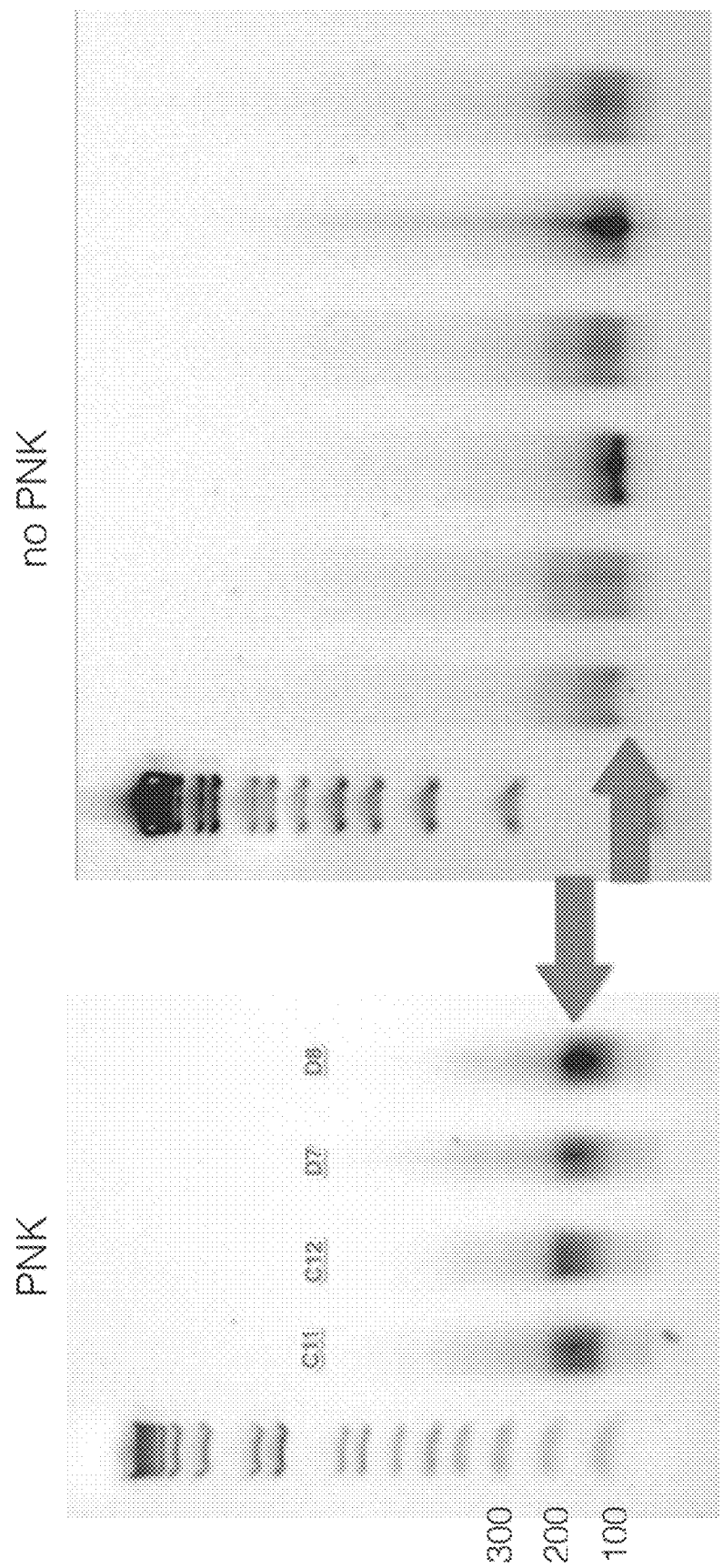
FIG. 20 demonstrates reduction of amplification products of primer multimers when primers are not treated with polynucleotide kinase (PNK).

As discussed, T7 polymerase is advantageous for IVT. A T7 adapter includes a T7 polymerase binding site for linear amplification of captured inserts and flanking DNA (FIG. 17) and can comprise a unique moleular identifier (UMI) and barcode sequences. In certain embodiments, it is advantageous to remove adapters after genomic DNA shearing and prior to IVT. In certain embodiments, bead purification is used to remove adapters. One result of insufficient adapter removal is in vitro transcription of unligated adapters (FIG. 18). Removal of adapters provides an RNA fraction that better represents the input DNA fraction. (FIG. 19).

Example 5—Unbiased Direct Detection of DSBs

Figure 21A:
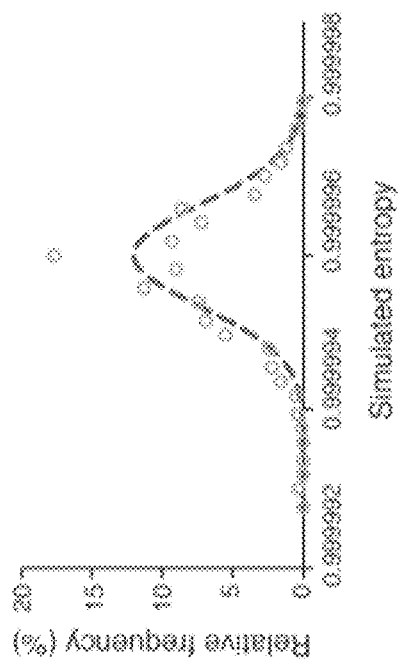
FIGS. 21A-21E depicts an analysis of DSBs in KBM7 cells (a near haploid human myeloid leukemia cell line). (A) Incorporation of Unique Molecular Identifiers (UMI). Relative base frequency at each position along the UMI is depicted. Means±s.d. are shown for n=6 experiments in KBM7 cells (see Table 2). (B) Relative frequency of telomeric C-rich strand ends in KBM7 cells. Black bars represent mean values. (C) Entropy distribution for 1,000 simulations of a uniformly distributed random breakome. Dashed line, Gaussian fit to the simulated entropy values (orange circles). (D) Reproducible ranking of chromosomes based on the number of DSB ends sequenced per chromosome in the n-6 experiments in KBM7 The rank of chromosome 8 and 15 is biased by the fact that in the near-haploid KBM7 cell line they are completely (chr8) and partially (chr15) diploid. Means±s.d. are shown. (E)
Figure 21B:
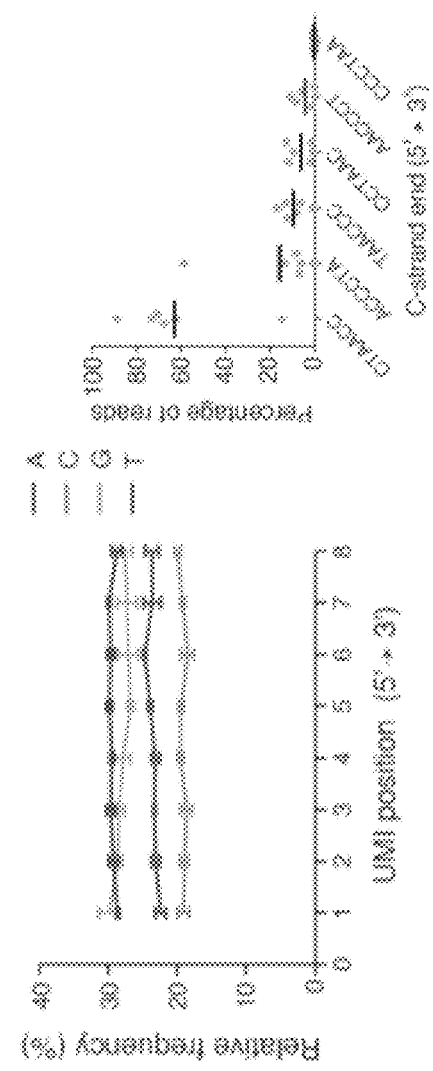

BLISS was performed in multiple samples consisting of few thousand (range: 4,000-50,000) KBM7 cells. KBM7 is a near haploid human myeloid leukemia cell line carrying a substantial amount of spontaneous DSBs. Ligation of BLISS linkers was indispensable to obtain high-quality libraries (average fraction of mapped R1 reads with expected prefix: 77.83%; n=6 samples), and UMI incorporation was effective. FIG. 21A shows relative base frequency at each position along the UMI, and is consistent with the incorporation error rates and biases during oligonucleotide synthesis (Integrated DNA Technologies Inc.). Means±s.d. are shown for n=6 experiments in KBM7 cells (see Table 2).

Sequence reads derived from the telomeric C-rich strand were examined, and 5'CCAATC was reproducibly found to be the predominant end. FIG. 1213 shows the relative frequencies of telomeric C-rich strand ends in KBM7 cells. Black bars represent mean values.

Figure 21C:
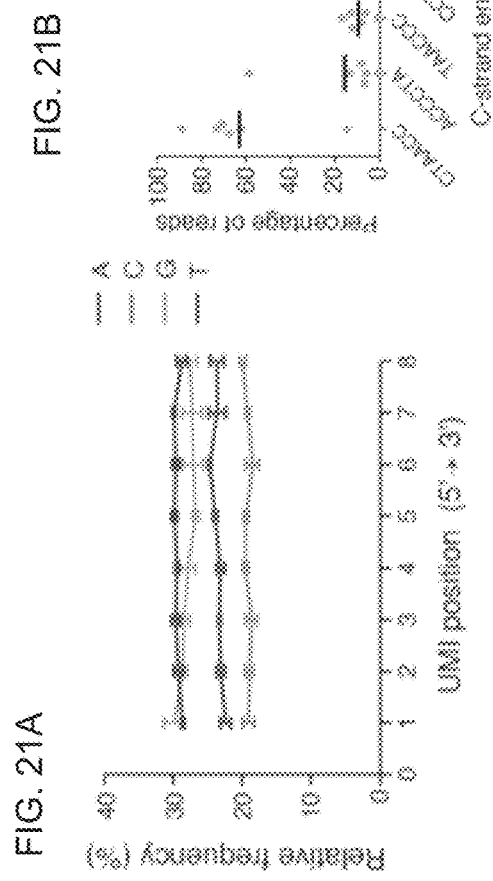
Figure 21D:
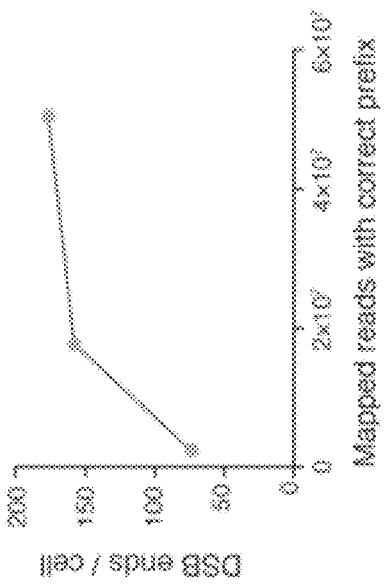

In all samples analyzed, the breakome was non-randomly distributed and reproducible across multiple experiments. FIG. 21C shows an entropy distribution for 1,000 simulations of a uniformly distributed random breakome. The dashed line is a Gaussian fit to the simulated entropy values (orange circles). From a global point of view the displacement of DSBs on the genome, as detected with and without UMIs, looks quite similar. This is not a surprise though, given the small number of cells that were used and given the sparsity and randomness of most DSBs. Still, even with these premises, it is possible to use the information provided by UMIs to detect the signal of an underlying structure. The Shannon entropy is an ideal global metric to measure the complexity of the breakome: to a given probability distribution this measure will associate a number between 0 and Log(N), where N is the number of distinguishable unique events (in this case the total number of broken genomic loci). If the entropy is close to 0 it means that the dataset has low complexity, on the other hand if the entropy is close to Log(N) the dataset will have high complexity. For each dataset, the number of different UMIs occurring in each genomic locus is listed. This list was normalized in order to obtain a list of probability values, for which the Shannon entropy was evaluated: $-\Sigma_i^N p_i \, Log(p_i)$, where $p_i$ is the i-th element in the list of probabilities. For the simulation a pool of 5,000 cells was considered, each of which could have a random number of DSBs distributed according to a Gaussian of mean 80 and variance 40. For each cell, DSBs were placed uniformly at random on a genome-proxy of length $10^9$ bases. This simulation was repeated 1,000 times and the obtained simulated datasets were processed as previously explained for the case of a real dataset in order to evaluate the Shannon entropy. In order to properly compare the entropies of datasets (real or simulated) with different number of DSBs, we divided the entropy by the logarithm of the number of unique DSBs. In this way, for each dataset, the entropy is a number between 0 and 1: the value would be 0 in the case of a distribution completely localized on a single event; it would be 1 in the case of a uniform distribution. A value between 0 and 1 tells us how much structure we see in the distribution, in the sense of being different from a uniform (or flat) distribution. The simulation results should provide a typical value of the normalized entropy very close to 1, since they are obtained from a model, which does not assume any structure in the simulated DSB locations. Indeed the simulated entropy is very well fitted by a Gaussian with mean 0.999994 and standard deviation of $1*10^{-6}$. On the other hand, the values for the normalized entropy that we obtained from experimental datasets are typically hundreds or even thousands standard deviations smaller than the simulation result. This is an indication of a structured displacement of DSBs on the genome, consistent with the co-occurrence of few fragile localized genomic regions and a majority of randomly delocalized breaks. It is important to realize that without UMIs we would not be able to measure the complexity of the breakome. FIG. 21D shows the reproducible ranking of chromosomes based on the number of USB ends sequenced per chromosome in the n-6 experiments in KBM7 cells. The rank of chromosome 8 and 15 is biased by the fact that in the near-haploid KBM7 cell line they are completely (chr8) and partially (chr15) diploid. Means±s.d. are shown.

Figure 21E:
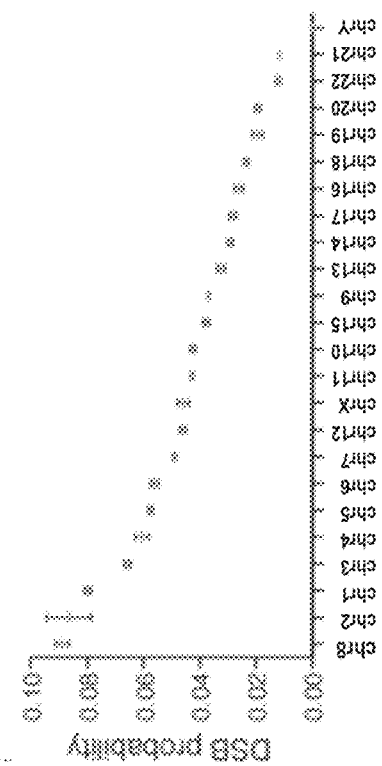
Figure 22:
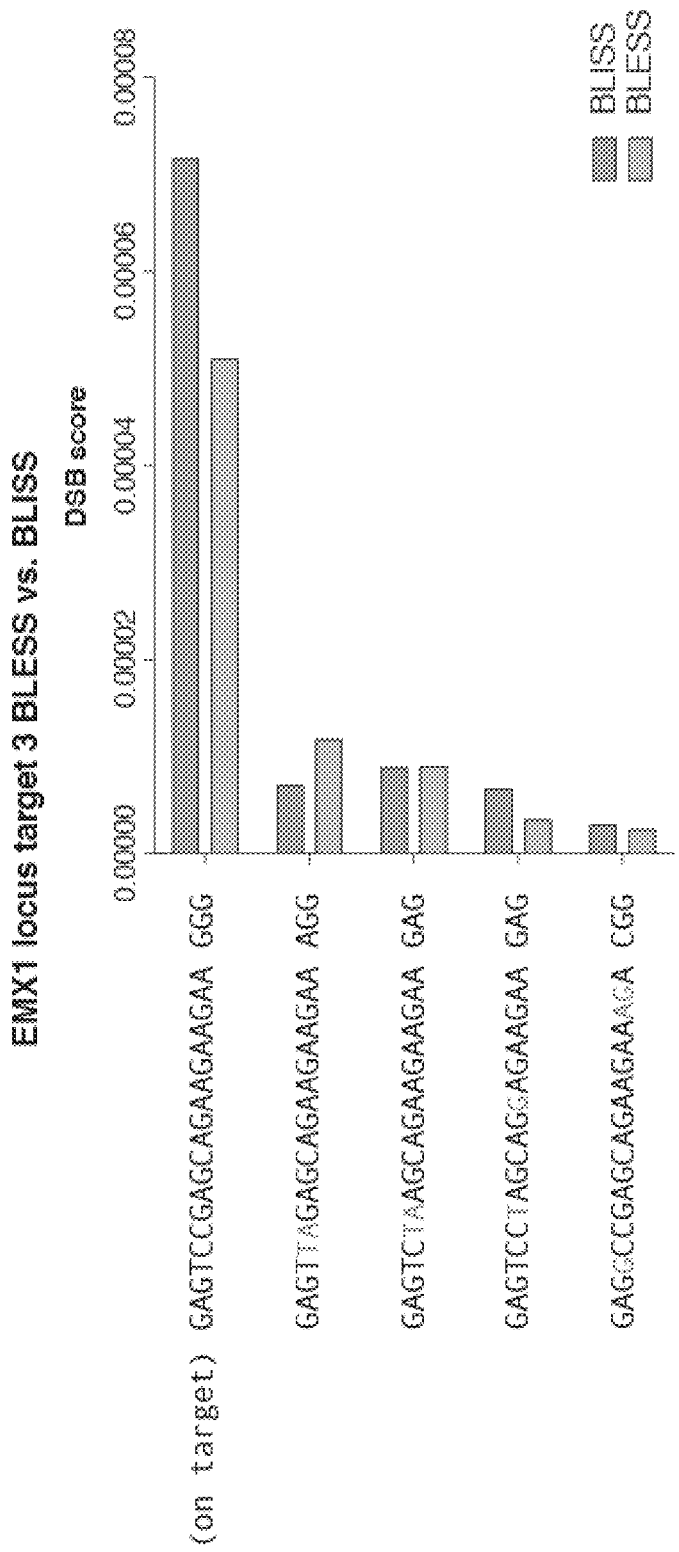
FIG. 22 depicts an analysis of BLESS vs. BLISS for unbiased off target analysis for the EMX1 locus. Approximately 2.9M reads were analyzed per sample. For the VEGFA locus, the BLESS samples had 5.8M reads while the BLISS samples used 2.9M reads. BLISS on the EMX1 locus represents 2 bioreplicate; BLESS on the EMX1 locus represents 1 bioreplicate. The analysis was done using the CRISPR-BLESS analysis pipeline described herein and in Ran et al. 2015.

Increasing-depth sequencing of 3 libraries prepared by splitting the same IVT reaction derived from ~4,000 cells showed low measurement noise (FIG. 21E). Each library was obtained from different aliquots of IVT product generated from the same sample consisting of ~4,000 KBM7 cells. The number of DSBs per cell estimated close to saturation falls within the distribution of □H2A.X foci counts in the same cell line (range: 6-381 foci per nucleus), indicating that the BLISS procedure has low propensity to produce artifacts.

TABLE 2

Summary of sequencing data

| Library | Linker | Facility | Platform | Cell type | R1 reads | R1 with prefix mapped | Unique R1 with prefix mapped |
| --- | --- | --- | --- | --- | --- | --- | --- |
| RM31 | L1 | KI | HiSeq, SE | KBM7 | 3,757,882 | 2,385,072 (63.47%) | 97,123 |
| RM32 | L1 | KI | HiSeq, SE | KBM7 | 8,737,257 | 8,117,557 (92.91%) | 33,347 |
| RM34 | L1 | KI | HiSeq, SE | KBM7 | 20,269,537 | 17,678,826 (87.22%) | 69,498 |
| RM35 | L1 | KI | HiSeq, SE | KBM7 | 58,762,254 | 50,490,299 (85.92%) | 77,733 |
| RM50 | L1-4 | NGI | MiSeq, PE | KBM7 | 11,032,410 | 6,599,653 (59.82%) | 823,694 |
| RM51 | L1-4 | NGI | MiSeq, PE | KBM7 | 12,485,740 | 9,695,678 (77.65%) | 2,111,253 |

D, dimethyl sulfoxide (DMSO) treated control. E, etoposide treated, KI, Karolinska High Throughput Center at Karolinska Institutet, Stockholm. NGI, National Genomics Infrastructure at SciLifeLab Stockholm. SE, single-end sequencing. PE, paired-end sequencing. Libraries RM50 and RM51 were obtained by pooling together 4 different samples prepared on the same day using 4 different linkers. Library RM53 was obtained by pooling together one DMSO treated sample and one sample treated with etoposide, each barcoded using a different BLISS linker. Linker sequences are listed in Table 1. RM31 and RM32 are biological replicas, whereas RM34 and RM35 are technical replicas.

Example 6—Comparison of BLISS vs. BLISS for Unbiased Off-Target Analysis

BLISS was performed for an off-target analysis of the EMX1-3 locus and the VEGFA-3 locus. For the EMX locus (FIG. 22), approximately 2.9M reads were analyzed per sample. For the VEGFA locus (FIG. 23), the BLESS samples had 5.8M reads while the BLISS samples used 2.9M reads. With the exception of BLESS on the EMX1 locus with only 1 bioreplicate, all the other samples reflect 2. bioreplicates. The analysis and DSB score were done using the CRISPR-BLESS analysis pipeline described in the Ran et al., 2015. Even though BLISS uses 40× fewer input cells than BLESS, in preliminary comparisons BLISS is able to capture nearly identical off targets identified in BLESS (FIGS. 22, 23) and can capture more DSB signal from the same locus. It is hypothesized that this is due to the reduced amount of DSB noise introduced during sample processing in BLISS.

Given the emergence of RNA-guided DNA endonuclease CRISPR-Cas9 as a versatile and efficient tool for gene editing, a significant interest has developed in evaluating the potential off-target DSBs generated. Of the recently described methods such as GUIDEseq and HTGTS, BLESS/BLISS is the only one that directly detect DSBs that have not been repaired by NHEJ or HR, thereby providing a true unbiased measurement of the off target cutting of the enzyme. Given that BLISS has equivalent or superior sensitivity to BLESS and additionally requires significantly less cell input and processing time, it can greatly expedite and expand detection off-target CRISPR activity.

Example 7—Breaks Labeling In Situ and Sequencing (Bliss) Step-By-Step Protocol

Reagents
16% methanol-free paraformaldehyde (EMS, cat. no. AM15710)
Nuclease-free Phosphate-Buffered Saline (10×) pH 7.4 (Ambion, cat. no. AM9625)
$1^{st}$ Lysis buffer: Tris-HCl 10 mM, NaCl 10 mM, EDTA 1 mM, Triton X-100 0.5%, pH 8 @ 25° C.
$2^{nd}$ Lysis buffer: Tris-HCl 10 mM, NaCl 150 mM, EDTA 1 mM, SDS 0.3%, pH 8 @ 25° C.
Nuclease-free water (Ambion, cat. no. 4387936)
CutSmart® buffer (NEB, cat. no. B7204S)
Quick Blunting™ Kit (NEB, cat. no. E1201L)
Quick Blunting™ Kit (NEB, cat. no. E1201L)
T4 DNA Ligase (NEB, cat. no. M0202M)
UltraPure™ BSA (50 mg/mL) (Ambion, cat. no. AM2616)
High-salt buffer: Tris-HCl 10 mM, NaCl 2 M, EDTA 2 mM, Triton X-100 0.5%, pH 8 @ 25° C.
HaeIII (NEB, Cat. no. R0108L)
Proteinase K, Molecular Biology Grade (NEB, P8107S)
MEGAscript® T7 Transcription Kit (Ambion, cat. no. AM1334)
RA3 adaptor and RTP, RP1 and RPI primers (custom-made by Integrated DNA Technologies Inc. based on the sequence in TruSeq Small RNA Library Preparation kit, Illumina)
RNaseOUT™ Recombinant Ribonuclease Inhibitor (Invitrogen, cat. no. 10777-019)
T4 RNA ligase 2, truncated (NEB, cat. no. M0242L)
Deoxynucleotide (dNTP) Solution Set (NEB, cat. no. N0446S)
SuperSctipt® III Reverse Transcriptase (Thermo, cat. no. 18080044)
NEBNext® High-Fidelity 2×PCR Master Mix (NEB, cat. no. M0541L)
Consumables
Eppendorf® RNA/DNA LoBind microcentrifuge tubes 0.5 ml (Sigma, cat. no. Z666521)
Eppendorf® RNA/DNA LoBind microcentrifuge tubes 1.5 ml (Sigma, cat. no. Z666548)
Sapphire Filter tips, low retention (Greiner Bio-One, cat. no. 771265, 773265, 738265, 750265)
ImmunoSelect® Adhesion Slides (MoBiTec, cat. no. SQ-IS-10)
Cell scrapers (Sigma, cat. no. C6106)

Pinpoint Slide DNA Isolation System™ (Zymo Research, cat. no. D3001)
RNeasy MinElute Cleanup Kit (Qiagen, cat. no. 74204)
Agencourt AMPure XP (Beckman Coulter, cat, no. A63880)
Qubit® dsDNA HS Assay Kit (Thermo, cat. no. Q32851)
High Sensitivity DNA Kit (Agilent, cat. no. 5067-4626)
Equipment
Cell counter (for example, we have TC20™ Automated Cell Counter, Bio-Rad)
Incubator (for example, we have a Binder incubator, Model KB 53)
Tabletop centrifuge (for example, we have a Eppendorf® Microcentrifuge 5424)
Thermoshaker (for example, we have a Eppendorf® Thermomixer Compact)
PCR cycler (for example, we have a T3 Thermocycler, Biometra)
Bioruptor® Plus sonication device (Diagenode, cat. no. B01020001)
DynaMag™-2 Magnet (Thermo, cat. no. 12321D)
Qubit® 3.0 Fluorometer (Thermo, cat. no. Q33216)
Note:
This protocol is intended for either cells spotted onto ImmunoSelect® Adhesion Slides (MoBiTec cat. no. SQ-IS-10) and covered by 105 □l SecureSear™ hybridization chambers (Grace Bio-Labs cat. no. 70333-10) or for cells grown onto 12 mm-diameter circular coverslips. For larger coverslips, washes can be performed inside multi-well cell culture plates, while in situ reactions can be done on Parafilm M®. In this case, volumes need to be adjusted accordingly. For cells on coverslips, dry the bottom of one coverslip and place it onto a microscope slide. Quickly cover the coverslip with one SecureSeal™ chamber being cautious not to touch it with the adhesive surface. Then rapidly till in the chamber with 1×PBS.

Procedure
Day 1
Cell Spotting and Fixation
For adherent cells, trypsinize the sample according to your procedure
Centrifuge 5 min @ 500 g
Aspirate the supernatant
Resuspend cells in 1×PBS @ rt
Count cells using Countess
Centrifuge 5 min™ 500 g
Resuspend cells in 1×PBS rt at a final concentration of 500-2,000 cells/µl
In the center of one ImmunoSelect® Adhesion Slide deposit 10 µl of cell suspension
Incubate for 10 min @ 25° C.
Slowly add 10 µl of 8% Paraformaldehyde in 1×PBS @ rt
Incubate for 10 min @ 25° C.
Cover the droplet with a SecureSeal™ hybridization chamber
Fill in the chamber with 1×PBS @ rt
Cell Lysis
Exchange PBS to 1$^{st}$ Lysis buffer
Incubate 1 h+4° C.
Exchange to 1×PBS @ room temperature (rt)
Incubate 5 min @ rt
Exchange to 2$^{nd}$ Lysis buffer pre-warmed @ 37° C.
Incubate 1 h in an incubator @ 37° C.
Exchange to 1×PBS @ rt
Incubate 1 min @ rt
Repeat wash in 1×PBS DSB In Situ Blunting
Exchange to 1× CutSmart buffer
Incubate 2 min @ rt
Repeat twice equilibration in 1× CutSmart buffer
Exchange to blunting mix:

| | |
|---|---|
| Nuclease-free water | 75 µl |
| Blunting buffer 10x* | 10 µl |
| BSA 10 mg/ml* | 1 µl |
| dNTPs 1 mM* | 10 µl |
| Blunting enzyme mix* | 4 µl |

*Components included in Quick Blunting ™ Kit

Incubate 1 h @ rt
DSB In Situ Ligation
Exchange to 1× CutSmart buffer
Incubate 2 min @ rt
Repeat twice wash in 1× CutSmart buffer
Exchange to 1× T4 Ligase buffer
Incubate 5 min @ rt
Exchange to ligation mix:

| | |
|---|---|
| Nuclease-free water | 75 µl |
| T4 ligase buffer 10x* | 10 µl |
| ATP 10 mM* | 8 µl |
| BSA 50 mg/ml | 2 µl |
| BLISS linker @ 10 µM | 4 µl |
| T4 ligase* | 1 µl |

*Components included in T4 DNA Ligase kit

Incubate 16-18 h in a.nincubator @ 16° C.
Day 2
In Situ DNA Fragmentation
Exchange to High-salt buffer @ rt
Quickly pipet High-salt buffer in and out of the chamber 5-6× to remove unligated
Exchange to High-salt buffer @ rt
Incubate @ 37° C.
Repeat twice exchange and incubation in High-salt buffer @ 37° C.
Exchange to 1×PBS @ rt
Incubate 2 min @ rt
Exchange to 1× CutSmart buffer
Incubate 2 min @ rt
Exchange to digestion mix:

| | |
|---|---|
| Nuclease-free water | 87 µl |
| CutSmart buffer 10x | 10 µl |
| HaeIII | 3 µl |

Incubate 3 h in an incubator @ 37° C.
Exchange to 1× CutSmart buffer
Incubate 2 min @ rt
Repeat twice wash in 1× CutSmart buffer
Breakpoint: samples can be stored in 1× CutSmart buffer @ +4° C. until DNA ex traction
Day 3
DNA Extraction
Exchange to nuclease-free water
Incubate 2 min @ rt
Repeat wash in nuclease-free water
Using a scanning bright-field microscope, image the area of the coverslip from which cells are to be taken for DNA extraction (depending on the experiment, the whole coverslip or a region thereof can be used)

With a scalpel, gently detach the SecureSear™ from the slide
Air-dry the coverslip on a piece of Kimwipes® tissue
Option 1: DNA Extraction Using PinPoint
Apply Pinpoint onto the region of interest
Note: avoid excessive use of PinPoint by spreading only a thin layer of glue onto an area of 9-10 mm²
Air-dry Pinpoint 30-40 min @ rt
With a scalpel, gently detach the Pinpoint pellet, and transfer it into a 1.5 ml DNA LoBind tube
Note: make sure the pellet is at the bottom of the tube. If the pellet gets stuck to the tube's wall, push it into the solution using a pipette tip
Add 100 µl of Pinpoint Extraction Buffer
Add 10 µl of Proteinase K
Incubate 16-18 h 55° C. shaking at 800 rpm
Option 2: Cell Scraping
Place the coverslip onto a piece of Parafilm M®
Dispense 200 µl of Pinpoint Extraction Buffer onto the coverslip
Gently scrape the cells off the coverslip
Transfer all the solution into a 1.5 ml DNA LoBind tube
Add 20 µl of Proteinase K
Incubate 16-18 h in a thermoshaker @ 55° C., shaking at 800 rpm
Day 4
Note: for all pipetting steps below use Sapphire Filter tips, low retention
DNA Sonication
Incubate 10 min @ 95° C. shaking at 800 rpm to inactivate Proteinase K
Transfer the sample to a 0.5 ml DNA LoBind tube
In a Bioruptor® sonicator set in High Power mode, perform 25 cycles 30 sec ON, 60 sec OFF
DNA Purification
Add 200 µl of Pinpoint Binding Buffer for every 100 µl Extraction Buffer used
Mix thoroughly by pipetting up and down, and transfer onto a Pinpoint column
Centrifuge 1 min @ 20,000 g
Remove the flow-through
Add 300 µl of Pinpoint Wash Buffer
Centrifuge 1 min @ 20,000 g
Remove the flow-through
Repeat the wash with Pinpoint Wash Buffer
Transfer the column to a new collection tube
Add 9 µl of nuclease-free water pre-warmed @ 55° C.
Incubate 2 min @ rt
Centrifuge 1 min @ 20,000 g
Re-load the eluate onto the same column
Incubate 2 min @ rt
Centrifuge 1 min @ 20,000 g
Transfer the eluate to a 0.5 ml DNA LoBind tube
Note: 8 µl of eluate should be obtained. If the volume is lower, add nuclease-free water up to 8 □1.
Breakpoint: samples can be stored @ −20° C. until DNA extraction
In Vitro Transcription
Add the following reagents:

| | |
|---|---|
| rNTPs mix*^ | 8 µl |
| T7 polymerase buffer 10x* | 2 µl |
| T7 polymerase* | 2 µl |

*Components included in MEGAscript ® kit
^Prepared by mixing the separate rNTP solutions provided with MEGAscript ® kit Incubate 14 h @ 37° C. In a PCR cycler with lid set @ 70° C.
Day 5
RNA Cleanup
Transfer the sample to a 1.5 ml DNA LoBind tube
Add the following reagents and thoroughly mix by pipetting up-down 5-6×:

| | |
|---|---|
| Nuclease-free water | 80 µl |
| RLT buffer* | 350 µl |
| Ice-cold 100% Ethanol | 250 µl |

*Component included in RNeasy MinElute Cleanup kit

Transfer mix to 1 RNeasy column
Centrifuge 30 sec @ 8,000 g
Transfer the column to a new RNeasy collection tube
Add 500 µl RNeasy RPE buffer
Centrifuge 30 sec @ 8,000 g
Discard the flow-through
Add 500 µl ice-cold 80% Ethanol
Centrifuge 2 min @ 8,000 g
Transfer the column to a new RNeasy collection tube
Centrifuge 5 min @ 20,000 g, with column lids open
Transfer the column to a new RNeasy collection tube
Add 8 µl RNeasy nuclease-free water
Incubate 2 min @ rt
Centrifuge 1 min @ 20,000 g
Transfer 5 µl of eluate to a 0.5 ml DNA LoBind tube
Breakpoint: samples can be stored @ −20° C.
RA3 Illumina Adapter Ligation
ON ICE Dilute RA3 adapter 1:5 in nuclease-free water
ON ICE Add 1 µl diluted RA3 adapter
In a PCR cycler, incubate 2 min @ 70° C. with the lid set @ 105° C.
Immediately place the sample on ice
ON ICI: Add 4 µl of the following mix:

| | |
|---|---|
| Nuclease-free water | 1 µl |
| T4 RNA Ligase buffer 10x* | 1 µl |
| T4 RNA Ligase 2, truncated* | 1 µl |
| RNaseO UT ™ | 1 µl |

*Components included in T4 RNA Ligase 2, truncated kit

Incubate 1 h @ 28° C. In a PCR cycler, with the lid open
Transfer the sample on ice
ON ICE Add 2 of nuclease-free water
Breakpoint: samples can be stored @ −20° C.
Reverse Transcription
ON ICE Mix each dNTP in the Deoxynucleotide (dNTP) Solution Set to obtain a dNTPs mix 25 mM
ON ICE Dilute dNTPs mix 25 mM 1:2 in nuclease-free water
ON ICE Add 2 µl RTP primer
In a PCR cycler, incubate 2 min 70° C. with the lid set @ 105° C.
Immediately place the sample on ice
ON ICE Add the following mix:

| | |
|---|---|
| Nuclease-free water | 1 µl |
| 1st strand buffer* | 4 µl |
| dNTPs mix 12.5 mM | 1 µl |

-continued

| | |
|---|---|
| DTT 100 mM* | 2 µl |
| SuperScript® III* | 2 µl |
| RNaseO UT™ | 2 µl |

*Components included in SuperScript® III Reverse Transcriptase kit

In a PCR cyder, incubate 1 h @ 50° C. with the lid set 50° C.
Breakpoint: samples can be stored @ −20° C.
Library Indexing and Amplification
ON ICE Transfer the sample into a 200 µl PCR tube
ON ICE Add 2 µl of the desired RPI primer
ON ICE Add the following mix:

| | |
|---|---|
| Nuelease-free water | 1 µl |
| RP1 primer | 2 µl |
| NEBNext® 2X PCR Master Mix | 30 µl |

In a PCR cycler with lid set @ 105° C. perform the following cycles:
1. 98° C., 30 sec
2. 98° C., 10 sec
3. 60° C., 30 sec
4. 72° C., 30 sec
5. Go to 2 and repeat for 14-20×
6. 72° C., 10 min
7. 4° C., hold
Library Cleanup
Transfer the sample into a 1.5 ml DNA LoBind tube
Add 48 µl AMPure XP bead suspension pre-warmed for 30 min @ rt
Mix thoroughly by pipetting up-down 5-6×
Incubate 5 min @ rt
Place the sample on a DynaMag™-2 Magnet
Incubate 2-3 min until all beads have attached to the magnet
Aspirate the supernatant
With the sample on the Magnetic stand, add 200 µl ice-cold 80% Ethanol
Aspirate the supernatant
Repeat wash in ice-cold 80% Ethanol
Air-dry beads 5 min @ rt
Remove the sample from the magnetic stand
Resuspend the beads in 17 µl nuclease-free water
Incubate 5 min @ rt
Place the sample on the magnetic stand
Incubate 2-3 min until all beads have attached to the magnet
Transfer 15-16 µl of cleared solution into a 1.5 ml DNA LoBind tube
Check library size on Bioanalyzer using the High Sensitivity DNA kit
Measure library concentration using Qubit® dsDNA HS Assay Kit and Qubit® 3.0 Fluorometer
Store the library @ −20° C.

Example 8—Breaks Labeling In Situ and Sequencing (BLISS) For Cells

This is the "on plate" version that can be completed inside a 24 w cell culture plate without need for transfer into SecureSeal chambers.
Day 0
For Cas9, harvest cells 24 h after transfection. Aim to transfect at 60-70% confluence, which generally means plating at ~125 k 16-18 hours before transfection. This will yield a confluent plate at harvest, so ~250 k cells go into the reaction. The more cells at this stage, the better the representation of potential off targets.
Day 1
Fixation
1. Make 4% PFA (from 16% PEA, Cat #15710 from Electron Microscopy Sciences 1× nuclease free PBS; use enough to cover well (~300 uL)
2. Fix cells for 10 minutes at RT
3. 1×PBS wash
4. Can store on PBS here.
Cell Lysis
5. Lyse plasma membrane with Cell Lysis buffer (300 uL/well):

| | |
|---|---|
| Tris-HCl | 10 mM |
| NaCl | 10 mM |
| EDTA | 1 mM |
| Igepal | 0.2% |
| pH | 8 |

6. Incubate 1 h @ +4° C.
7. Quickly rinse 2× with 1×PBS rt (400 uL/well)
8. Lyse nuclear membrane with Nucleus Break buffer pre-warmed @ 37° C. (300 uL well):

| | |
|---|---|
| Tris-HCl | 10 mM |
| NaCl | 150 mM |
| EDTA | 1 mM |
| SDS | 0.3% |
| pH | 8 |

9. incubate 1 h @ 37° C.
10. Quickly rinse insel directly aspirate) 2× with 1×PBS @ rt
DSBs Blunting
11. Wash 3× in 1× CutSmart buffer 5 min @ rt (300 uL)
12. Blunt DSBs with Blunting Mix (250 uL):

| | |
|---|---|
| Nuclease-free water | 187.5 ul |
| Blunting buffer 10× (NEB) | 25 ul |
| BSA 10 mg/ml (NEB) | 2.5 ul |
| dNTPs 1 mM (NEB) | 25 ul |
| Blunting enzyme mix | 10 ul |

13. Incubate 1 h rt
DSBs Ligation
14. Wash 2× in 1× CutSmart buffer 5 min @ rt (300 uL)
15. Wash 1× in 1× T4 Ligase buffer (NEB) 5 min @ rt (300 uL)
16. Ligate BLISS linker in Ligation Mix (250 uL) [Quick anneal for adapter preparation: program thermocycler to ramp from 95 C to 4 C over 45 min]:

| | |
|---|---|
| Nuclease-free water | 193.5 ul |
| T4 ligase buffer 10× (NEB) | 25 ul |
| ATP 10 mM (NEB) | 20 ul |

| | |
|---|---|
| BSA 50 mg/ml (Ambion) | 5 ul |
| BLISS linker @ 10 uM | 4 ul |
| T4 ligase highly conc. (NEB) | 2.5 ul |

17. Incubate 16-18 h @ 16° C.

DAY 2

In Situ gDNA Fragmentation

18. Wash 3× in Wash&Bind buffer, 1 h 37° C.:

| | |
|---|---|
| Tris-HCl | 5 mM |
| NaCl | 1 M |
| EDTA | 1 mM |
| Igepal | 0.5% |
| pH | 8 |

19. Equilibrate 5 min in 1×PBS @ rt

Breakpoint: if storing, at this point samples can be stored in 1× CutSmart buffer @ +4° C. until DNA extraction gDNA Extraction 20. Quickly wash 2× in nuclease-free water, then aspirate all water from the well.
21. Replace with 150 uL of the following mix on the well (200 uL total needed per well) [Alternatively, good recovery was obtained by letting the ProtK solution sit on the cells at RT for 1 hour and then pipetting it off. Virtually no cells were left over]

| | |
|---|---|
| Nuclease-free water | 165 ul |
| NEBuffer 2 10× (NEB) | 20 ul |
| Triton X-100 10% (1:10 from Sigma) | 10 ul |
| Proteinase K 20 mg/ml = 800 units/mL (NEB) | 5 ul |

22. Using a sterile cell scraper (CytoOne fixed blade scraper, Cat #CC7600-0220), scrape cells off the bottom of the well
23. Collect the cell suspension into a 1.5 ml DNA low-bind tube
24. Rinse 1× with 50 uL of above mix to collect remainder. At this point can check wells under microscope to see if bottom of the well has been fully scraped.
25. Incubate samples at least 5 h @ 55° C., shaking 800 rpm, overnight recommended.

Note: While ProtK inactivation can be done, heat inactivation of ProtK is incomplete and it could melt the T7 promoter adapters. Instead, ProtK removal is done with column purification after shearing.

Day 3

Fragmentation of gDNA with Bioruptor

26. In a Bioruptor instrument, perform 15 [12 cycles also works] cycles of 30 sec ON and 30 sec OFF on the high setting of a Bioruptor.
27. Confirm size distribution with 1 uL of mix on gel, aim for ~400-500 centered fragment smear.

Additional cycles of soni cation may be performed; be vigilant not to over shear because smaller fragments will be more challenging to separate out from the adapters.

gDNA Purification (Based on MessageAmp II Kit, Ambion)

28. Use a column based purification method DNA purification (Qiagen Qiaquick, Zyno DNA Clean/Concentrator 25, Thermo MicroPCR, etc. Elute in 50 uL.

Be aware of potentially losing gDNA due to column binding capacity this would reduce representation.

Preference is for columns like Qiaquick which supposedly removes products <100 bp. However, this is incomplete and an additional Ampure bead purification is needed to get rid of more adapters.

Note: cannot use Ampure beads for this step—the beads leave carryover Proteinase K that digests the T7 RNA polymerase so that your IVT has significantly lowered yield.

Adapter Elimination

This is an important step to preparing a good RNA library; an abundance of small adapters with T7 promoters will in essence sequester the T7 polymerase and prevent it from transcribing the labeled genomic loci.

29. Do a 0.8× Ampure XP bead purification to get rid of bands under ~150 bp (so add 40 uL SPRI to 50 uL of eluate from previous step)
30. Elute in 20 uL
31. Could repeat this 0.8× bead purification to get rid of even more adapter dimers.

Breakpoint: if needed, at this point samples can be stored @ −20° C. until DNA extraction In Vitro Transcription (Based on MEGAScript T7 Kit, Ambion)

32. ON ICE: to each 16 uL sample, add the following reagents:

| | |
|---|---|
| A + U + G + C* | 16 ul |
| 10× T7 polymerase buffer | 4 ul |
| T7 polymerase | 4 ul |

*Prepared from separate rNTP solutions provided with the MessageAmp II kit

If troubleshooting for protK carryover, could spike in the 0.5 ug of the control plasmid that the Ambion kit provides; this should produce ~50-100 ug of RNA.

33. Incubate 14 h @ 37° C. In a thermocycler with lid set @ 70° C.

Day 4 aRNA Cleanup (Based on RNeasy MinElute, Qiagen— Column Binds Less DNA Than Others, Necessary Because We Have a Lot of gDNA Carryover from the IVT)

Transfer samples to 1.5 ml DNA low-bind tubes

34. DNaseI digest to get rid of gDNA.

~8-10 ug of gDNA was put into the reaction and could be carried over into all downstream steps, so need to eliminate it:

| | |
|---|---|
| DNaseI buffer | 1 ul |
| Superase RNase inhibitor (20 U/uL) | 2.5 ul |
| Turbo DNaseI (2 U/uL) | 5 ul |

Generally need 1-2 U per ug of DNA

Digest for 30 min at 37 C

35. To each sample add the following reagents and thoroughly mix by pipetting up-down 5-6×:

| | |
|---|---|
| Nuclease-free water | 50 ul |
| RLT buffer | 350 ul |
| Ice-cold 100% ethanol | 250 ul |

36. Transfer mix to 1 RNA cleanup column
37. Centrifuge 30 sec @ 8,000 g, then transfer each column to a new collection tube
38. Wash 1× with 500 ul RPE buffer
39. Centrifuge 30 sec 8,000 g, then discard the flow-through
40. Wash 1× with 500 ul ice-cold 80% ethanol 41. Centrifuge 2 min @ 8,000 g, then transfer each column to a new collection tube
42. Centrifuge 5 min @ 20,000 g, with column lids open, then transfer each column to a new collection tube
43. Elute with 10 ul nuclease-free water (Qiagen) @ rt
44. Incubate 2 min @ rt
45. Centrifuge 1 min @ 20,000 g
46. Transfer 5 ul of eluate to a 0.5 ml DNA low-bind tube
47. At this point, take 1 uL for a RNA Nano bioanalyzer for evaluation of the in vitro transcribed library (take other 1 uL, for nanodrop)

Breakpoint: if needed, at this point samples can be stored @ −20° C.

3' Illumina Adapter Ligation (Based on TruSeq Small RNA Library Preparation Kit, Illumina)
48. ON ICE: dilute RA3 adapter 1:5 in nuclease-free water
49. ON ICE: to each sample add 1 ul diluted RA3
50. In a thermocycler, incubate 2 min @ 70° C., then immediately place samples on ice
51. ON ICE: to each sample add 4 ul of the following mix:

| | |
|---|---|
| RNA Ligase buffer (Illumina) | 2 ul |
| RNaseQUT (Invitrogen) | 1 ul |
| T4 RNA Ligase truncated (NEB) | 1 ul |

Total reaction volume should be 5+1+4 uL=10 uL

52. Incubate 1 h 28° C. In a thermocycler. Keep lid open if necessary to prevent heated lid from affecting temperature of reaction.
53. ON ICE: add 1 ul STOP solution, then continue incubating @ 28° C. for 15 min

[Note: No RA5 step needed because RA5 is already included in the BLISS adapter that was ligated on. The subsequent RT and PCR should enrich in the DSBs labeled by the BLISS adapter]

Breakpoint: if needed, at this point samples can be stored @ −20° C.

Reverse Transcription (1$^{st}$ Strand Synthesis) (Based on the Small RNA Kit, Illumina)
54. ON ICE: Transfer 6 μL of the 11 uL RA3+STOP reaction to a new tube.
55. ON ICE: dilute dNTPs @ 25 mM (Illumina) 1:2 in nuclease-free water
56. ON ICE: to each sample add 1 ul RTP primer
57. In a thermocycler, incubate 2 min @ 70° C., then immediately place samples on ice
58. ON ICE: to each sample add 5.5 ul of the following mix for a total of 7+5.5 uL=12.5 uL:

| | |
|---|---|
| 1$^{st}$ strand buffer (Invitrogen) | 2 ul |
| Diluted dNTPs (12.5 mM) | 0.5 ul |
| 100 mM DTT (Invitrogen) | 1 ul |
| RNaseOUT (Invitrogen) | 1 ul |
| SuperScript III (Invitrogen) | 1 ul |

59. Incubate in a thermocycler with lid set @ 50° C.:

| | |
|---|---|
| 50° C. | 60 min |
| 4° C. | Hold |

Breakpoint: if needed, at this point samples can be stored @ −20° C.

Library Indexing and Amplification
Based on the Small RNA Kit (Illumina) Protocol
60. Transfer samples into 200 ul PCR tubes
61. ON ICE: to each sample add 2 ul of the desired indexed alumina primer (RPI#, e.g., RPI1, RPI2, etc.)
62. ON ICE: to each sample add 35.5 ul of the following mix:

| | |
|---|---|
| Nuclease-free water | 8.5 ul |
| NEBNext master mix 2× (NEB) | 25 ul |
| RP1 primer | 2 ul |

63. In a thermocycler perform the following cycles [Could potentially do more cycles to enrich further . . . UMIs should detect PCR bias]:

| | | |
|---|---|---|
| 1 | 98° C. | 30 sec |
| 2 | 98° C. | 10 sec |
| 3 | 60° C. | 30 sec |
| 4 | 72° C. | 30 sec |
| | GOTO 2 14-16× | |
| 5 | 72° C. | 110 min |
| 6 | 4° C. | Hold |

Library Purification
64. Check samples on gel post PCR.
65. Do a 0.75× (or 0.8× if more conservative) Ampure bead purification to get rid of primer/adapter dimers formed at around ~150-200 bp. So add 35 uL (0.7×) or 40 uL (0.8×) Ampure beads mix to the 50 uL PCR reaction. Must be accurate here in order to not lose library.
66. Elute in 20 uL, transfer 18 uL over for analysis:
67. Check library size on Bioanalyzer using a Nigh Sensitivity DNA chip (Agilent)
68. Store libraries @ −20-20° C.

The invention is further described by the following numbered paragraphs:

1. A method for identifying the location of a double strand break (DSB) in DNA of a cell or tissue which comprises ligating an linker to the DSB to create an adapter-DSB conjugate, producing a polynucleotide complementary to the linker-DSB conjugate, and determining the sequence of the complementary polynucleotide; wherein the linker comprises i) a site for linear amplification, ii) a unique molecular identifier sequence for encoding linker-DSB ligation events; and wherein the complementary polynucleotide is a product of a linear amplification, wherein the complementary polynucleotide comprises a sequence of the DNA of the cell adjacent to the DSB.
2. The method of numbered paragraph 1, wherein the cell or tissue is a fixed cell or tissue.
3. The method of any one of numbered paragraphs 1 or 2, wherein the cell or tissue was cultured for a period of time from about 24 hours to 60 days.
4. The method of any one of numbered paragraphs 1 or 2, wherein the cell or tissue was cultured for a period of time from about 5 hours to 30 days.
5. The method of any one of numbered paragraphs 1 to 4, wherein the cell or tissue was exposed to an agent that promotes DSBs,
6. The method of numbered paragraph 3, wherein the agent comprises endonuclease activity.
7. The method of numbered paragraph 3, wherein the agent comprises a genome editing agent.

8. The method of numbered paragraph 3, wherein the agent comprises a ZFN, TALEN, or CRISPR.

9. The method of any one of numbered paragraphs 1 to 8, wherein the adapter comprises a T7 promoter sequence and the linear amplification comprises transcription by T7 polymerase.

10. The method of any one of numbered paragraphs 1 to 9, wherein the DSB is blunt ended before adapter ligation, 11. The method of any one of numbered paragraphs 1 to 10, wherein the DNA is fragmented before linear amplification.

12. The method of any one of numbered paragraphs 1 to 11, wherein the linear amplification product is an RNA.

13. The method of any one of numbered paragraphs 1 to 12, which further comprises reverse transcription and sequencing of the linear amplification product.

14. The method of any one of numbered paragraphs 1 to 13, which further comprises exponential amplification of the reverse transcript prior to sequencing.

15. A non-naturally occurring or engineered composition comprising:
    (a) DNA linker, wherein the DNA linker comprises:
        i) a unique molecular identifier sequence for encoding a linker-DSB ligation event in a target cell or tissue; and
        ii) a site for linear amplification which flanks the UMI distal to the linker-DSB ligation; and
    (b) fixed cells optionally having been cultured with an agent that promotes DSBs.

16. An unbiased method for detecting and mapping a double strand break or genomic rearrangement event in genomic DNA in a cell or cell culture of interest comprising:
    (a) transfecting or transducing a cell of interest with at least a DNA insert;
    (b) culturing the cell of interest with at least the DNA insert for a period of time from about 1 minute to 100 days prior to isolation of genomic DNA;
    (c) producing a subpopulation of cells with individual insertion events;
    (d) amplifying the DNA insert;
    (e) extracting the genomic DNA;
    (f) isolating a single stranded or a double stranded DNA fragment(s) comprising DNA inserts and flanking genomic DNA; and,
    (g) identifying a genomic sequence flanking at least one or both sides of the DNA insert.

17. The method of to numbered paragraph 16, which comprises extraction of the DNA insert at multiple time points from the transfected or transduced cell.

18. The method according to numbered paragraph 16, wherein the cells of interest are cultured for a period of time from about 24 hours to 60 days.

19. The method according to numbered paragraph 16, wherein the cells of interest are cultured for a period of time from about 5 days to 30 days.

20. The method according to any one of numbered paragraphs 16 to 19 further comprising splitting the cells comprising an individual insertion event into two fractions.

21. The method according to any one of numbered paragraphs 16 to 20 wherein the transfected or transduced cell is multiplied through cell-division and a resulting subpopulation is split into separate fractions and the DNA insert and flanking genomic DNA on either side of the DNA insert are amplified by non-restrictive linear amplification.

22. The method according to any one of numbered paragraphs 16 to 21, wherein the transfected or transduced cell is split into separate fractions and the DNA insert is first amplified using non-restrictive linear amplification then followed by exponential amplification.

23. The method according to any one of numbered paragraphs 16 to 22, wherein an amplicon is prepared by capturing at least one non-restrictive linear product on marker beads or complimentary nucleotide baits and ligated to handles comprising the DNA insert.

24. The method according to any one of numbered paragraphs 16 to 23, wherein genomic DNA isolated from transfected or transduced cells is fragmented to excise DNA inserts and flanking genomic DNA.

25. The method according to numbered paragraph 24 wherein genomic DNA isolated from transfected or transduced cells is fragmented by sonication, endonuclease digestion, or tagmentation.

26. The method according to any one of numbered paragraphs 16 to 25 wherein the amplicon is prepared by capturing a genomic fragment comprising the DNA insert or non-restrictive linear product on marker beads or complimentary nucleotide baits.

27. The method according to any one of numbered paragraphs 16 to 26 wherein the marker beads are biotinylated beads.

28. The method according to any one of numbered paragraphs 16 to 27 wherein the amplicon comprising the DNA insert and flanking genomic seqeunce is ligated to a single stranded, double stranded, or partially single stranded and double stranded DNA handle.

29. The method according to any one of numbered paragraphs 16 to 28 wherein the DNA handle comprises a unique molecular identifier for molecular counting.

30. The method according to any one of numbered paragraphs 16 to 29 wherein the DNA handle comprises a primer sequence for PCR.

31. The method according to any one of numbered paragraphs 16 to 30 wherein the DNA handle comprises a barcode for sample identification and handles for sequencing.

32. The method according to any one of numbered paragraphs 16 to 31 wherein fragments containing DNA inserts and flanking genomic DNA are isolated using affinity purification of fragments comprising DNA inserts.

33. The method according to any one of numbered paragraphs 16 to 32 wherein affinity purification of fragments include capture of DNA inserts on substrate based on incorporation of nucleic acid tags into the DNA insert or inclusion of specific sequence in the DNA insert for oligo bait affinity purification.

34. The method according to any one of numbered paragraphs 1 to 14, or 16 to 33 for use in a non-naturally occurring or engineered composition to assess the phenotypic effects of mutations at individual genomic loci or genomic rearrangement.

35. The method according to any one of numbered paragraphs 1 to 14, or 16 to 33 for use in a non-naturally occurring or engineered composition to map on and off-target genomic editing events.

36. The method according to any one of numbered paragraphs 1 to 14, or 16 to 33 for use in a non-naturally occurring or engineered composition for the identification of editing at discrete on and off-target loci.

37. A non-naturally occurring or engineered composition comprising a DNA insert wherein the DNA insert comprises:
    (a) a unique molecular identifier sequence of nuUeotrdes for encoding individual insert events in target cells;
    (b) the unique molecular identifier flanked by at least one priming site on one or both sides; and wherein the cells are cultured for a period of time of about 1 minute to 100 days prior to isolation of genomic DNA; and, optionally, wherein modified nucleotides are added to the DNA insert to enhance to enhance nuclear penetration of insert, insert stability, or insertion efficiency.

38. A non-naturally occurring or engineered composition comprising a DNA insert which comprises:
(a) at least one priming site or a defined nucleic acid sequence;
optionally, wherein the nucleic acid sequence contains homology to a genomic locus of interest for homology directed incorporation of the DNA insert;
(b) a unique molecular identifier sequence of nucleotides for encoding individual insert events in target cells;
(c) the unique molecular identifier is flanked by at least one priming site or a nucleic acid buffer sequence on one or both sides;
optionally, wherein a flanking sequence contains homology to a genomic locus of interest for homology directed incorporation of the DNA insert;
(d) the DNA insert contains at least one or more modified nucleic acids to enhance nuclear penetration of insert, insert stability, or insertion efficiency;
(e) the DNA insert contains at least one or more modified nucleic acids for affinity capture or specific nucleotide sequences for capture on oligonucleotide baits;
(f) at least two type II nuclease sites at a 5' and 3' end of the DNA insert for excision of the DNA insert and flanking the unique molecular identifier following insert integration in to genomic DNA; and,
wherein the cells are cultured for a period of time of about 1 minute to 100 days prior to isolation of genomic DNA.

39. The non-naturally occurring or engineered composition comprising a unique molecular identifier according to numbered paragraph 37 or 38 wherein the unique molecular identifier is either an event barcode or a ligation barcode.

40. The non-naturally occurring or engineered composition comprising a unique molecular identifier according to numbered paragraph 37 or 38 wherein the DNA insert is either a partially double stranded DNA insert or a partially single stranded DNA insert.

41. The non-naturally occurring or engineered composition comprising a unique molecular identifier according to numbered paragraph 38 wherein the partially single stranded DNA insert comprises a short 3' double strand cap.

42. The non-naturally occurring or engineered composition comprising a unique molecular identifier according to numbered paragraph 37 or 38 wherein the nucleotide sequence is greater than 3 nucleotides in length.

43. The non-naturally occurring or engineered composition comprising a unique molecular identifier according to numbered paragraph 37 or 38 wherein the nucleotide sequence is anywhere from 5 to 30 nucleotides in length.

44. The non-naturally occurring or engineered composition comprising a unique molecular identifier according to numbered paragraph 37 or 38 wherein the nucleotide sequence is anywhere from 10 to 25 nucleotides in length.

45. The non-naturally occurring or engineered composition comprising a unique molecular identifier according to numbered paragraph 37 or 38 wherein the nucleotide sequence is anywhere from 15 to 20 nucleotides in length 46. The non-naturally occurring or engineered composition comprising a unique molecular identifier according to numbered paragraph 37 or 38 wherein the nucleotide sequence is 18 nucleotides in length.

47. The non-naturally occurring or engineered composition comprising a unique molecular identifier according to numbered paragraph 37 or 38 wherein the nucleotide sequence is in a random sequence.

48. The non-naturally occurring or engineered composition comprising a unique molecular identifier according to any one of numbered paragraphs 37 to 47 wherein one or more priming sites flanking the event barcode comprise different sequences.

49. The non-naturally occurring or engineered composition comprising a unique molecular identifier or event barcode according to any one of numbered paragraphs 37 to 48 wherein the extraction of genomic sequences occur at multiple time points.

50. The non-naturally occurring or engineered composition comprising a unique molecular identifier or event barcode according to any one of numbered paragraphs 37 to 49 wherein unique insertion events are identified at genomic loci.

51. A kit for isolating, purifying, amplifying, detecting, identifying or quantifying a genomic DNA sequence comprising a composition according to any one of numbered paragraphs 37 to 50.

52. A kit for using a non-naturally occurring or engineered composition according any one of numbered paragraphs 37 to 50 to map and detect double strand breaks in genomic DNA in a cell of interest comprising:
(a) transfecting a cell of interest with at least a DNA insert;
(b) passaging the cells of interest with at least the DNA insert for a period of about 24 hours to 30 days prior to isolation of genomic DNA;
(c) producing a subpopulation of cells with individual insertion events;
(d) splitting the subpopulation of cells encoding an individual insertion event into two fractions;
(e) amplifying the DNA insert;
(e) extraction of the genomic DNA.

REFERENCES

1. Crosetto, N. et al. Nucleotide-resolution DNA double-strand break mapping by next-generation sequencing. *Nat. Methods* 10, 361-365 (2013).
2. Ran, F. A. et al. In vivo genome editing using *Staphylococcus aureus* Cas9. *Nature* 520, 186-191 (2015).
3. Kivioja, T. et al. Counting absolute numbers of molecules using unique molecular identifiers. *Nat. Methods* 9, 72-74 (2012).
4. Sfeir, A. J., Chai, W., Shay, J. W. & Wright, W. E. Telomere-end processing the terminal nucleotides of human chromosomes. Mol. Cell 18, 131-138 (2005).
5. Baranello, L. et al. DNA break mapping reveals topoisomerase II activity genome-wide. *Int J Mol Sci* 15, 13111-13122 (2014).
6. Leduc, F. et al. Genome-wide mapping of DNA strand breaks. *PLoS ONE* 6, e17353 (2011).
7. Gabriel, R. et al. An unbiased genome-wide analysis of zinc-finger nuclease specificity. *Nat. Biotechnol.* 29, 816-823 (2011).
8. Tsai, S. Q. et al. GUIDE-seq enables genome-wide profiling of off-target cleavage by CRISPR-Cas nucleases. *Nat. Biotechnol.* 33, 187-197 (2015).

9. Frock, R. L. et al. Genome-wide detection of DNA double-stranded breaks induced by engineered nucleases. *Nat. Biotechnol.* 33, 179-186 (2015).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for identifying the location of at least one double strand break (DSB) in DNA of a cell or tissue, the method comprising:
   a) ligating a linker to each end of the DSB to create a linker-DSB conjugate at each end, wherein the linker comprises:
      i) a promoter sequence for linear amplification, and
      ii) a unique molecular identifier sequence;
   b) producing a polynucleotide complementary to the linker-DSB conjugate by linear amplification; and
   c) determining the sequence of the complementary polynucleotide, whereby the location of the DSB is identified;

wherein each linker comprises a different unique molecular identifier sequence, and wherein the complementary polynucleotide comprises a sequence of the DNA adjacent to the DSB.

2. The method of claim 1, wherein the cell or tissue is a fixed cell or issue.

3. The method of claim 1, wherein the cell or tissue was cultured for a period of time from 24 hours to 60 days.

4. The method of claim 1, wherein the cell or tissue was cultured for a period of time from 5 hours to 30 days.

5. The method of claim 1, wherein the cell or tissue was exposed to an agent that promotes DSBs.

6. The method of claim 5, wherein the agent comprises endonuclease activity.

7. The method of claim 5, wherein the agent comprises a genome editing agent.

8. The method of claim 5, wherein the agent comprises a ZFN, TALEN, or CRISPR.

9. The method of claim 1, wherein the DSB is blunt ended before linker ligation.

10. The method of claim 1, wherein the DNA is fragmented before linear amplification.

11. The method of claim 1, wherein the linear amplification product is an RNA.

12. The method of claim 1, which further comprises reverse transcription and sequencing of the linear amplification product.

13. The method of claim 12, which further comprises exponential amplification of the reverse transcript prior to sequencing.

14. The method according to claim 1 for use in a non-naturally occurring or engineered composition to assess the phenotypic effects of mutations at individual genomic loci or genomic rearrangement.

15. The method according to claim 1 for use in a non-naturally occurring or engineered composition to map on and off-target genomic editing events.

16. The method according to claim 1 for use in a non-naturally occurring or engineered composition for the identification of editing at discrete on and off-target loci.

17. The method of claim 1, wherein the promoter sequence is a T7 promoter sequence.

18. The method of claim 1, wherein the linker is ligated to a single strand or both strands of the DSB.

19. The method of claim 18, wherein this ligated to the 5' end of the single strand.

20. The method of claim 18, wherein the linker is ligated to the 3' end of the single strand.

21. The method of claim 18, wherein the linker comprises a blunt end, a 5' overhang, or a 3' overhang.

\* \* \* \* \*

SEQUENCE LISTING

```
<160> NUMBER OF SEQ ID NOS: 77

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 1
nnnnnnnnnn nnnnnnnnnn ngg                                            23

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 2
nnnnnnnnnn nnngg                                                     15

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 3
nnnnnnnnnn nnnnnnnnnn ngg                                            23

<210> SEQ ID NO 4
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 4
nnnnnnnnnn nngg                                                            14

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 5
nnnnnnnnnn nnnnnnnnnn nnagaaw                                              27

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 6
nnnnnnnnnn nnnnagaaw                                                       19

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 7
```
nnnnnnnnnn nnnnnnnnnn nnagaaw                                          27

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 8
nnnnnnnnnn nnnagaaw                                                    18

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 9
nnnnnnnnnn nnnnnnnnnn nggng                                            25

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 10
nnnnnnnnnn nnnggng                                                     17

<210> SEQ ID NO 11
<211> LENGTH: 25
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 11
nnnnnnnnnn nnnnnnnnnn nggng                                         25

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 12
nnnnnnnnnn nnggng                                                   16

<210> SEQ ID NO 13
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 13
nnnnnnnnnn nnnnnnnnnn gttttttgtac tctcaagatt tagaaataaa tcttgcagaa    60
gctacaaaga taaggcttca tgccgaaatc aacaccctgt cattttatgg cagggtgttt   120
tcgttattta attttt                                                  137

<210> SEQ ID NO 14
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 14
```
nnnnnnnnnn nnnnnnnnnn gttttttgtac tctcagaaat gcagaagcta caaagataag    60
gcttcatgcc gaaatcaaca ccctgtcatt ttatggcagg gtgttttcgt tatttaattt   120
ttt                                                                 123

<210> SEQ ID NO 15
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 15
nnnnnnnnnn nnnnnnnnnn gttttttgtac tctcagaaat gcagaagcta caaagataag    60
gcttcatgcc gaaatcaaca ccctgtcatt ttatggcagg gtgttttttt              110

<210> SEQ ID NO 16
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 16
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 17
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 17
nnnnnnnnnn nnnnnnnnnn gttttagagc tagaaatagc aagttaaaat aaggctagtc    60
cgttatcaac ttgaaaaagt gttttttt                                       88

<210> SEQ ID NO 18
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 18

```
nnnnnnnnnn nnnnnnnnnn gttttagagc tagaaatagc aagttaaaat aaggctagtc    60
cgttatcatt tttttt                                                   76

<210> SEQ ID NO 19
<211> LENGTH: 20
<212> TYPE: DNA
<213> ORGANISM: Homo sapiens

<400> SEQUENCE: 19
gagtccgagc agaagaagaa                                               20

<210> SEQ ID NO 20
<211> LENGTH: 20
<212> TYPE: DNA
<213> ORGANISM: Homo sapiens

<400> SEQUENCE: 20
gagtcctagc aggagaagaa                                               20

<210> SEQ ID NO 21
<211> LENGTH: 20
<212> TYPE: DNA
<213> ORGANISM: Homo sapiens

<400> SEQUENCE: 21
gagtctaagc agaagaagaa                                               20

<210> SEQ ID NO 22
<211> LENGTH: 7
<212> TYPE: PRT
<213> ORGANISM: Simian virus 40

<400> SEQUENCE: 22

Pro Lys Lys Lys Arg Lys Val
1               5

<210> SEQ ID NO 23
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 23

Lys Arg Pro Ala Ala Thr Lys Lys Ala Gly Gln Ala Lys Lys Lys Lys
1               5                   10                  15

<210> SEQ ID NO 24
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 24

Pro Ala Ala Lys Arg Val Lys Leu Asp
1               5

<210> SEQ ID NO 25
<211> LENGTH: 11
<212> TYPE: PRT
<213> ORGANISM: Unknown
<220> FEATURE:
```

```
<223> OTHER INFORMATION: Description of Unknown:
      C-myc NLS sequence

<400> SEQUENCE: 25

Arg Gln Arg Arg Asn Glu Leu Lys Arg Ser Pro
1               5                   10

<210> SEQ ID NO 26
<211> LENGTH: 38
<212> TYPE: PRT
<213> ORGANISM: Homo sapiens

<400> SEQUENCE: 26

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 27
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 27

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 28
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 28

Val Ser Arg Lys Arg Pro Arg Pro
1               5

<210> SEQ ID NO 29
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 29

Pro Pro Lys Lys Ala Arg Glu Asp
1               5

<210> SEQ ID NO 30
<211> LENGTH: 8
<212> TYPE: PRT
<213> ORGANISM: Homo sapiens
```

```
<400> SEQUENCE: 30

Pro Gln Pro Lys Lys Pro Leu
1               5

<210> SEQ ID NO 31
<211> LENGTH: 12
<212> TYPE: PRT
<213> ORGANISM: Mus musculus

<400> SEQUENCE: 31

Ser Ala Leu Ile Lys Lys Lys Lys Lys Met Ala Pro
1               5                   10

<210> SEQ ID NO 32
<211> LENGTH: 5
<212> TYPE: PRT
<213> ORGANISM: Influenza virus

<400> SEQUENCE: 32

Asp Arg Leu Arg Arg
1               5

<210> SEQ ID NO 33
<211> LENGTH: 7
<212> TYPE: PRT
<213> ORGANISM: Influenza virus

<400> SEQUENCE: 33

Pro Lys Gln Lys Lys Arg Lys
1               5

<210> SEQ ID NO 34
<211> LENGTH: 10
<212> TYPE: PRT
<213> ORGANISM: Hepatitis delta virus

<400> SEQUENCE: 34

Arg Lys Leu Lys Lys Lys Ile Lys Lys Leu
1               5                   10

<210> SEQ ID NO 35
<211> LENGTH: 10
<212> TYPE: PRT
<213> ORGANISM: Mus musculus

<400> SEQUENCE: 35

Arg Glu Lys Lys Lys Phe Leu Lys Arg Arg
1               5                   10

<210> SEQ ID NO 36
<211> LENGTH: 20
<212> TYPE: PRT
<213> ORGANISM: Homo sapiens

<400> SEQUENCE: 36

Lys Arg Lys Gly Asp Glu Val Asp Gly Val Asp Glu Val Ala Lys Lys
1               5                   10                  15

Lys Ser Lys Lys
            20

<210> SEQ ID NO 37
<211> LENGTH: 17
<212> TYPE: PRT
<213> ORGANISM: Homo sapiens
```

<400> SEQUENCE: 37

Arg Lys Cys Leu Gln Ala Gly Met Asn Leu Glu Ala Arg Lys Thr Lys
1               5                   10                  15

Lys

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Gly Ser Gly Gly Gly Gly Ser Gly Gly Gly Gly Ser
1               5                   10                  15

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 40
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 41
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Ser
        50                  55                  60

<210> SEQ ID NO 42
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
guuuuagagc ua                                                         12

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Gly Ser
1

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Ser Gly Gly Gly Ser Gly Gly Gly Ser
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Glu Ala Ala Ala Lys Ala
1               5

<210> SEQ ID NO 46
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(16)
<223> OTHER INFORMATION: a, c, t, g, unknown or other

<400> SEQUENCE: 46
gcgtgatgnn nnnnnngatc gtcggactgt agaactctga accccctatag tgagtcgtat     60 taccggcctc aatcgaa                                                    77

<210> SEQ ID NO 47

```
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (60)..(67)
<223> OTHER INFORMATION: a, c, t, g, unknown or other

<400> SEQUENCE: 47
cgattgaggc cggtaatacg actcactata ggggttcaga gttctacagt ccgacgatcn    60
nnnnnnncat cacgc                                                    75

<210> SEQ ID NO 48
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 48
nnnnnnnnga tcgtcggact gtagaactct gaacccctat agtgagtcgt attaccggcc    60
tcaatcgaa                                                           69

<210> SEQ ID NO 49
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (60)..(67)
<223> OTHER INFORMATION: a, c, t, g, unknown or other

<400> SEQUENCE: 49
cgattgaggc cggtaatacg actcactata ggggttcaga gttctacagt ccgacgatcn    60
nnnnnnngtc gttcc                                                    75

<210> SEQ ID NO 50
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (60)..(67)
<223> OTHER INFORMATION: a, c, t, g, unknown or other

<400> SEQUENCE: 50
cgattgaggc cggtaatacg actcactata ggggttcaga gttctacagt ccgacgatcn    60
nnnnnnnttg atgatc                                                   76

<210> SEQ ID NO 51
<211> LENGTH: 75
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (60)..(67)
<223> OTHER INFORMATION: a, c, t, g, unknown or other

<400> SEQUENCE: 51
cgattgaggc cggtaatacg actcactata ggggttcaga gttctacagt ccgacgatcn    60
nnnnnnntga tgcgc                                                    75

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggtgagtgag tgtgtgcgtg tgg                                           23

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtgagtgagt gtgtgtgtgg gg                                            22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtgggtgagt gtgtgcgtga gg                                            22

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gctgagtgag tgtatgcgtg tgg                                           23

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gagagtgagt gtgtgcatga gg                                            22
```

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gtgtgtgagt gtgtgcgtgt gg                                              22

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggtgagtgag tgcgtgcggg tgg                                             23

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcgagtgggt gtgtgcgtgg gg                                              22

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggtggatgag tgtgtgtgtg ggg                                             23

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gtgaatgagt gtgtgtgtgt gg                                              22

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggtgagtgag tgtgtgtgtg agg                                             23

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gtgagttgag tgatctgggt tgag                                          24

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggggaatgag tgtgtgcatg gag                                           23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggtgagtgtg tgtgtgcatg tgg                                           23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gtgggtgagt gtgtgcgtga gag                                           23

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gggagtgact gtgtgcgtgt gg                                            22

<210> SEQ ID NO 68
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (60)..(67)
<223> OTHER INFORMATION: a, c, t, g, unknown or other

<400> SEQUENCE: 68

```
cgattgaggc cggtaatacg actcactata ggggttcaga gttctacagt ccgacgatcn    60
nnnnnnngtc gtatc                                                    75
```

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69

```
gagtccgagc agaagaagaa ggg                                           23
```

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70

```
gagttagagc agaagaagaa agg                                           23
```

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71

```
gagtctaagc agaagaagaa gag                                           23
```

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

```
gagtcctagc aggagaagaa gag                                           23
```

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73

```
gaggccgagc agaagaaaga cgg                                           23
```

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74

```
gttgagtgaa tgtgtgcgtg agg                                            23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gtgagtgagt gtgtgtgtgt gag                                            23

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggtagagtga gtgtgtgtgt gtgg                                           24

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gatgagtgtg tgtgtgtgtg agg                                            23
```